(12) United States Patent
Frimer et al.

(10) Patent No.: US 10,751,139 B2
(45) Date of Patent: *Aug. 25, 2020

(54) DEVICE AND METHOD FOR ASSISTING LAPAROSCOPIC SURGERY—RULE BASED APPROACH

(71) Applicant: TransEnterix Europe S.a.r.l., Lugano (CH)

(72) Inventors: Motti Frimer, Zichron Yaakov (IL); Mordehai Sholev, Moshav Amikam (IL); Yehuda Pfeffer, Moshav Adirim (IL)

(73) Assignee: TransEnterix Europe S.a.r.l., Lugano (TI) (CH)

( * ) Notice: Subject to any disclaimer, the term of this patent is extended or adjusted under 35 U.S.C. 154(b) by 0 days.

This patent is subject to a terminal disclaimer.

(21) Appl. No.: 16/176,854

(22) Filed: Oct. 31, 2018

(65) Prior Publication Data

US 2019/0117323 A1 Apr. 25, 2019

Related U.S. Application Data

(60) Division of application No. 15/289,324, filed on Oct. 10, 2016, now Pat. No. 10,201,392, which is a
(Continued)

(51) Int. Cl.
*G06F 19/00* (2018.01)
*A61B 34/32* (2016.01)
(Continued)

(52) U.S. Cl.
CPC .......... *A61B 34/32* (2016.02); *A61B 1/00006* (2013.01); *A61B 1/00009* (2013.01);
(Continued)

(58) Field of Classification Search
CPC ............ A61B 19/5244; A61B 1/00006; A61B 1/3132; A61B 2019/2211; A61B 19/2203
See application file for complete search history.

(56) References Cited

U.S. PATENT DOCUMENTS 5,494,034 A * 2/1996 Schlondorff ........... A61B 6/032
600/425
6,179,776 B1 * 1/2001 Adams ............... A61B 1/00073
600/121
(Continued)

OTHER PUBLICATIONS

International Search Report for PCT/IL2012/000310, filed Aug. 21, 2012.
(Continued)

*Primary Examiner* — Khoi H Tran
*Assistant Examiner* — Jorge O Peche

(57) ABSTRACT

The present invention provides a surgical controlling system, comprising: a. at least one surgical tool configured to be insertable into a surgical environment of a human body for assisting a surgical procedure; b. at least one location estimating means configured to real-time locate the 3D spatial position of said at least one surgical tool at any given time t; c. at least one movement detection means communicable with a movement's database and with said location estimating means; and, d. a controller having a processing means communicable with a controller's database, said controller configured to control the spatial position of said at least one surgical tool; said controller's database is in communication with said movement detection means.

4 Claims, 26 Drawing Sheets

Related U.S. Application Data continuation of application No. 14/752,947, filed on Jun. 28, 2015, now Pat. No. 9,504,456, which is a division of application No. 14/150,939, filed on Jan. 9, 2014, now Pat. No. 9,204,939, which is a continuation-in-part of application No. PCT/IL2012/000310, filed on Aug. 21, 2012.

(60) Provisional application No. 61/750,856, filed on Jan. 10, 2013, provisional application No. 61/525,779, filed on Aug. 21, 2011, provisional application No. 61/525,787, filed on Aug. 21, 2011, provisional application No. 61/525,789, filed on Aug. 21, 2011.

(51) Int. Cl.

| | | |
|---|---|---|
| *A61B 1/313* | (2006.01) | |
| *A61B 1/00* | (2006.01) | |
| *A61B 90/50* | (2016.01) | |
| *A61B 17/00* | (2006.01) | |
| *G05B 15/02* | (2006.01) | |
| *A61B 34/20* | (2016.01) | |
| *A61B 1/04* | (2006.01) | |
| *A61B 1/06* | (2006.01) | |
| *A61B 90/00* | (2016.01) | |
| *A61B 90/98* | (2016.01) | |
| *A61B 34/30* | (2016.01) | |

(52) U.S. Cl.
CPC ...... *A61B 1/00147* (2013.01); *A61B 1/00149* (2013.01); *A61B 1/04* (2013.01); *A61B 1/06* (2013.01); *A61B 1/3132* (2013.01); *A61B 17/00234* (2013.01); *A61B 34/20* (2016.02); *A61B 90/361* (2016.02); *A61B 90/50* (2016.02); *A61B 90/98* (2016.02); *G05B 15/02* (2013.01); *A61B 34/30* (2016.02); *A61B 2017/00075* (2013.01); *A61B 2017/00132* (2013.01); *A61B 2017/00225* (2013.01); *A61B 2034/2048* (2016.02); *A61B 2034/2051* (2016.02); *A61B 2034/2055* (2016.02); *A61B 2034/2057* (2016.02); *A61B 2034/2059* (2016.02); *A61B 2034/2065* (2016.02); *A61B 2034/2074* (2016.02); *A61B 2090/365* (2016.02); *A61B 2090/367* (2016.02); *A61B 2090/371* (2016.02); *A61B 2090/3945* (2016.02); *A61B 2090/3983* (2016.02)

(56) References Cited

U.S. PATENT DOCUMENTS

| | | | |
|---|---|---|---|
| 6,714,841 B1 | 3/2004 | Wright et al. | |
| 6,837,883 B2* | 1/2005 | Moll | A61B 34/30 606/1 |
| 7,087,049 B2* | 8/2006 | Nowlin | A61B 34/70 606/1 |
| 8,079,950 B2* | 12/2011 | Stern | A61B 1/00188 600/109 |
| 8,758,263 B1* | 6/2014 | Rahimian | A61B 10/0233 600/562 |
| 8,992,542 B2* | 3/2015 | Hagag | A61B 34/20 606/99 |
| 9,204,939 B2 | 12/2015 | Frimer et al. | |
| 9,504,456 B2 | 11/2016 | Frimer et al. | |
| 9,757,204 B2 | 9/2017 | Frimer et al. | |
| 2002/0091301 A1* | 7/2002 | Levin | A61B 17/00234 600/37 |
| 2003/0216833 A1* | 11/2003 | Mukai | B25J 9/1602 700/245 |
| 2004/0089777 A1* | 5/2004 | Schilt | A61B 90/50 248/227.2 |
| 2004/0111183 A1* | 6/2004 | Sutherland | A61B 34/77 700/245 |
| 2005/0219552 A1* | 10/2005 | Ackerman | A61B 1/042 356/603 |
| 2007/0005045 A1* | 1/2007 | Mintz | A61B 34/74 606/1 |
| 2007/0013336 A1* | 1/2007 | Nowlin | A61B 34/30 318/568.21 |
| 2007/0021713 A1* | 1/2007 | Kumar | A61M 3/0229 604/27 |
| 2007/0021752 A1* | 1/2007 | Rogers | A61B 17/162 606/80 |
| 2008/0154389 A1* | 6/2008 | Smith | A61B 5/064 700/24 |
| 2008/0215181 A1* | 9/2008 | Smith | A61B 90/36 700/245 |
| 2008/0234866 A1* | 9/2008 | Kishi | A61B 34/30 700/259 |
| 2008/0275452 A1* | 11/2008 | Lang | A61B 17/15 606/88 |
| 2008/0300453 A1* | 12/2008 | Aoki | A61B 34/73 600/103 |
| 2009/0043310 A1* | 2/2009 | Rasmussen | A61B 17/157 606/88 |
| 2009/0088774 A1* | 4/2009 | Swarup | A61B 34/30 606/130 |
| 2009/0099520 A1* | 4/2009 | Millman | A61M 1/0058 604/131 |
| 2009/0216114 A1* | 8/2009 | Gorges | A61B 90/36 600/425 |
| 2009/0240259 A1* | 9/2009 | Nelson | A61B 34/30 606/130 |
| 2009/0248037 A1* | 10/2009 | Prisco | A61B 34/37 606/130 |
| 2010/0022871 A1* | 1/2010 | De Beni | A61B 8/483 600/424 |
| 2010/0036198 A1* | 2/2010 | Tacchino | A61B 17/29 600/106 |
| 2010/0234857 A1* | 9/2010 | Itkowitz | A61B 34/77 606/130 |
| 2011/0177469 A1* | 7/2011 | Suter | A61C 8/0089 433/75 |
| 2012/0071893 A1* | 3/2012 | Smith | A61B 90/11 606/130 |
| 2012/0245415 A1* | 9/2012 | Emura | A61B 1/0005 600/109 |
| 2014/0221738 A1* | 8/2014 | Sholev | A61B 1/00149 600/102 |
| 2016/0015473 A1* | 1/2016 | Frimer | A61B 1/00149 606/130 |

OTHER PUBLICATIONS

International Preliminary Report on Patentability and Written Opinion of the International Search Authority for PCT/IL2012/000310 filed Aug. 21, 2012.

* cited by examiner

DEVICE AND METHOD FOR ASSISTING LAPAROSCOPIC SURGERY—RULE BASED APPROACH

CROSS-REFERENCE TO RELATED APPLICATIONS

This application is a Continuation of U.S. patent application Ser. No. 14/752,947, filed Jun. 28, 2015, which is a Division of U.S. patent application Ser. No. 14/150,939, which claims priority from U.S. Provisional Patent Application No. 61/750,856, filed Jan. 10, 2013, and is a Continuation-in-Part Application of International (PCT) Patent Application No. PCT/IL2012/000310, filed Aug. 21, 2012, which claims priority from U.S. Provisional Patent Application No. 61/525,779, filed Aug. 21, 2011, U.S. Provisional Patent Application No. 61/525,787, filed Aug. 21, 2011, and U.S. Provisional Patent Application No. 61/525,789, filed Aug. 21, 2011, all of which are incorporated by reference in their entirety.

FIELD OF THE INVENTION

The present invention generally relates to means and methods for improving the interface between the surgeon and the operating medical assistant or between the surgeon and an endoscope system for laparoscopic surgery. Moreover, the present invention discloses a device useful for spatially repositioning an endoscope to a specific region in the human body during surgery.

BACKGROUND OF THE INVENTION

In laparoscopic surgery, the surgeon performs the operation through small holes using long instruments and observing the internal anatomy with an endoscope camera. The endoscope is conventionally held by a human camera assistant (i.e. operating medical assistant) since the surgeon must perform the operation using both hands. The surgeon's performance is largely dependent on the camera position relative to the instruments and on a stable image shown by the monitor. The main problem is that it is difficult for the operating medical assistant to hold the endoscope steady, keeping the scene upright.

Laparoscopic surgery is becoming increasingly popular with patients because the scars are smaller and their period of recovery is shorter. Laparoscopic surgery requires special training for the surgeon or gynecologist and the theatre nursing staff. The equipment is often expensive and is not available in all hospitals.

During laparoscopic surgery, it is often required to shift the spatial placement of the endoscope in order to present the surgeon with an optimal view. Conventional laparoscopic surgery makes use of either human assistants that manually shift the instrumentation or, alternatively, robotic automated assistants. Automated assistants utilize interfaces that enable the surgeon to direct the mechanical movement of the assistant, achieving a shift in the camera view.

U.S. Pat. No. 6,714,841 discloses an automated camera endoscope in which the surgeon is fitted with a head mounted light source that transmits the head movements to a sensor, forming an interface that converts the movements to directions for the mechanical movement of the automated assistant. Alternative automated assistants incorporate a voice operated interface, a directional key interface, or other navigational interfaces. The above interfaces share the following drawbacks:

a. A single directional interface that provide limited feedback to the surgeon.
b. A cumbersome serial operation for starting and stopping movement directions that requires the surgeon's constant attention, preventing the surgeon from keeping the flow of the surgical procedure.

Research has suggested that these systems divert the surgeon's focus from the major task at hand. Therefore, technologies assisted by magnets and image processing have been developed to simplify interfacing control. However, these improved technologies still fail to address another complicating interface aspect of laparoscopic surgery, in that they do not allow the surgeon to signal, to automated assistants or to human assistants or to surgical colleagues, which instrument his attention is focused on.

Hence, there is still a long felt need for a improving the interface between the surgeon and an endoscope system, surgical colleagues or human assistants for laparoscopic surgery.

SUMMARY OF THE INVENTION

It is one object of the present invention to provide a surgical controlling system, comprising:
a. at least one surgical tool adapted to be inserted into a surgical environment of a human body for assisting a surgical procedure;
b. at least one location estimating means adapted to real rime locate the 3D spatial position of the at least one surgical tool at any given time t;
c. at least one movement detection means communicable with a movement's database and with said location estimating means; said movement's database is adapted to store said 3D spatial position of said at least one surgical tool at time $t_f$ and at time $t_o$; where $t_f > t_o$; said movement detection means is adapted to detect movement of said at least one surgical tool if the 3D spatial position of said at least one surgical tool at time $t_f$ is different than said 3D spatial position of said at least one surgical tool at time $t_o$; and,
d. a controller having a processing means communicable with a controller's database, the controller adapted to control the spatial position of the at least one surgical tool; said controller's database is in communication with said movement detection means;
wherein the controller's database is adapted to store a predetermined set of rules according to which ALLOWED and RESTRICTED movements of the at least one surgical tool are determined, such that each detected movement by said movement detection means of said at least one surgical tool is determined as either an ALLOWED movement or as a RESTRICTED movement according to said predetermined set of rules.

It is another object of the present invention to provide the surgical controlling system as defined above, wherein the predetermined set of rules comprises at least one rule selected from a group consisting of: most used tool rule, right tool rule, left tool rule, field of view rule, no fly zone rule, route rule, environmental rule, operator input rule, proximity rule; collision prevention rule, history-based rule, tool-dependent allowed and RESTRICTED movements rule, preferred volume zone rule, preferred tool rule, a movement detection rule, tagged tool rule, change of speed rule and any combination thereof.

It is another object of the present invention to provide the surgical controlling system as defined above, wherein the route rule comprises a communicable database storing predefined route in which the at least one surgical tool is adapted to move within the surgical environment; the predefined route comprises n 3D spatial positions of the at least one surgical tool; n is an integer greater than or equals to 2; the ALLOWED movements are movements in which the at least one surgical tool is located substantially in at least one of the n 3D spatial positions of the predefined route, and the RESTRICTED movements are movements in which the location of the at least one surgical tool is substantially different from the n 3D spatial positions of the predefined route.

It is another object of the present invention to provide the surgical controlling system as defined above, wherein the environmental rule comprises a comprises a communicable database; the communicable database is adapted to received real-time image of the surgical environment and is adapted to perform real-time image processing of the same and to determine the 3D spatial position of hazards or obstacles in the surgical environment; the environmental rule is adapted to determine the ALLOWED and RESTRICTED movements according to the hazards or obstacles in the surgical environment, such that the RESTRICTED movements are movements in which the at least one surgical tool is located substantially in at least one of the 3D spatial positions, and the ALLOWED movements are movements in which the location of the at least one surgical tool is substantially different from the 3D spatial positions.

It is another object of the present invention to provide the surgical controlling system as defined above, wherein the hazards or obstacles in the surgical environment are selected from a group consisting of tissue, a surgical tool, an organ, an endoscope and any combination thereof.

It is another object of the present invention to provide the surgical controlling system as defined above, wherein the operator input rule comprises a communicable database; the communicable database is adapted to receive an input from the operator of the system regarding the ALLOWED and RESTRICTED movements of the at least one surgical tool.

It is another object of the present invention to provide the surgical controlling system as defined above, wherein the input comprises n 3D spatial positions; n is an integer greater than or equals to 2; wherein at least one of which is defined as ALLOWED location and at least one of which is defined as RESTRICTED location, such that the ALLOWED movements are movements in which the at least one surgical tool is located substantially in at least one of the n 3D spatial positions, and the RESTRICTED movements are movements in which the location of the at least one surgical tool is substantially different from the n 3D spatial positions.

It is another object of the present invention to provide the surgical controlling system as defined above, wherein the input comprises at least one rule according to which ALLOWED and RESTRICTED movements of the at least one surgical tool are determined, such that the spatial position of the at least one surgical tool is controlled by the controller according to the ALLOWED and RESTRICTED movements.

It is another object of the present invention to provide the surgical controlling system as defined above, wherein the predetermined set of rules comprises at least one rule selected from the group consisting of: most used tool, right tool rule, left tool rule, field of view rule, no fly zone rule, a route rule, an environmental rule, an operator input rule, a proximity rule; a collision prevention rule, preferred volume zone rule, movement detection rule, a history based rule, a tool-dependent allowed and RESTRICTED movements rule, and any combination thereof.

It is another object of the present invention to provide the surgical controlling system as defined above, wherein the operator input rule converts an ALLOWED movement to a RESTRICTED movement and a RESTRICTED movement to an ALLOWED movement.

It is another object of the present invention to provide the surgical controlling system as defined above, wherein the proximity rule is adapted to define a predetermined distance between at least two surgical tools; the ALLOWED movements are movements which are within the range or out of the range of the predetermined distance, and the RESTRICTED movements which are out of the range or within the range of the predetermined distance.

It is another object of the present invention to provide the surgical controlling system as defined above, wherein the proximity rule is adapted to define a predetermined angle between at least three surgical tools; the ALLOWED movements are movements which are within the range or out of the range of the predetermined angle, and the RESTRICTED movements which are out of the range or within the range of the predetermined angle.

It is another object of the present invention to provide the surgical controlling system as defined above, wherein the collision prevention rule is adapted to define a predetermined distance between the at least one surgical tool and an anatomical element within the surgical environment; the ALLOWED movements are movements which are in a range that is larger than the predetermined distance, and the RESTRICTED movements are movements which is in a range that is smaller than the predetermined distance.

It is another object of the present invention to provide the surgical controlling system as defined above, wherein the anatomical element is selected from a group consisting of tissue, organ, another surgical tool or any combination thereof.

It is another object of the present invention to provide the surgical controlling system as defined above, wherein at least one of the following is being held true (a) said system additionally comprising an endoscope; said endoscope is adapted to provide real-time image of said surgical environment; (b) at least one of said surgical tools is an endoscope adapted to provide real-time image of said surgical environment.

It is another object of the present invention to provide the surgical controlling system as defined above, wherein the right tool rule is adapted to determine the ALLOWED movement of the endoscope according to the movement of the surgical tool positioned to right of the endoscope.

It is another object of the present invention to provide the surgical controlling system as defined above, wherein the left tool rule is adapted to determine the ALLOWED movement of the endoscope according to the movement of the surgical tool positioned to left of the endoscope.

It is another object of the present invention to provide the surgical controlling system as defined above, said a tagged tool rule comprises means adapted to tag at least one surgical tool within said surgical environment and to determine said ALLOWED movement of said endoscope according to the movement of said tagged surgical tool.

It is another object of the present invention to provide the surgical controlling system as defined above, wherein the field of view rule comprises a communicable database comprising n 3D spatial positions; n is an integer greater than or equals to 2; the combination of all of the n 3D spatial positions provides a predetermined field of view; the field of view rule is adapted to determine the ALLOWED movement of the endoscope within the n 3D spatial positions so as to maintain a constant field of view, such that the ALLOWED movements are movements in which the endoscope is located substantially in at least one of the n 3D spatial positions, and the RESTRICTED movements are movements in which the location of the endoscope is substantially different from the n 3D spatial positions.

It is another object of the present invention to provide the surgical controlling system as defined above, wherein the preferred volume zone rule comprises a communicable database comprising n 3D spatial positions; n is an integer greater than or equals to 2; the n 3D spatial positions provides the preferred volume zone; the preferred volume zone rule is adapted to determine the ALLOWED movement of the endoscope within the n 3D spatial positions and RESTRICTED movement of the endoscope outside the n 3D spatial positions, such that the ALLOWED movements are movements in which the endoscope is located substantially in at least one of the n 3D spatial positions, and the RESTRICTED movements are movements in which the location of the endoscope is substantially different from the n 3D spatial positions.

It is another object of the present invention to provide the surgical controlling system as defined above, wherein the preferred tool rule comprises a communicable database, the database stores a preferred tool; the preferred tool rule is adapted to determine the ALLOWED movement of the endoscope according to the movement of the preferred tool.

It is another object of the present invention to provide the surgical controlling system as defined above, wherein the no fly zone rule comprises a communicable database comprising n 3D spatial positions; n is an integer greater than or equals to 2; the n 3D spatial positions define a predetermined volume within the surgical environment; the no fly zone rule is adapted to determine the RESTRICTED movement if the movement is within the no fly zone and the ALLOWED movement if the movement is outside the no fly zone, such that the RESTRICTED movements are movements in which the at least one of the surgical tool is located substantially in at least one of the n 3D spatial positions, and the ALLOWED movements are movements in which the location of the at least one surgical tool is substantially different from the n 3D spatial positions.

It is another object of the present invention to provide the surgical controlling system as defined above, wherein the most used tool rule comprises a communicable database counting the amount of movement of each of the surgical tools; the most used tool rule is adapted to constantly position the endoscope to track the movement of the most moved surgical tool.

It is another object of the present invention to provide the surgical controlling system as defined above, wherein said system further comprising a maneuvering subsystem communicable with said controller, said maneuvering subsystem is adapted to spatially reposition said at least one surgical tool during a surgery according to said predetermined set of rules; further wherein the system is adapted to alert the physician of a RESTRICTED movements of the at least one surgical tool.

It is another object of the present invention to provide the surgical controlling system as defined above, wherein the alert is selected from a group consisting of audio signaling, voice signaling, light signaling, flashing signaling and any combination thereof.

It is another object of the present invention to provide the surgical controlling system as defined above, wherein the ALLOWED movement is permitted by the controller and a RESTRICTED movement is denied by the controller.

It is another object of the present invention to provide the surgical controlling system as defined above, wherein the history based rule comprises a communicable database storing each 3D spatial position of each of the surgical tool, such that each movement of each surgical tool is stored; the history based rule is adapted to determine the ALLOWED and RESTRICTED movements according to historical movements of the at least one surgical tool, such that the ALLOWED movements are movements in which the at least one surgical tool is located substantially in at least one of the 3D spatial positions, and the RESTRICTED movements are movements in which the location of the at least one surgical tool is substantially different from the n 3D spatial positions.

It is another object of the present invention to provide the surgical controlling system as defined above, wherein the tool-dependent allowed and RESTRICTED movements rule comprises a communicable database; the communicable database is adapted to store predetermined characteristics of at least one of the surgical tool; the tool-dependent allowed and RESTRICTED movements rule is adapted to determine the ALLOWED and RESTRICTED movements according to the predetermined characteristics of the surgical tool.

It is another object of the present invention to provide the surgical controlling system as defined above, wherein the predetermined characteristics of the surgical tool are selected from the group consisting of: physical dimensions, structure, weight, sharpness, and any combination thereof.

It is another object of the present invention to provide the surgical controlling system as defined above, wherein the movement detection rule comprises a communicable database comprising the real-time 3D spatial positions of each of the surgical tool; and to detect movement of the at least one surgical tool when a change in the 3D spatial positions is received, such that the ALLOWED movements are movements in which the endoscope is directed to focus on the moving surgical tool.

It is another object of the present invention to provide the surgical controlling system as defined above, further comprising a maneuvering subsystem communicable with the controller, the maneuvering subsystem is adapted to spatially reposition the at least one surgical tool during a surgery according to the predetermined set of rules, such that if said movement of said at least one surgical tool is a RESTRICTED movement, said maneuvering subsystem prevents said movement.

It is another object of the present invention to provide the surgical controlling system as defined above, wherein the at least one location estimating means comprises at least one endoscope adapted to acquire real-time images of the surgical environment within the human; and at least one surgical instrument spatial location software adapted to receive said real-time images of said surgical environment and to estimate said 3D spatial position of said at least one surgical tool.

It is another object of the present invention to provide the surgical controlling system as defined above, wherein the at least one location estimating means are comprises (a) at least one element selected from a group consisting of optical imaging means, radio frequency transmitting and receiving means, at least one mark on the at least one surgical tool and any combination thereof; and, (b) at least one surgical instrument spatial location software adapted to estimate said 3D spatial position of said at least one surgical tool by means of said element.

It is another object of the present invention to provide the surgical controlling system as defined above, wherein the at least one location estimating means are an interface subsystem between a surgeon and the at least one surgical tool, the interface subsystem comprises:

a. at least one array comprising N regular or pattern light sources, where N is a positive integer;
b. at least one array comprising M cameras, each of the M cameras, where M is a positive integer;
c. optional optical markers and means for attaching the optical marker to the at least one surgical tool; and;
d. a computerized algorithm operable via the controller, the computerized algorithm adapted to record images received by each camera of each of the M cameras and to calculate therefrom the position of each of the tools, and further adapted to provide automatically the results of the calculation to the human operator of the interface.

It is another object of the present invention to provide a method for assisting an operator to perform a surgical procedure, comprising steps of:

a. providing a surgical controlling system, comprising: (i) at least one surgical tool; (ii) at least one location estimating means; (iii) at least one movement detection means; and, (iv) a controller having a processing means communicable with a controller's database;
b. inserting the at least one surgical tool into a surgical environment of a human body;
c. real-time estimating the location of the at least one surgical tool within the surgical environment at any given time t; and,
d. detecting if there is movement of said at least one surgical tool if the 3D spatial position of said at least one surgical tool at time $t_f$ is different than said 3D spatial position of said at least one surgical tool at time $t_o$;
e. controlling the spatial position of the at least one surgical tool within the surgical environment by means of the controller;

wherein the step of controlling is performed by storing a predetermined set of rules in a controller's database; said predetermined set of rules comprises ALLOWED and RESTRICTED movements of the at least one surgical tool, such that each detected movement by said movement detection means of said at least one surgical tool is determined as either an ALLOWED movement or as a RESTRICTED movement according to said predetermined set of rules.

It is another object of the present invention to provide the method as defined above, further comprising a step of selecting the predetermined set of rules from the group consisting of: most used tool, right tool rule, left tool rule, field of view rule, no fly zone rule, a route rule, an environmental rule, an operator input rule, a proximity rule; a collision prevention rule, preferred volume zone rule, preferred tool rule, movement detection rule, a history based rule, a tool-dependent allowed and RESTRICTED movements rule, tagged tool rule and any combination thereof.

It is another object of the present invention to provide the method as defined above, wherein the route rule comprises a communicable database storing predefined route in which the at least one surgical tool is adapted to move within the surgical environment; the predefined route comprises n 3D spatial positions of the at least one surgical tool; n is an integer greater than or equals to 2; the ALLOWED movements are movements in which the at least one surgical tool is located substantially in at least one of the n 3D spatial positions of the predefined route, and the RESTRICTED movements are movements in which the location of the at least one surgical tool is substantially different from the n 3D spatial positions of the predefined route.

It is another object of the present invention to provide the method as defined above, wherein the environmental rule comprises a comprises a communicable database; the communicable database is adapted to received real-time image of the surgical environment and is adapted to perform real-time image processing of the same and to determine the 3D spatial position of hazards or obstacles in the surgical environment; the environmental rule is adapted to determine the ALLOWED and RESTRICTED movements according to the hazards or obstacles in the surgical environment, such that the RESTRICTED movements are movements in which the at least one surgical tool is located substantially in at least one of the 3D spatial positions, and the ALLOWED movements are movements in which the location of the at least one surgical tool is substantially different from the 3D spatial positions.

It is another object of the present invention to provide the method as defined above, wherein the hazards or obstacles in the surgical environment are selected from a group consisting of tissue, a surgical tool, an organ, an endoscope and any combination thereof.

It is another object of the present invention to provide the method as defined above, wherein the operator input rule comprises a communicable database; the communicable database is adapted to receive an input from the operator of the system regarding the ALLOWED and RESTRICTED movements of the at least one surgical tool.

It is another object of the present invention to provide the method as defined above, wherein the input comprises n 3D spatial positions; n is an integer greater than or equals to 2; wherein at least one of which is defined as ALLOWED location and at least one of which is defined as RESTRICTED location, such that the ALLOWED movements are movements in which the at least one surgical tool is located substantially in at least one of the n 3D spatial positions, and the RESTRICTED movements are movements in which the location of the at least one surgical tool is substantially different from the n 3D spatial positions.

It is another object of the present invention to provide the method as defined above, wherein the input comprises at least one predetermined rule according to which ALLOWED and RESTRICTED movements of the at least one surgical tool are determined, such that the spatial position of the at least one surgical tool is controlled by the controller according to the ALLOWED and RESTRICTED movements.

It is another object of the present invention to provide the method as defined above, wherein the predetermined rules is selected from the group consisting of: most used tool, right tool rule, left tool rule, field of view rule, no fly zone rule, preferred volume zone rule, a route rule, an environmental rule, an operator input rule, a proximity rule; a collision prevention rule, a history based rule, a tool-dependent allowed and RESTRICTED movements rule, and any combination thereof It is another object of the present invention to provide the method as defined above, wherein the operator input rule converts an ALLOWED movement to a RESTRICTED movement and a RESTRICTED movement to an ALLOWED movement.

It is another object of the present invention to provide the method as defined above, wherein the proximity rule is adapted to define a predetermined distance between at least two surgical tools; the ALLOWED movements are movements which are within the range or out of the range of the predetermined distance, and the RESTRICTED movements which are out of the range or within the range of the predetermined distance.

It is another object of the present invention to provide the method as defined above, wherein the proximity rule is adapted to define a predetermined angle between at least three surgical tools; the ALLOWED movements are movements which are within the range or out of the range of the predetermined angle, and the RESTRICTED movements which are out of the range or within the range of the predetermined angle It is another object of the present invention to provide the method as defined above, wherein the collision prevention rule is adapted to define a predetermined distance between the at least one surgical tool and an anatomical element within the surgical environment; the ALLOWED movements are movements which are in a range that is larger than the predetermined distance, and the RESTRICTED movements are movements which is in a range that is smaller than the predetermined distance.

It is another object of the present invention to provide the method as defined above, wherein the anatomical element is selected from a group consisting of tissue, organ, another surgical tool or any combination thereof.

It is another object of the present invention to provide the method as defined above, wherein at least one of the following is being held true (a) said system additionally comprising an endoscope; said endoscope is adapted to provide real-time image of said surgical environment; (b) at least one of said surgical tools is an endoscope adapted to provide real-time image of said surgical environment.

It is another object of the present invention to provide the method as defined above, wherein the right tool rule is adapted to determine the ALLOWED movement of the endoscope according to the movement of the surgical tool positioned to right of the endoscope.

It is another object of the present invention to provide the method as defined above, wherein the left tool rule is adapted to determine the ALLOWED movement of the endoscope according to the movement of the surgical tool positioned to left of the endoscope.

It is another object of the present invention to provide the method as defined above, wherein said a tagged tool rule comprises means adapted to tag at least one surgical tool within said surgical environment and to determine said ALLOWED movement of said endoscope according to the movement of said tagged surgical tool.

It is another object of the present invention to provide the method as defined above, wherein the field of view rule comprises n 3D spatial positions; n is an integer greater than or equals to 2; the combination of all of the n 3D spatial positions provides a predetermined field of view; the field of view rule is adapted to determine the ALLOWED movement of the endoscope within the n 3D spatial positions so as to maintain a constant field of view, such that the ALLOWED movements are movements in which the endoscope is located substantially in at least one of the n 3D spatial positions, and the RESTRICTED movements are movements in which the location of the endoscope is substantially different from the n 3D spatial positions.

It is another object of the present invention to provide the method as defined above, wherein the preferred volume zone rule comprises a communicable database comprising n 3D spatial positions; n is an integer greater than or equals to 2; the n 3D spatial positions provides the preferred volume zone; the preferred volume zone rule is adapted to determine the ALLOWED movement of the endoscope within the n 3D spatial positions and RESTRICTED movement of the endoscope outside the n 3D spatial positions, such that the ALLOWED movements are movements in which the endoscope is located substantially in at least one of the n 3D spatial positions, and the RESTRICTED movements are movements in which the location of the endoscope is substantially different from the n 3D spatial positions.

It is another object of the present invention to provide the method as defined above, wherein the preferred tool rule comprises a communicable database, the database stores a preferred tool; the preferred tool rule is adapted to determine the ALLOWED movement of the endoscope according to the movement of the preferred tool.

It is another object of the present invention to provide the method as defined above, wherein the no fly zone rule comprises n 3D spatial positions; n is an integer greater than or equals to 2; the n 3D spatial positions define a predetermined volume within the surgical environment; the no fly zone rule is adapted to determine the RESTRICTED movement if the movement is within the no fly zone and the ALLOWED movement if the movement is outside the no fly zone, such that the RESTRICTED movements are movements in which the at least one of the surgical tool is located substantially in at least one of the n 3D spatial positions, and the ALLOWED movements are movements in which the location of the at least one surgical tool is substantially different from the n 3D spatial positions.

It is another object of the present invention to provide the method as defined above, wherein the most used tool rule comprises a database counting the amount of movement of each of the surgical tools; the most used tool rule is adapted to constantly position the endoscope to track the movement of the most moved surgical tool.

It is another object of the present invention to provide the method as defined above, additionally comprising step of alerting the physician of a RESTRICTED movements of the at least one surgical tool.

It is another object of the present invention to provide the method as defined above, wherein the step of alerting is performed by at least one selected from a group consisting of audio signaling, voice signaling, light signaling, flashing signaling and any combination thereof.

It is another object of the present invention to provide the method as defined above, wherein the ALLOWED movement is permitted by the controller and a RESTRICTED movement is denied by the controller.

It is another object of the present invention to provide the method as defined above, wherein the history based rule comprises a communicable database storing each 3D spatial position of each of the surgical tool, such that each movement of each surgical tool is stored; the history based rule is adapted to determine the ALLOWED and RESTRICTED movements according to historical movements of the at least one surgical tool, such that the ALLOWED movements are movements in which the at least one surgical tool is located substantially in at least one of the 3D spatial positions, and the RESTRICTED movements are movements in which the location of the at least one surgical tool is substantially different from the n 3D spatial positions.

It is another object of the present invention to provide the method as defined above, wherein the tool-dependent allowed and RESTRICTED movements rule comprises a communicable database; the communicable database is adapted to store predetermined characteristics of at least one of the surgical tool; the tool-dependent allowed and RESTRICTED movements rule is adapted to determine the ALLOWED and RESTRICTED movements according to the predetermined characteristics of the surgical tool.

It is another object of the present invention to provide the method as defined above, wherein the predetermined characteristics of the surgical tool are selected from the group consisting of: physical dimensions, structure, weight, sharpness, and any combination thereof.

It is another object of the present invention to provide the method as defined above, wherein the movement detection rule comprises a communicable database comprising the real-time 3D spatial positions of each of the surgical tool; and to detect movement of the at least one surgical tool when a change in the 3D spatial positions is received, such that the ALLOWED movements are movements in which the endoscope is directed to focus on the moving surgical tool.

It is another object of the present invention to provide the method as defined above, further comprising a step of providing a maneuvering subsystem communicable with the controller, the maneuvering subsystem is adapted to spatially reposition the at least one surgical tool during a surgery according to the predetermined set of rules.

It is another object of the present invention to provide the method as defined above, wherein the at least one location estimating means comprises at least one endoscope adapted to acquire real-time images of a surgical environment within the human body; and at least one surgical instrument spatial location software adapted to receive said real-time images of said surgical environment and to estimate said 3D spatial position of said at least one surgical tool.

It is another object of the present invention to provide the method as defined above, wherein the at least one location estimating means are comprises (a) at least one element selected from a group consisting of optical imaging means, radio frequency transmitting and receiving means, at least one mark on the at least one surgical tool and any combination thereof; and, (b) at least one surgical instrument spatial location software adapted to estimate said 3D spatial position of said at least one surgical tool by means of said element.

It is another object of the present invention to provide the method as defined above, wherein the at least one location estimating means are an interface subsystem between a surgeon and the at least one surgical tool, the interface subsystem comprises:
  a. at least one array comprising N regular or pattern light sources, where N is a positive integer;
  b. at least one array comprising M cameras, each of the M cameras, where M is a positive integer;
  c. optional optical markers and means for attaching the optical marker to the at least one surgical tool; and,
  d. a computerized algorithm operable via the controller, the computerized algorithm adapted to record images received by each camera of each of the M cameras and to calculate therefrom the position of each of the tools, and further adapted to provide automatically the results of the calculation to the human operator of the interface.

It is another object of the present invention to provide a surgical tracking system for assisting an operator to perform a laparoscopic surgery of a human body, the surgical tracking system comprising:
  a. at least one endoscope adapted to acquire real-time images of a surgical environment within the human body;
  b. a maneuvering subsystem adapted to control the spatial position of the endoscope during the laparoscopic surgery; and,
  c. a tracking subsystem in communication with the maneuvering subsystem, adapted to control the maneuvering system so as to direct and modify the spatial position of the endoscope to a region of interest;
  wherein the tracking subsystem comprises a data processor; the data processor is adapted to perform real-time image processing of the surgical environment and to instruct the maneuvering subsystem to modify the spatial position of the endoscope according to input received from a maneuvering function f(t); the maneuvering function f(t) is adapted to (a) receive input from at least two instructing functions $g_i(t)$, where i is 1, . . . , n and n≥2; where t is time; i and n are integers; and, to (b) output instructions to the maneuvering subsystem based on the input from the at least two instructing functions $g_i(t)$, so as to spatially position the endoscope to the region of interest.

It is another object of the present invention to provide the surgical tracking system as defined above, wherein each of the instructing functions $g_i(t)$ is provided with $\alpha_i(t)$ where i is an integer greater than or equals to 1; where $\alpha_i(t)$ are weighting functions of each $g_i(t)$, and a n is total number of instruction functions.

It is another object of the present invention to provide the surgical tracking system as defined above, wherein each of the instructing functions $g_i(t)$ is selected from a group consisting of: most used tool function, a right tool function, left tool function, field of view function, preferred volume zone function, preferred tool function, no fly zone function, a tool detection function, a movement detection function, an organ detection function, a collision detection function, an operator input function, a prediction function, a past statistical analysis function, proximity function, a tagged tool function, and any combination thereof.

It is another object of the present invention to provide the surgical tracking system as defined above, wherein the weighting functions $\alpha_i(t)$ are time-varying functions, wherein the value of which is determined by the operators.

It is another object of the present invention to provide the surgical tracking system as defined above, wherein the tool detection function is adapted to detect surgical tools in the surgical environment and to output instruction to the tracking subsystem to instruct the maneuvering system to direct the endoscope on the detected surgical tools.

It is another object of the present invention to provide the surgical tracking system as defined above, wherein the movement detection function comprises a communicable database comprising the real-time 3D spatial positions of each of the surgical tool in the surgical environment; and to detect movement of the at least one surgical tool when a change in the 3D spatial positions is received, and to output instructions to the tracking subsystem to instruct the maneuvering system to direct the endoscope on the moved surgical tool.

It is another object of the present invention to provide the surgical tracking system as defined above, wherein the organ detection function is adapted to detect organs in the surgical environment and to output instructions to the tracking subsystem to instruct the maneuvering system to direct the endoscope on the detected organs.

It is another object of the present invention to provide the surgical tracking system as defined above, wherein the right tool function is adapted to detect surgical tool positioned to right of the endoscope and to output instructions to the tracking subsystem to instruct the maneuvering system to constantly direct the endoscope on the right tool and to track the right tool.

It is another object of the present invention to provide the surgical tracking system as defined above, wherein the left tool function is adapted to detect surgical tool positioned to left of the endoscope and to output instructions to the tracking subsystem to instruct the maneuvering system to constantly direct the endoscope on the left tool and to track the left tool.

It is another object of the present invention to provide the surgical tracking system as defined above, wherein the operator input function comprises a communicable database; the communicable database is adapted to receive an input from the operator of the system; the input comprising n 3D spatial positions; n is an integer greater than or equals to 2; and to output instructions to the tracking subsystem to instruct the maneuvering system to direct the endoscope to the at least one 3D spatial position received.

It is another object of the present invention to provide the surgical tracking system as defined above, wherein the proximity function is adapted to define a predetermined distance between at least two surgical tools; and to output instructions to the tracking subsystem to instruct the maneuvering system to direct the endoscope to the two surgical tools if the distance between the two surgical tools is less than the predetermined distance.

It is another object of the present invention to provide the surgical tracking system as defined above, wherein the proximity function is adapted to define a predetermined angle between at least three surgical tools; and to output instructions to the tracking subsystem to instruct the maneuvering system to direct the endoscope to the three surgical tools if the angle between the two surgical tools is less than or greater than the predetermined angle.

It is another object of the present invention to provide the surgical tracking system as defined above, wherein the preferred volume zone function comprises communicable database comprising n 3D spatial positions; n is an integer greater than or equals to 2; the n 3D spatial positions provides the preferred volume zone; the preferred volume zone function is adapted to output instructions to the tracking subsystem to instruct the maneuvering system to direct the endoscope to the preferred volume zone.

It is another object of the present invention to provide the surgical tracking system as defined above, wherein the preferred tool function comprises a communicable database, the database stores a preferred tool; the preferred tool function is adapted to output instructions to the tracking subsystem to instruct the maneuvering system to direct the endoscope to the preferred tool.

It is another object of the present invention to provide the surgical tracking system as defined above, wherein the collision prevention function is adapted to define a predetermined distance between the at least one surgical tool and an anatomical element within the surgical environment; and to output instructions to the tracking subsystem to instruct the maneuvering system to direct the endoscope to the surgical tool and the anatomical element within the surgical environment if the distance between the at least one surgical tool and an anatomical element is less than the predetermined distance.

It is another object of the present invention to provide the surgical tracking system as defined above, wherein the anatomical element is selected from a group consisting of tissue, organ, another surgical tool or any combination thereof.

It is another object of the present invention to provide the surgical tracking system as defined above, wherein the field of view function comprises a communicable database comprising n 3D spatial positions; n is an integer greater than or equals to 2; the combination of all of the n 3D spatial positions provides a predetermined field of view; the field of view function is adapted to output instructions to the tracking subsystem to instruct the maneuvering system to direct the endoscope to at least one 3D spatial position substantially within the n 3D spatial positions so as to maintain a constant field of view.

It is another object of the present invention to provide the surgical tracking system as defined above, wherein the no fly zone function comprises a communicable database comprising n 3D spatial positions; n is an integer greater than or equals to 2; the n 3D spatial positions define a predetermined volume within the surgical environment; the no fly zone function is adapted to output instructions to the tracking subsystem to instruct the maneuvering system to direct the endoscope to at least one 3D spatial position substantially different from all the n 3D spatial positions.

It is another object of the present invention to provide the surgical tracking system as defined above, wherein the most used tool function comprises a communicable database counting the amount of movement of each surgical tool located within the surgical environment; the most used tool function is adapted to output instructions to the tracking subsystem to instruct the maneuvering system to direct the endoscope to constantly position the endoscope to track the movement of the most moved surgical tool.

It is another object of the present invention to provide the surgical tracking system as defined above, wherein the prediction function comprises a communicable database storing each 3D spatial position of each of surgical tool within the surgical environment, such that each movement of each surgical tool is stored; the prediction function is adapted to (a) to predict the future 3D spatial position of each of the surgical tools; and, (b) to output instructions to the tracking subsystem to instruct the maneuvering system to direct the endoscope to the future 3D spatial position.

It is another object of the present invention to provide the surgical tracking system as defined above, wherein the past statistical analysis function comprises a communicable database storing each 3D spatial position of each of surgical tool within the surgical environment, such that each movement of each surgical tool is stored; the past statistical analysis function is adapted to (a) statistical analyze the 3D spatial positions of each of the surgical tools; and, (b) to predict the future 3D spatial position of each of the surgical tools; and, (c) to output instructions to the tracking subsystem to instruct the maneuvering system to direct the endoscope to the future 3D spatial position.

It is another object of the present invention to provide the surgical tracking system as defined above, wherein the a tagged tool function comprises means adapted to tag at least one surgical tool within the surgical environment and to output instructions to the tracking subsystem to instruct the maneuvering system to constantly direct the endoscope to the tagged surgical tool.

It is another object of the present invention to provide the surgical tracking system as defined above, wherein the means are adapted to constantly tag the at least one of surgical tool within the surgical environment.

It is another object of the present invention to provide the surgical tracking system as defined above, wherein means are adapted to re-tag the at least one of the surgical tools until a desired tool is selected.

It is another object of the present invention to provide the surgical tracking system as defined above, additionally comprising means adapted to toggle the surgical tools.

It is another object of the present invention to provide the surgical tracking system as defined above, wherein the toggling is performed manually or automatically.

It is another object of the present invention to provide the surgical tracking system as defined above, wherein the image processing is obtained by at least one algorithm selected from the group consisting of: image stabilization algorithm, image improvement algorithm, image compilation algorithm, image enhancement algorithm, image detection algorithm, image classification algorithm, image correlation with the cardiac cycle or the respiratory cycle of the human body, smoke or vapor, steam reduction from the endoscope and any combination thereof.

It is another object of the present invention to provide the surgical tracking system as defined above, wherein the endoscope comprises an image acquisition device selected from the group consisting of: a camera, a video camera, an electromagnetic sensor, a computer tomography imaging device, a fluoroscopic imaging device, an ultrasound imaging device, and any combination thereof.

It is another object of the present invention to provide the surgical tracking system as defined above, further comprising a display adapted to provide input or output to the operator regarding the operation of the system.

It is another object of the present invention to provide the surgical tracking system as defined above, wherein the display is used for visualizing the region of interest by the operator.

It is another object of the present invention to provide the surgical tracking system as defined above, wherein the display is adapted to output the acquired real-time images of a surgical environment with augmented reality elements.

It is another object of the present invention to provide the surgical tracking system as defined above, wherein the image processing algorithm is adapted to analyze 2D or 3D representation rendered from the real-time images of the surgical environment.

It is another object of the present invention to provide the surgical tracking system as defined above, wherein the data processor is further adapted to operate a pattern recognition algorithm for assisting the operation of the instructing functions $g_i(t)$.

It is another object of the present invention to provide the surgical tracking system as defined above, additionally comprising at least one location estimating means for locating the position of at least one surgical tool in the surgical environment.

It is another object of the present invention to provide the surgical tracking system as defined above, wherein the at least one location estimating means are an interface subsystem between a surgeon and the at least one surgical tool, the interface subsystem comprises:
 a. at least one array comprising N regular or pattern light sources, where N is a positive integer;
 b. at least one array comprising M cameras, each of the M cameras, where M is a positive integer;
 c. optional optical markers and means for attaching the optical marker to the at least one surgical tool; and,
 d. a computerized algorithm operable via the controller, the computerized algorithm adapted to record images received by each camera of each of the M cameras and to calculate therefrom the position of each of the tools, and further adapted to provide automatically the results of the calculation to the human operator of the interface.

It is another object of the present invention to provide a method for assisting an operator to perform a laparoscopic surgery of a human body, the method comprising steps of:
 a. providing a surgical tracking system, comprising: (i) at least one endoscope adapted to acquire real-time images of a surgical environment within the human body; (ii) a maneuvering subsystem in communication with the endoscope; and, (iii) a tracking subsystem in communication with the maneuvering subsystem, the tracking subsystem comprises a data processor;
 b. performing real-time image processing of the surgical environment;
 c. controlling the maneuvering system via the tracking subsystem, thereby directing and modifying the spatial position of the endoscope to a region of interest according to input received from a maneuvering function f(t);
 wherein the maneuvering function f(t) is adapted to (a) receive input from at least two instructing functions $g_i(t)$, where i is 1, . . . , n and n≥2; where t is time; i and n are integers;
 and, to (b) output instructions to the maneuvering subsystem based on the input from the at least two instructing functions $g_i(t)$, so as to spatially position the endoscope to the region of interest.

It is another object of the present invention to provide the method as defined above, wherein each of the instructing functions $g_i(t)$ is provided with $\alpha_i(t)$ where i is an integer greater than or equals to 1; where $\alpha_i(t)$ are weighting functions of each $g_i(t)$, and a n is total number of instruction functions.

It is another object of the present invention to provide the method as defined above, wherein each of the instructing functions $g_i(t)$ is selected from a group consisting of: most used tool function, a right tool function, left tool function, field of view function, preferred volume zone function, preferred tool function, no fly zone function, a tool detection function, a movement detection function, an organ detection function, a collision detection function, an operator input function, a prediction function, a past statistical analysis function, proximity function, a tagged tool function, and any combination thereof.

It is another object of the present invention to provide the method as defined above, wherein the weighting functions $\alpha_i(t)$ are time-varying functions, wherein the value of which is determined by the operators.

It is another object of the present invention to provide the method as defined above, wherein the tool detection function is adapted to detect surgical tools in the surgical environment and to output instructions to the tracking subsystem to instruct the maneuvering system to direct the endoscope on the detected surgical tools.

It is another object of the present invention to provide the method as defined above, wherein the movement detection function comprises a communicable database comprising the real-time 3D spatial positions of each of the surgical tool in the surgical environment; and to detect movement of the at least one surgical tool when a change in the 3D spatial positions is received, and to output instructions to the tracking subsystem to instruct the maneuvering system to direct the endoscope on the moved surgical tool.

It is another object of the present invention to provide the method as defined above, wherein the organ detection function is adapted to detect organs in the surgical environment and to output instructions to the tracking subsystem to instruct the maneuvering system to direct the endoscope on the detected organs.

It is another object of the present invention to provide the method as defined above, wherein the right tool function is adapted to detect surgical tool positioned to right of the endoscope and to output instructions to the tracking subsystem to instruct the maneuvering system to constantly direct the endoscope on the right tool and to track the right tool.

It is another object of the present invention to provide the method as defined above, wherein the left tool function is adapted to detect surgical tool positioned to left of the endoscope and to output instructions to the tracking subsystem to instruct the maneuvering system to constantly direct the endoscope on the left tool and to track the left tool.

It is another object of the present invention to provide the method as defined above, wherein the operator input function comprises a communicable database; the communicable database is adapted to receive an input from the operator of the system; the input comprising n 3D spatial positions; n is an integer greater than or equals to 2; and to output instructions to the tracking subsystem to instruct the maneuvering system to direct the endoscope to the at least one 3D spatial position received.

It is another object of the present invention to provide the method as defined above, wherein the proximity function is adapted to define a predetermined distance between at least two surgical tools; and to output instructions to the tracking subsystem to instruct the maneuvering system to direct the endoscope to the two surgical tools if the distance between the two surgical tools is less than the predetermined distance.

It is another object of the present invention to provide the method as defined above, wherein the proximity function is adapted to define a predetermined angle between at least three surgical tools; and to output instructions to the tracking subsystem to instruct the maneuvering system to direct the endoscope to the three surgical tools if the angle between the two surgical tools is less than or greater than the predetermined angle.

It is another object of the present invention to provide the method as defined above, wherein the preferred volume zone function comprises communicable database comprising n 3D spatial positions; n is an integer greater than or equals to 2; the n 3D spatial positions provides the preferred volume zone; the preferred volume zone function is adapted to output instructions to the tracking subsystem to instruct the maneuvering system to direct the endoscope to the preferred volume zone.

It is another object of the present invention to provide the method as defined above, wherein the preferred tool function comprises a communicable database, the database stores a preferred tool; the preferred tool function is adapted to output instructions to the tracking subsystem to instruct the maneuvering system to direct the endoscope to the preferred tool.

It is another object of the present invention to provide the method as defined above, wherein the collision prevention function is adapted to define a predetermined distance between the at least one surgical tool and an anatomical element within the surgical environment; and to output instructions to the tracking subsystem to instruct the maneuvering system to direct the endoscope to the surgical tool and the anatomical element within the surgical environment if the distance between the at least one surgical tool and an anatomical element is less than the predetermined distance.

It is another object of the present invention to provide the method as defined above, wherein the anatomical element is selected from a group consisting of tissue, organ, another surgical tool or any combination thereof.

It is another object of the present invention to provide the method as defined above, wherein the field of view function comprises a communicable database comprising n 3D spatial positions; n is an integer greater than or equals to 2; the combination of all of the n 3D spatial positions provides a predetermined field of view; the field of view function is adapted to output instructions to the tracking subsystem to instruct the maneuvering system to direct the endoscope to at least one 3D spatial position substantially within the n 3D spatial positions so as to maintain a constant field of view.

It is another object of the present invention to provide the method as defined above, wherein the no fly zone function comprises a communicable database comprising n 3D spatial positions; n is an integer greater than or equals to 2; the n 3D spatial positions define a predetermined volume within the surgical environment; the no fly zone function is adapted to output instructions to the tracking subsystem to instruct the maneuvering system to direct the endoscope to at least one 3D spatial position substantially different from all the n 3D spatial positions.

It is another object of the present invention to provide the method as defined above, wherein the most used tool function comprises a communicable database counting the amount of movement of each surgical tool located within the surgical environment; the most used tool function is adapted to output instructions to the tracking subsystem to instruct the maneuvering system to direct the endoscope to constantly position the endoscope to track the movement of the most moved surgical tool.

It is another object of the present invention to provide the method as defined above, wherein the prediction function comprises a communicable database storing each 3D spatial position of each of surgical tool within the surgical environment, such that each movement of each surgical tool is stored; the prediction function is adapted to (a) to predict the future 3D spatial position of each of the surgical tools; and, (b) to output instructions to the tracking subsystem to instruct the maneuvering system to direct the endoscope to the future 3D spatial position.

It is another object of the present invention to provide the method as defined above, wherein the past statistical analysis function comprises a communicable database storing each 3D spatial position of each of surgical tool within the surgical environment, such that each movement of each surgical tool is stored; the past statistical analysis function is adapted to (a) statistical analyze the 3D spatial positions of each of the surgical tools; and, (b) to predict the future 3D spatial position of each of the surgical tools; and, (c) to output instructions to the tracking subsystem to instruct the maneuvering system to direct the endoscope to the future 3D spatial position.

It is another object of the present invention to provide the method as defined above, wherein the a tagged tool function comprises means adapted to tag at least one surgical tool within the surgical environment and to output instructions to the tracking subsystem to instruct the maneuvering system to constantly direct the endoscope to the tagged surgical tool.

It is another object of the present invention to provide the method as defined above, wherein the means are adapted to constantly tag the at least one of surgical tool within the surgical environment.

It is another object of the present invention to provide the method as defined above, wherein means are adapted to re-tag the at least one of the surgical tools until a desired tool is selected.

It is another object of the present invention to provide the method as defined above, additionally comprising step of providing means adapted to toggle the surgical tools.

It is another object of the present invention to provide the method as defined above, wherein the toggling is performed manually or automatically.

It is another object of the present invention to provide the method as defined above, wherein the image processing is obtained by at least one algorithm selected from the group consisting of: image stabilization algorithm, image improvement algorithm, image compilation algorithm, image enhancement algorithm, image detection algorithm, image classification algorithm, image correlation with the cardiac cycle or the respiratory cycle of the human body, smoke or vapor, steam reduction from the endoscope and any combination thereof.

It is another object of the present invention to provide the method as defined above, wherein the endoscope comprises an image acquisition device selected from the group consisting of: a camera, a video camera, an electromagnetic sensor, a computer tomography imaging device, a fluoroscopic imaging device, an ultrasound imaging device, and any combination thereof.

It is another object of the present invention to provide the method as defined above, further comprising step of providing a display adapted to provide input or output to the operator regarding the operation of the system.

It is another object of the present invention to provide the method as defined above, wherein the display is used for visualizing the region of interest by the operator.

It is another object of the present invention to provide the method as defined above, wherein the display is adapted to output the acquired real-time images of a surgical environment with augmented reality elements.

It is another object of the present invention to provide the method as defined above, wherein the image processing algorithm is adapted to analyze 2D or 3D representation rendered from the real-time images of the surgical environment.

It is another object of the present invention to provide the method as defined above, wherein the data processor is further adapted to operate a pattern recognition algorithm for assisting the operation of the instructing functions $g_i(t)$.

It is another object of the present invention to provide the method as defined above, additionally comprising step of preliminary tagging at least one of the surgical tools.

It is another object of the present invention to provide the method as defined above, additionally comprising step of constantly tagging at least one of the surgical tools.

It is another object of the present invention to provide the method as defined above, additionally comprising step of re-tagging the at least one of the surgical tools until a desired tool is selected.

It is another object of the present invention to provide the method as defined above, additionally comprising step of toggling the surgical tools.

It is another object of the present invention to provide the method as defined above, wherein the toggling is performed manually or automatically.

It is another object of the present invention to provide the method as defined above, additionally comprising step of locating the 3D position of at least one surgical tool in the surgical environment.

It is another object of the present invention to provide the method as defined above, wherein the step of locating the 3D position of at least one surgical tool is provided by at least one location estimating means; the at least one location estimating means are an interface subsystem between a surgeon and the at least one surgical tool, the interface subsystem comprises:
  a. at least one array comprising N regular or pattern light sources, where N is a positive integer;
  b. at least one array comprising M cameras, each of the M cameras, where M is a positive integer;
  c. optional optical markers and means for attaching the optical marker to the at least one surgical tool; and,
  d. a computerized algorithm operable via the controller, the computerized algorithm adapted to record images received by each camera of each of the M cameras and to calculate therefrom the position of each of the tools, and further adapted to provide automatically the results of the calculation to the human operator of the interface.

It is another object of the present invention to provide a surgical controlling system, comprising:
  a. at least one endoscope adapted to provide real-time image of surgical environment of a human body;
  b. at least one processing means, adapted to real time define n element within the real-time image of surgical environment of a human body; each of the elements is characterized by predetermined characteristics;
  c. image processing means in communication with the endoscope, adapted to image process the real-time image and to provide real time updates of the predetermined characteristics;
  d. a communicable database, in communication with the processing means and the image processing means, adapted to store the predetermined characteristics and the updated characteristics;
  wherein the system is adapted to notify if the updated characteristics are substantially different from the predetermined characteristics.

It is another object of the present invention to provide the surgical controlling system as defined above, wherein the predetermined characteristics are selected from a group consisting of color of the element, 3D spatial location of the element, contours of the element, and any combination thereof.

It is another object of the present invention to provide the surgical controlling system as defined above, additionally comprising at least one surgical tool adapted to be inserted into a surgical environment of a human body for assisting a surgical procedure.

It is another object of the present invention to provide the surgical controlling system as defined above, additionally comprising (a) at least one location estimating means adapted to real-time estimate the location of the at least one surgical tool at any given time t; and, (b) at least one movement detection means communicable with a movement's database and with said location estimating means; said movement's database is adapted to store said 3D spatial position of said at least one surgical tool at time $t_f$ and at time $t_0$; where $t_f > t_0$; said movement detection means is adapted to detect movement of said at least one surgical tool if the 3D spatial position of said at least one surgical tool at time $t_f$ is different than said 3D spatial position of said at least one surgical tool at time $t_o$.

It is another object of the present invention to provide the surgical controlling system as defined above, additionally comprising a controller having a processing means communicable with a controller's database, the controller adapted to control the spatial position of the at least one surgical tool.

It is another object of the present invention to provide the surgical controlling system as defined above, wherein the controller's database is adapted to store a predetermined set of rules according to which ALLOWED and RESTRICTED movements of the at least one surgical tool are determined, such that each detected movement by said movement detection means of said at least one surgical tool is determined as either an ALLOWED movement or as a RESTRICTED movement according to said predetermined set of rules.

It is another object of the present invention to provide the surgical controlling system as defined above, wherein the predetermined set of rules comprises at least one rule selected from the group consisting of: most used tool rule, right tool rule, left tool rule, field of view rule, no fly zone rule, route rule, environmental rule, operator input rule, proximity rule; collision prevention rule, history based rule, tool-dependent allowed and RESTRICTED movements rule, preferred volume zone rule, preferred tool rule, movement detection rule, and any combination thereof.

It is another object of the present invention to provide the surgical controlling system as defined above, wherein the route rule comprises a communicable database storing predefined route in which the at least one surgical tool is adapted to move within the surgical environment; the predefined route comprises n 3D spatial positions of the at least one surgical tool; n is an integer greater than or equals to 2; the ALLOWED movements are movements in which the at least one surgical tool is located substantially in at least one of the n 3D spatial positions of the predefined route, and the RESTRICTED movements are movements in which the location of the at least one surgical tool is substantially different from the n 3D spatial positions of the predefined route.

It is another object of the present invention to provide the surgical controlling system as defined above, wherein the environmental rule comprises a comprises a communicable database; the communicable database is adapted to received real-time image of the surgical environment and is adapted to perform real-time image processing of the same and to determined the 3D spatial position of hazards or obstacles in the surgical environment; the environmental rule is adapted to determine the ALLOWED and RESTRICTED movements according to the hazards or obstacles in the surgical environment, such that the RESTRICTED movements are movements in which the at least one surgical tool is located substantially in at least one of the 3D spatial positions, and the ALLOWED movements are movements in which the location of the at least one surgical tool is substantially different from the 3D spatial positions.

It is another object of the present invention to provide the surgical controlling system as defined above, wherein the hazards or obstacles in the surgical environment are selected from a group consisting of tissue, a surgical tool, an organ, an endoscope and any combination thereof.

It is another object of the present invention to provide the surgical controlling system as defined above, wherein the operator input rule comprises a communicable database; the communicable database is adapted to receive an input from the operator of the system regarding the ALLOWED and RESTRICTED movements of the at least one surgical tool.

It is another object of the present invention to provide the surgical controlling system as defined above, wherein the input comprises n 3D spatial positions; n is an integer greater than or equals to 2; wherein at least one of which is defined as ALLOWED location and at least one of which is defined as RESTRICTED location, such that the ALLOWED movements are movements in which the at least one surgical tool is located substantially in at least one of the n 3D spatial positions, and the RESTRICTED movements are movements in which the location of the at least one surgical tool is substantially different from the n 3D spatial positions.

It is another object of the present invention to provide the surgical controlling system as defined above, wherein the input comprises at least one rule according to which ALLOWED and RESTRICTED movements of the at least one surgical tool are determined, such that the spatial position of the at least one surgical tool is controlled by the controller according to the ALLOWED and RESTRICTED movements.

It is another object of the present invention to provide the surgical controlling system as defined above, wherein the predetermined set of rules comprises at least one rule selected from the group consisting of: most used tool, right tool rule, left tool rule, field of view rule, no fly zone rule, a route rule, an environmental rule, an operator input rule, a proximity rule; a collision prevention rule, preferred volume zone rule, movement detection rule, a history based rule, a tool-dependent allowed and RESTRICTED movements rule, and any combination thereof.

It is another object of the present invention to provide the surgical controlling system as defined above, wherein the operator input rule converts an ALLOWED movement to a RESTRICTED movement and a RESTRICTED movement to an ALLOWED movement.

It is another object of the present invention to provide the surgical controlling system as defined above, wherein the proximity rule is adapted to define a predetermined distance between at least two surgical tools; the ALLOWED movements are movements which are within the range or out of the range of the predetermined distance, and the RESTRICTED movements which are out of the range or within the range of the predetermined distance.

It is another object of the present invention to provide the surgical controlling system as defined above, wherein the proximity rule is adapted to define a predetermined angle between at least three surgical tools; the ALLOWED movements are movements which are within the range or out of the range of the predetermined angle, and the RESTRICTED movements which are out of the range or within the range of the predetermined angle.

It is another object of the present invention to provide the surgical controlling system as defined above, wherein the collision prevention rule is adapted to define a predetermined distance between the at least one surgical tool and an anatomical element within the surgical environment; the ALLOWED movements are movements which are in a range that is larger than the predetermined distance, and the RESTRICTED movements are movements which is in a range that is smaller than the predetermined distance.

It is another object of the present invention to provide the surgical controlling system as defined above, wherein the anatomical element is selected from a group consisting of tissue, organ, another surgical tool or any combination thereof.

It is another object of the present invention to provide the surgical controlling system as defined above, wherein at least one of the following is being held true (a) said system additionally comprising an endoscope; said endoscope is adapted to provide real-time image of said surgical environment; (b) at least one of said surgical tools is an endoscope adapted to provide real-time image of said surgical environment.

It is another object of the present invention to provide the surgical controlling system as defined above, wherein the right tool rule is adapted to determine the ALLOWED movement of the endoscope according to the movement of the surgical tool positioned to right of the endoscope.

It is another object of the present invention to provide the surgical controlling system as defined above, wherein the left tool rule is adapted to determine the ALLOWED movement of the endoscope according to the movement of the surgical tool positioned to left of the endoscope.

It is another object of the present invention to provide the surgical controlling system as defined above, wherein the field of view rule comprises a communicable database comprising n 3D spatial positions; n is an integer greater than or equals to 2; the combination of all of the n 3D spatial positions provides a predetermined field of view; the field of view rule is adapted to determine the ALLOWED movement of the endoscope within the n 3D spatial positions so as to maintain a constant field of view, such that the ALLOWED movements are movements in which the endoscope is located substantially in at least one of the n 3D spatial positions, and the RESTRICTED movements are movements in which the location of the endoscope is substantially different from the n 3D spatial positions.

It is another object of the present invention to provide the surgical controlling system as defined above, wherein the preferred volume zone rule comprises a communicable database comprising n 3D spatial positions; n is an integer greater than or equals to 2; the n 3D spatial positions provides the preferred volume zone; the preferred volume zone rule is adapted to determine the ALLOWED movement of the endoscope within the n 3D spatial positions and RESTRICTED movement of the endoscope outside the n 3D spatial positions, such that the ALLOWED movements are movements in which the endoscope is located substantially in at least one of the n 3D spatial positions, and the RESTRICTED movements are movements in which the location of the endoscope is substantially different from the n 3D spatial positions.

It is another object of the present invention to provide the surgical controlling system as defined above, wherein the preferred tool rule comprises a communicable database, the database stores a preferred tool; the preferred tool rule is adapted to determine the ALLOWED movement of the endoscope according to the movement of the preferred tool.

It is another object of the present invention to provide the surgical controlling system as defined above, wherein the no fly zone rule comprises a communicable database comprising n 3D spatial positions; n is an integer greater than or equals to 2; the n 3D spatial positions define a predetermined volume within the surgical environment; the no fly zone rule is adapted to determine the RESTRICTED movement if the movement is within the no fly zone and the ALLOWED movement if the movement is outside the no fly zone, such that the RESTRICTED movements are movements in which the at least one of the surgical tool is located substantially in at least one of the n 3D spatial positions, and the ALLOWED movements are movements in which the location of the at least one surgical tool is substantially different from the n 3D spatial positions.

It is another object of the present invention to provide the surgical controlling system as defined above, wherein the most used tool rule comprises a communicable database counting the amount of movement of each of the surgical tools; the most used tool rule is adapted to constantly position the endoscope to track the movement of the most moved surgical tool.

It is another object of the present invention to provide the surgical controlling system as defined above, wherein said system further comprising a maneuvering subsystem communicable with said controller, said maneuvering subsystem is adapted to spatially reposition said at least one surgical tool during a surgery according to said predetermined set of rules; further wherein the system is adapted to alert the physician of a RESTRICTED movements of the at least one surgical tool.

It is another object of the present invention to provide the surgical controlling system as defined above, wherein the alert is selected from a group consisting of audio signaling, voice signaling, light signaling, flashing signaling and any combination thereof.

It is another object of the present invention to provide the surgical controlling system as defined above, wherein the ALLOWED movement is permitted by the controller and a RESTRICTED movement is denied by the controller.

It is another object of the present invention to provide the surgical controlling system as defined above, wherein the history based rule comprises a communicable database storing each 3D spatial position of each of the surgical tool, such that each movement of each surgical tool is stored; the history based rule is adapted to determine the ALLOWED and RESTRICTED movements according to historical movements of the at least one surgical tool, such that the ALLOWED movements are movements in which the at least one surgical tool is located substantially in at least one of the 3D spatial positions, and the RESTRICTED movements are movements in which the location of the at least one surgical tool is substantially different from the n 3D spatial positions.

It is another object of the present invention to provide the surgical controlling system as defined above, wherein the tool-dependent allowed and RESTRICTED movements rule comprises a communicable database; the communicable database is adapted to store predetermined characteristics of at least one of the surgical tool; the tool-dependent allowed and RESTRICTED movements rule is adapted to determine the ALLOWED and RESTRICTED movements according to the predetermined characteristics of the surgical tool.

It is another object of the present invention to provide the surgical controlling system as defined above, wherein the predetermined characteristics of the surgical tool are selected from the group consisting of: physical dimensions, structure, weight, sharpness, and any combination thereof.

It is another object of the present invention to provide the surgical controlling system as defined above, wherein the movement detection rule comprises a communicable database comprising the real-time 3D spatial positions of each of the surgical tool; and to detect movement of the at least one surgical tool when a change in the 3D spatial positions is received, such that the ALLOWED movements are movements in which the endoscope is directed to focus on the moving surgical tool.

It is another object of the present invention to provide the surgical controlling system as defined above, further comprising a maneuvering subsystem communicable with the controller, the maneuvering subsystem is adapted to spatially reposition at least one surgical tool during a surgery according to the predetermined set of rules, such that if said movement of said at least one surgical tool is a RESTRICTED movement, said maneuvering subsystem prevents said movement.

It is another object of the present invention to provide the surgical controlling system as defined above, further comprising at least one location estimating means adapted to acquire real-time images of the surgical environment within the human body for the estimation of the 3D spatial position of at least one surgical tool.

It is another object of the present invention to provide the surgical controlling system as defined above, wherein the at least one location estimating means are comprises at least one selected from a group consisting of optical imaging means, radio frequency transmitting and receiving means, at least one mark on the at least one surgical tool and any combination thereof.

It is another object of the present invention to provide a method for controlling surgical surgery, comprising step of:
a. obtaining a system comprising:
   i. at least one endoscope adapted to provide real-time image of surgical environment of a human body;
   ii. at least one processing means, adapted to real time define n element within the real-time image of surgical environment of a human body; each of the elements is characterized by predetermined characteristics;
   iii. image processing means in communication with the endoscope, adapted to image process the real-time image and to provide real time updates of the predetermined characteristics;
   iv. a communicable database, in communication with the processing means and the image processing means, adapted to store the predetermined characteristics and the updated characteristics;
b. providing a real-time image of surgical environment of a human body;
c. defining the n element;
d. characterizing each of the element with predetermined characteristics;
e. providing a real-time update of the predetermined characteristics;
f. notifying the user if the updated characteristics are substantially different from the predetermined characteristics.

It is another object of the present invention to provide the method as defined above, wherein the predetermined characteristics are selected from a group consisting of color of the element, 3D spatial location of the element, contours of the element, and any combination thereof.

It is another object of the present invention to provide the method as defined above, additionally comprising at least one surgical tool adapted to be inserted into a surgical environment of a human body for assisting a surgical procedure.

It is another object of the present invention to provide the method as defined above, additionally comprising (a) at least one location estimating means adapted to real-time estimate the location of the at least one surgical tool at any given time t; and, (b) at least one movement detection means communicable with a movement's database and with said location estimating means; said movement's database is adapted to store said 3D spatial position of said at least one surgical tool at time $t_f$ and at time $t_0$; where $t_f > t_0$; said movement detection means is adapted to detect movement of said at least one surgical tool if the 3D spatial position of said at least one surgical tool at time $t_f$ is different than said 3D spatial position of said at least one surgical tool at time $t_0$.

It is another object of the present invention to provide the method as defined above, additionally comprising a controller having a processing means communicable with a controller's database, the controller adapted to control the spatial position of the at least one surgical tool.

It is another object of the present invention to provide the method as defined above, wherein the controller's database is adapted to store a predetermined set of rules according to which ALLOWED and RESTRICTED movements of the at least one surgical tool are determined, such that each detected movement by said movement detection means of said at least one surgical tool is determined as either an ALLOWED movement or as a RESTRICTED movement according to said predetermined set of rules.

It is another object of the present invention to provide the method as defined above, wherein the predetermined set of rules comprises at least one rule selected from the group consisting of: most used tool, right tool rule, left tool rule, field of view rule, no fly zone rule, a route rule, an environmental rule, an operator input rule, a proximity rule; a collision prevention rule, preferred volume zone rule, preferred tool rule, movement detection rule, a history based rule, a tool-dependent allowed and RESTRICTED movements rule, and any combination thereof.

It is another object of the present invention to provide the method as defined above, wherein the route rule comprises a communicable database storing predefined route in which the at least one surgical tool is adapted to move within the surgical environment; the predefined route comprises n 3D spatial positions of the at least one surgical tool; n is an integer greater than or equals to 2; the ALLOWED movements are movements in which the at least one surgical tool is located substantially in at least one of the n 3D spatial positions of the predefined route, and the RESTRICTED movements are movements in which the location of the at least one surgical tool is substantially different from the n 3D spatial positions of the predefined route.

It is another object of the present invention to provide the method as defined above, wherein the environmental rule comprises a comprises a communicable database; the communicable database is adapted to received real-time image of the surgical environment and is adapted to perform real-time image processing of the same and to determined the 3D spatial position of hazards or obstacles in the surgical environment; the environmental rule is adapted to determine the ALLOWED and RESTRICTED movements according to the hazards or obstacles in the surgical environment, such that the RESTRICTED movements are movements in which the at least one surgical tool is located substantially in at least one of the 3D spatial positions, and the ALLOWED movements are movements in which the location of the at least one surgical tool is substantially different from the 3D spatial positions.

It is another object of the present invention to provide the method as defined above, wherein the hazards or obstacles in the surgical environment are selected from a group consisting of tissue, a surgical tool, an organ, an endoscope and any combination thereof.

It is another object of the present invention to provide the method as defined above, wherein the operator input rule comprises a communicable database; the communicable database is adapted to receive an input from the operator of the system regarding the ALLOWED and RESTRICTED movements of the at least one surgical tool.

It is another object of the present invention to provide the method as defined above, wherein the input comprises n 3D spatial positions; n is an integer greater than or equals to 2; wherein at least one of which is defined as ALLOWED location and at least one of which is defined as RESTRICTED location, such that the ALLOWED movements are movements in which the at least one surgical tool is located substantially in at least one of the n 3D spatial positions, and the RESTRICTED movements are movements in which the location of the at least one surgical tool is substantially different from the n 3D spatial positions.

It is another object of the present invention to provide the method as defined above, wherein the input comprises at least one predetermined rule according to which ALLOWED and RESTRICTED movements of the at least one surgical tool are determined, such that the spatial position of the at least one surgical tool is controlled by the controller according to the ALLOWED and RESTRICTED movements.

It is another object of the present invention to provide the method as defined above, wherein the predetermined rule is selected from the group consisting of: most used tool, right tool rule, left tool rule, field of view rule, no fly zone rule, a route rule, an environmental rule, an operator input rule, a proximity rule; a collision prevention rule, preferred volume zone rule, preferred tool rule, movement detection rule, a history based rule, a tool-dependent allowed and RESTRICTED movements rule, and any combination thereof.

It is another object of the present invention to provide the method as defined above, wherein the operator input rule converts an ALLOWED movement to a RESTRICTED movement and a RESTRICTED movement to an ALLOWED movement.

It is another object of the present invention to provide the method as defined above, wherein the proximity rule is adapted to define a predetermined distance between at least two surgical tools; the ALLOWED movements are movements which are within the range or out of the range of the predetermined distance, and the RESTRICTED movements which are out of the range or within the range of the predetermined distance.

It is another object of the present invention to provide the method as defined above, wherein the proximity rule is adapted to define a predetermined angle between at least three surgical tools; the ALLOWED movements are movements which are within the range or out of the range of the predetermined angle, and the RESTRICTED movements which are out of the range or within the range of the predetermined angle.

It is another object of the present invention to provide the method as defined above, wherein the collision prevention rule is adapted to define a predetermined distance between the at least one surgical tool and an anatomical element within the surgical environment; the ALLOWED movements are movements which are in a range that is larger than the predetermined distance, and the RESTRICTED movements are movements which is in a range that is smaller than the predetermined distance.

It is another object of the present invention to provide the method as defined above, wherein the anatomical element is selected from a group consisting of tissue, organ, another surgical tool or any combination thereof.

It is another object of the present invention to provide the method as defined above, wherein at least one of the following is being held true (a) said system additionally comprising an endoscope; said endoscope is adapted to provide real-time image of said surgical environment; (b) at least one of said surgical tools is an endoscope adapted to provide real-time image of said surgical environment.

It is another object of the present invention to provide the method as defined above, wherein the right tool rule is adapted to determine the ALLOWED movement of the endoscope according to the movement of the surgical tool positioned to right of the endoscope.

It is another object of the present invention to provide the method as defined above, wherein the left tool rule is adapted to determine the ALLOWED movement of the endoscope according to the movement of the surgical tool positioned to left of the endoscope.

It is another object of the present invention to provide the method as defined above, wherein the field of view rule comprises a communicable database comprising n 3D spatial positions; n is an integer greater than or equals to 2; the combination of all of the n 3D spatial positions provides a predetermined field of view; the field of view rule is adapted to determine the ALLOWED movement of the endoscope within the n 3D spatial positions so as to maintain a constant field of view, such that the ALLOWED movements are movements in which the endoscope is located substantially in at least one of the n 3D spatial positions, and the RESTRICTED movements are movements in which the location of the endoscope is substantially different from the n 3D spatial positions.

It is another object of the present invention to provide the method as defined above, wherein the preferred volume zone rule comprises a communicable database comprising n 3D spatial positions; n is an integer greater than or equals to 2; the n 3D spatial positions provides the preferred volume zone; the preferred volume zone rule is adapted to determine the ALLOWED movement of the endoscope within the n 3D spatial positions and RESTRICTED movement of the endoscope outside the n 3D spatial positions, such that the ALLOWED movements are movements in which the endoscope is located substantially in at least one of the n 3D spatial positions, and the RESTRICTED movements are movements in which the location of the endoscope is substantially different from the n 3D spatial positions.

It is another object of the present invention to provide the method as defined above, wherein the preferred tool rule comprises a communicable database, the database stores a preferred tool; the preferred tool rule is adapted to determine the ALLOWED movement of the endoscope according to the movement of the preferred tool.

It is another object of the present invention to provide the method as defined above, wherein the no fly zone rule comprises a communicable database comprising n 3D spatial positions; n is an integer greater than or equals to 2; the n 3D spatial positions define a predetermined volume within the surgical environment; the no fly zone rule is adapted to determine the RESTRICTED movement if the movement is within the no fly zone and the ALLOWED movement if the movement is outside the no fly zone, such that the RESTRICTED movements are movements in which the at least one of the surgical tool is located substantially in at least one of the n 3D spatial positions, and the ALLOWED movements are movements in which the location of the at least one surgical tool is substantially different from the n 3D spatial positions.

It is another object of the present invention to provide the method as defined above, wherein the most used tool rule comprises a communicable database counting the amount of movement of each of the surgical tools; the most used tool rule is adapted to constantly position the endoscope to track the movement of the most moved surgical tool.

It is another object of the present invention to provide the method as defined above, additionally comprising step of alerting the physician of a RESTRICTED movement of the at least one surgical tool.

It is another object of the present invention to provide the method as defined above, wherein the alert is selected from a group consisting of audio signaling, voice signaling, light signaling, flashing signaling and any combination thereof.

It is another object of the present invention to provide the method as defined above, wherein the ALLOWED movement is permitted by the controller and a RESTRICTED movement is denied by the controller.

It is another object of the present invention to provide the method as defined above, wherein the history based rule comprises a communicable database storing each 3D spatial position of each of the surgical tool, such that each movement of each surgical tool is stored; the history based rule is adapted to determine the ALLOWED and RESTRICTED movements according to historical movements of the at least one surgical tool, such that the ALLOWED movements are movements in which the at least one surgical tool is located substantially in at least one of the 3D spatial positions, and the RESTRICTED movements are movements in which the location of the at least one surgical tool is substantially different from the n 3D spatial positions.

It is another object of the present invention to provide the method as defined above, wherein the tool-dependent allowed and RESTRICTED movements rule comprises a communicable database; the communicable database is adapted to store predetermined characteristics of at least one of the surgical tool; the tool-dependent allowed and RESTRICTED movements rule is adapted to determine the ALLOWED and RESTRICTED movements according to the predetermined characteristics of the surgical tool.

It is another object of the present invention to provide the method as defined above, wherein the predetermined characteristics of the surgical tool are selected from the group consisting of: physical dimensions, structure, weight, sharpness, and any combination thereof.

It is another object of the present invention to provide the method as defined above, wherein the movement detection rule comprises a communicable database comprising the real-time 3D spatial positions of each of the surgical tool; and to detect movement of the at least one surgical tool when a change in the 3D spatial positions is received, such that the ALLOWED movements are movements in which the endoscope is directed to focus on the moving surgical tool.

It is another object of the present invention to provide the method as defined above, further comprising step of proving a maneuvering subsystem communicable with the controller, the maneuvering subsystem is adapted to spatially reposition the at least one surgical tool during a surgery according to the predetermined set of rules.

It is another object of the present invention to provide a surgical controlling system, comprising:
(a) at least one surgical tool adapted to be inserted into a surgical environment of a human body for assisting a surgical procedure;
(b) at least one endoscope adapted to provide real-time image of said surgical environment;
(c) at least one location estimating means adapted to real-time locate the 3D spatial position of said at least one surgical tool at any given time t;
(d) at least one movement detection means communicable with a movement's database and with said location estimating means; said movement's database is adapted to store said 3D spatial position of said at least one surgical tool at time $t_f$ and at time $t_0$, where $t_f > t_0$; said movement detection means is adapted to detect movement of said at least one surgical tool if the 3D spatial position of said at least one surgical tool at time $t_f$ is different than said 3D spatial position of said at least one surgical tool at time $t_0$; and,
(e) a controller having a processing means communicable with a controller's database, said controller adapted to control the spatial position of said at least one surgical tool; said controller's database is in communication with said movement detection means;

wherein said controller's database comprising n 3D spatial positions; n is an integer greater than or equal to 2; the combination of all of said n 3D spatial positions provides a predetermined field of view; said controller is adapted to relocate the 3D spatial positions of said endoscope if movement has been detected by said detection means, such that said field of view is maintained.

It is another object of the present invention to provide the surgical controlling system as defined above, wherein controller's database comprises n 3D spatial positions; n is an integer greater than or equal to 2; the combination of all of said n 3D spatial positions provides a predetermined field of view; said field of view rule is adapted to relocate said endoscope if movement of at least one of said surgical tools has been detected by said detection means, such that said field of view is maintained.

It is another object of the present invention to provide the method as defined above, wherein controller's database comprises n 3D spatial positions; n is an integer greater than or equal to 2; the combination of all of said n 3D spatial positions provides a predetermined field of view; said field of view rule is adapted to relocate said endoscope if movement of at least one of said surgical tools has been detected by said detection means, such that said field of view is maintained.

It is another object of the present invention to provide the surgical tracking system as defined above, wherein controller's database comprises n 3D spatial positions; n is an integer greater than or equal to 2; the combination of all of said n 3D spatial positions provides a predetermined field of view; said field of view rule is adapted to relocate said endoscope if movement of at least one of said surgical tools has been detected by said detection means, such that said field of view is maintained.

It is another object of the present invention to provide the method as defined above, wherein controller's database comprises n 3D spatial positions; n is an integer greater than or equal to 2; the combination of all of said n 3D spatial positions provides a predetermined field of view; said field of view rule is adapted to relocate said endoscope if movement of at least one of said surgical tools has been detected by said detection means, such that said field of view is maintained.

It is another object of the present invention to provide the surgical controlling system as defined above, wherein controller's database comprises n 3D spatial positions; n is an integer greater than or equal to 2; the combination of all of said n 3D spatial positions provides a predetermined field of view; said field of view rule is adapted to relocate said endoscope if movement of at least one of said surgical tools has been detected by said detection means, such that said field of view is maintained.

It is another object of the present invention to provide the method as defined above, wherein controller's database comprises n 3D spatial positions; n is an integer greater than or equal to 2; the combination of all of said n 3D spatial positions provides a predetermined field of view; said field of view rule is adapted to relocate said endoscope if movement of at least one of said surgical tools has been detected by said detection means, such that said field of view is maintained.

BRIEF DESCRIPTION OF THE FIGURES

In order to understand the invention and to see how it may be implemented in practice, and by way of non-limiting example only, with reference to the accompanying drawing, in which.

DETAILED DESCRIPTION OF THE PREFERRED EMBODIMENTS

Figure 1:
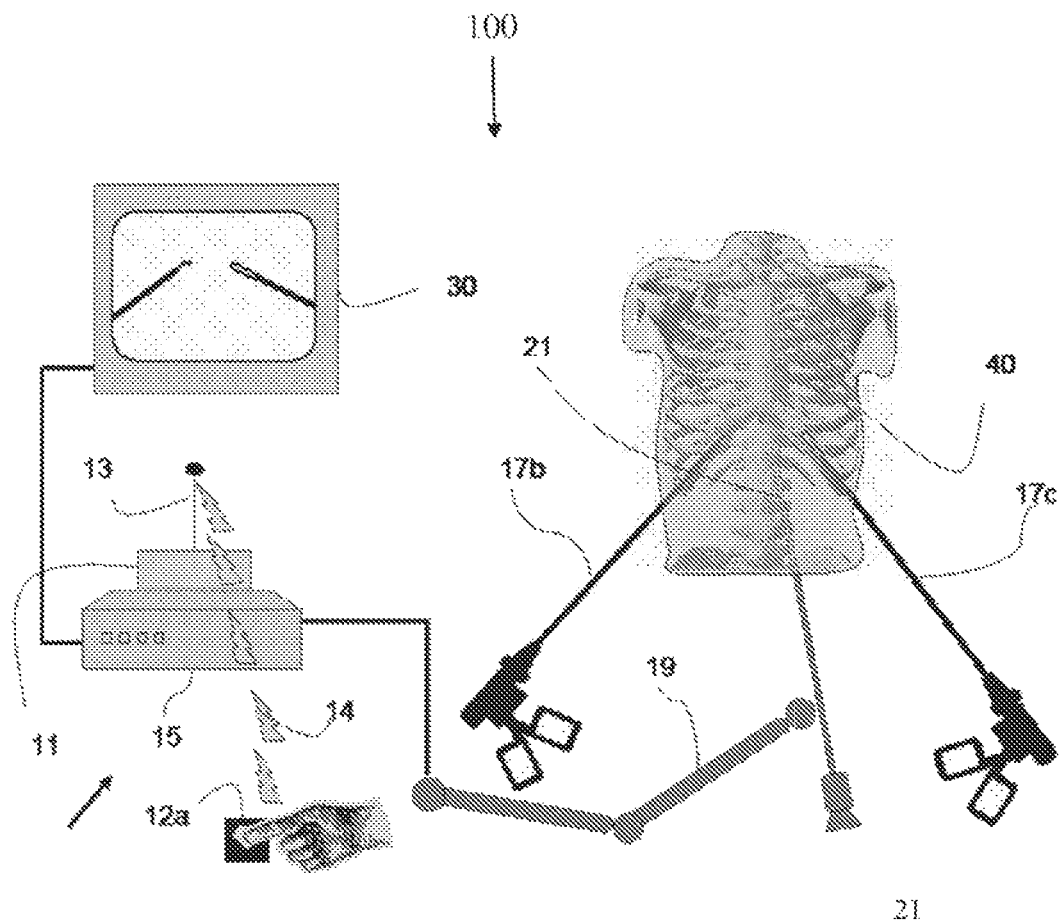
FIGS. 1-2 illustrate one embodiment of the present invention.

Before explaining at least one embodiment of the invention in detail, it is to be understood that the invention is not limited in its application to the details of construction and the arrangement of the components set forth in the following description or illustrated in the drawings. The invention is applicable to other embodiments or of being practiced or carried out in various ways. Also, it is to be understood that the phraseology and terminology employed herein is for the purpose of description and should not be regarded as limiting.

The term 'toggle' refers hereinafter to switching between one tagged surgical tool to another.

The term 'surgical environment' refers hereinafter to any anatomical part within the human body which may be in surrounding a surgical instrument. The environment may comprise: organs, body parts, walls of organs, arteries, veins, nerves, a region of interest, or any other anatomical part of the human body.

The term 'endoscope' refers hereinafter to any means adapted for looking inside the body for medical reasons. This may be any instrument used to examine the interior of a hollow organ or cavity of the body. The endoscope may also refer to any kind of a laparascope. It should be pointed that the following description may refer to an endoscope as a surgical tool.

The term 'region of interest' refers hereinafter to any region within the human body which may be of interest to the operator of the system of the present invention. The region of interest may be, for example, an organ to be operated on, a RESTRICTED area to which approach of a surgical instrument is RESTRICTED, a surgical instrument, or any other region within the human body.

The term 'spatial position' refers hereinafter to a predetermined spatial location and/or orientation of an object (e.g., the spatial location of the endoscope, the angular orientation of the endoscope, and any combination thereof).

The term 'prohibited area' refers hereinafter to a predetermined area to which a surgical tool (e.g., an endoscope) is prohibited to be spatially positioned in.

The term 'preferred area' refers hereinafter to predetermined area to which a surgical tool (e.g., an endoscope) is allowed and/or preferred to be spatially positioned in.

The term 'automated assistant' refers hereinafter to any mechanical device (including but not limited to a robotic device) that can maneuver and control the position of a surgical or endoscopic instrument, and that can in addition be adapted to receive commands from a remote source.

The term 'tool' or 'surgical instrument' refers hereinafter to any instrument or device introducible into the human body. The term may refer to any location on the tool. For example it can refer to the tip of the same, the body of the same and any combination thereof. It should be further pointed that the following description may refer to a surgical tool/instrument as an endoscope.

The term 'provide' refers hereinafter to any process (visual, tactile, or auditory) by which an instrument, computer, controller, or any other mechanical or electronic device can report the results of a calculation or other operation to a human operator.

The term 'automatic' or 'automatically' refers to any process that proceeds without the necessity of direct intervention or action on the part of a human being.

The term 'ALLOWED movement' refers hereinafter to any movement of a surgical tool which is permitted according to a predetermined set of rules.

The term 'RESTRICTED movement' refers hereinafter to any movement of a surgical tool which is forbidden according to a predetermined set of rules. For example, one rule, according to the present invention, provides a preferred volume zone rule which defines a favored zone within the surgical environment. Thus, according to the present invention an allowed movement of a surgical tool or the endoscope is a movement which maintains the surgical tool within the favored zone; and a RESTRICTED movement of a surgical tool is a movement which extracts (or moves) the surgical tool outside the favored zone.

The term 'time step' refers hereinafter to the working time of the system. At each time step, the system receives data from sensors and commands from operators and processes the data and commands and executes actions. The time step size is the elapsed time between time steps.

Laparoscopic surgery, also called minimally invasive surgery (MIS), is a modern surgical technique in which operations in the abdomen are performed through small incisions (usually 0.5-1.5 cm) as compared to larger incisions needed in traditional surgical procedures. The key element in laparoscopic surgery is the use of a laparoscope, which is a device adapted for viewing the scene within the body, at the distal end of the laparoscope. Either an imaging device is placed at the end of the laparoscope, or a rod lens system or fiber optic bundle is used to direct this image to the proximal end of the laparoscope. Also attached is a light source to illuminate the operative field, inserted through a 5 mm or 10 mm cannula or trocar to view the operative field.

The abdomen is usually injected with carbon dioxide gas to create a working and viewing space. The abdomen is essentially blown up like a balloon (insufflated), elevating the abdominal wall above the internal organs like a dome. Within this space, various medical procedures can be carried out.

In many cases, the laparoscope cannot view the entire working space within the body, so the laparoscope is repositioned to allow the surgeon to view regions of interest within the space.

The present invention discloses a surgical controlling system adapted to control the position of at least one surgical tool during a surgery of the human body. The system may perform the control by identifying the location of the surgical tool, and provide instruction to the operator to which direction the surgical tool may or should be directed, and to which direction the surgical tool is RESTRICTED from being moved to.

According to different embodiments of the present invention, the surgical controlling system comprises the following components:
 a. at least one surgical tool adapted to be inserted into a surgical environment of a human body for assisting a surgical procedure;
 b. at least one location estimating means adapted to real-time estimate/locate the location (i.e., the 3D spatial position) of the at least one surgical tool at any given time t;
 c. at least one movement detection means communicable with a movement-database and with said location estimating means; said movement-database is adapted to store said 3D spatial position of said at least one surgical tool at time $t_f$ and at time $t_0$; where $t_f > t_0$; said movement detection means is adapted to detect movement of said at least one surgical tool if the 3D spatial position of said at least one surgical tool at time $t_f$ is different than said 3D spatial position of said at least one surgical tool at time $t_o$, and,
 d. a controller having a processing means communicable with a database, the controller adapted to control the spatial position of the at least one surgical tool;

It is within the scope of the present invention that the database is adapted to store a predetermined set of rules according to which ALLOWED and RESTRICTED movements of the at least one surgical tool are determined, such that the spatial position of the at least one surgical tool is controlled by the controller according to the ALLOWED and RESTRICTED movements. In other words, each detected movement by said movement detection means of said at least one surgical tool is determined as either an ALLOWED movement or as a RESTRICTED movement according to said predetermined set of rules.

Thus, the present invention stores the 3D spatial position of each of said surgical tools at a current at time $t_f$ and at time $t_0$; where $t_f > t_0$. If the 3D spatial position of said at least one surgical tool at time $t_f$ is different than said 3D spatial position of said at least one surgical tool at time $t_o$ movement of the tool is detected. Next the system analyses said movement according to said set of rule and process whether said movement is ALLOWED movement or RESTRICTED movement.

According to one embodiment of the present invention, the system prevents said movement, if said movement is a RESTRICTED movement. Said movement prevention is obtained by controlling a maneuvering system which prevents the movement of said surgical tool.

According to one embodiment of the present invention, the system does not prevent said movement, (if said movement is a RESTRICTED movement), but merely signals/alerts the user (i.e., the physician) of said RESTRICTED movement.

According to another embodiment of the present invention, said surgical tool is an endoscope.

According to different embodiments of the present invention, the controller may provide a suggestion to the operator as to which direction the surgical tool has to move to or may be moved to.

Thus, according to a preferred embodiment of the present invention, the present invention provides a predetermined set of rules which define what is an "allowed movement" of any surgical tool within the surgical environment and what is a "RESTRICTED movement" of any surgical tool within the surgical environment.

According to some embodiments the system of the present invention comprises a maneuvering subsystem communicable with the controller, the maneuvering subsystem is adapted to spatially reposition the at least one surgical tool during surgery according to the predetermined set of rules.

According to some embodiments, the controller may provide instructions to a maneuvering subsystem for spatially repositioning the location of the surgical tool. According to these instructions, only ALLOWED movements of the surgical tool will be performed. Preventing RESTRICTED movements is performed by: detecting the location of the surgical tool; processing all current rules; analyzing the movement of the surgical tool and preventing the movement if the tool's movement is a RESTRICTED movement.

According to some embodiments, system merely alerts the physician of a RESTRICTED movement of at least one surgical tool (instead of preventing said RESTRICTED movement).

Alerting the physician of RESTRICTED movements (or, alternatively preventing a RESTRICTED movement) is performed by: detecting the location of the surgical tool; processing all current rules; analyzing the movement of the surgical tool and informing the surgeon (the user of the system) if the tool's movement is an allowed movement or a RESTRICTED movement.

Thus, according to a preferred embodiment of the present invention, if RESTRICTED movements are prevented, the same process (of detecting the location of the surgical tool; processing all current rules and analyzing the movement of the surgical tool) is followed except for the last movement, where the movement is prevented if the tool's movement is a RESTRICTED movement. The surgeon can also be informed that the movement is being prevented.

According to another embodiment, the above (alerting the physician and/or preventing the movement) is performed by detecting the location of the surgical tool and analyzing the surgical environment of the surgical tool. Following analysis of the surgical environment and detection of the location of the surgical tool, the system may assess all the risks which may follow a movement of the surgical tool in the predetermined direction. Therefore, each location in the surgical environment has to be analyzed so that any possible movement of the surgical tool will be classified as an ALLOWED movement or a RESTRICTED movement.

According to one embodiment of the present invention, the location of each tool is determined using image processing means and determining in real-time what is the 3D spatial location of each tool. It should be understood that the above mentioned "tool" may refer to the any location on the tool. For example, it can refer to the tip of the same, the body of the same and any combination thereof.

The predetermined set of rules which are the essence of the present invention are adapted to take into consideration all the possible factors which may be important during the surgical procedure. The predetermined set of rules may comprise the following rules or any combination thereof:

a. a route rule;
b. an environment rule;
c. an operator input rule;
d. a proximity rule;
e. a collision prevention rule;
f. a history based rule;
g. a tool-dependent allowed and RESTRICTED movements rule.
h. a most used tool rule;
i. a right tool rule;
j. a left tool rule;
k. a field of view rule;
l. a no fly zone rule;
m. an operator input rule;
n. a preferred volume zone rule;
o. a preferred tool rule;
p. a movement detection rule, Thus, for example, the collision prevention rule defines a minimum distance below which two or more tools should not be brought together (i.e., there is minimum distance between two or more tools that should be maintained). If the movement of one tool will cause it to come dangerously close to another tool (i.e., the distance between them, after the movement, is smaller than the minimum distance defined by the collision prevention rule), the controller either alerts the user that the movement is a RESTRICTED movement or does not permit the movement.

It should be emphasized that all of the above (and the following disclosure) is enabled by constantly monitoring the surgical environment, and identifying and locating the 3D spatial location of each element/tool in the surgical environment.

The identification is provided by conventional means known to any skilled in the art (e.g., image processing, optical means etc.).

The following provides explanations for each of the above mentioned rules and its functions:

According to some embodiments, the route rule comprises a predefined route in which the at least one surgical tool is adapted to move within the surgical environment; the ALLOWED movements are movements in which the at least one surgical tool is located within the borders of the predefined route, and the RESTRICTED movements are movements in which the at least one surgical tool is located out of the borders of the predefined route. Thus, according to this embodiment, the route rule comprises a communicable database storing at least one predefined route in which the at least one surgical tool is adapted to move within the surgical environment; the predefined route comprises n 3D spatial positions of the at least one surgical tool in the route; n is an integer greater than or equal to 2; ALLOWED movements are movements in which the at least one surgical tool is located substantially in at least one of the n 3D spatial positions of the predefined route, and RESTRICTED movements are movements in which the location of the at least one surgical tool is substantially different from the n 3D spatial positions of the predefined route.

In other words, according to the route rule, each of the surgical tool's courses (and path in any surgical procedure) is stored in a communicable database. ALLOWED movements are defined as movements in which the at least one surgical tool is located substantially in at least one of the stored routes; and RESTRICTED movements are movements in which the at least one surgical tool is in a substantially different location than any location in any stored route.

According to some embodiments, the environmental rule is adapted to determine ALLOWED and RESTRICTED movements according to hazards or obstacles in the surgical environment as received from an endoscope or other sensing means. Thus, according to this embodiment, the environmental rule comprises a comprises a communicable database; the communicable database is adapted to received real-time images of the surgical environment and is adapted to perform real-time image processing of the same and to determine the 3D spatial position of hazards or obstacles in the surgical environment; the environmental rule is adapted to determine ALLOWED and RESTRICTED movements according to hazards or obstacles in the surgical environment, such that RESTRICTED movements are movements in which at least one surgical tool is located substantially in at least one of the 3D spatial positions, and ALLOWED movements are movements in which the location of at least one surgical tool is substantially different from the 3D spatial positions.

In other words, according to the environment rule, each element in the surgical environment is identified so as to establish which is a hazard or obstacle (and a path in any surgical procedure) and each hazard and obstacle (and path) is stored in a communicable database. RESTRICTED movements are defined as movements in which the at least one surgical tool is located substantially in the same location as that of the hazards or obstacles; and the ALLOWED movements are movements in which the location of the at least one surgical tool is substantially different from that of all of the hazards or obstacles.

According to other embodiments, hazards and obstacles in the surgical environment are selected from a group consisting of tissues, surgical tools, organs, endoscopes and any combination thereof.

According to some embodiments, the operator input rule is adapted to receive an input from the operator of the system regarding the ALLOWED and RESTRICTED movements of the at least one surgical tool. Thus, according to this embodiment, the operator input rule comprises a communicable database; the communicable database is adapted to receive an input from the operator of the system regarding ALLOWED and RESTRICTED movements of the at least one surgical tool.

According to other embodiments, the input comprises n 3D spatial positions; n is an integer greater than or equal to 2; wherein at least one of which is defined as an ALLOWED location and at least one of which is defined as a RESTRICTED location, such that the ALLOWED movements are movements in which the at least one surgical tool is located substantially in at least one of the n 3D ALLOWED spatial positions, and the RESTRICTED movements are movements in which the location of the at least one surgical tool is substantially different from the n 3D ALLOWED spatial positions.

According to other embodiments, the input comprises at least one rule according to which ALLOWED and RESTRICTED movements of the at least one surgical tool are determined, such that the spatial position of the at least one surgical tool is controlled by the controller according to the ALLOWED and RESTRICTED movements.

According to other embodiments, the operator input rule can convert an ALLOWED movement to a RESTRICTED movement and a RESTRICTED movement to an ALLOWED movement.

According to some embodiments, the proximity rule is adapted to define a predetermined distance between the at least one surgical tool and at least one another surgical tool; the ALLOWED movements are movements which are within the range or out of the range of the predetermined distance, and the RESTRICTED movements which are out of the range or within the range of the predetermined distance; the ALLOWED movements and the RESTRICTED movements are defined according to different ranges. Thus, according to this embodiment, the proximity rule is adapted to define a predetermined distance between at least two surgical tools. In a preferred embodiment, the ALLOWED movements are movements which are within the range of the predetermined distance, while the RESTRICTED movements which are out of the range of the predetermined distance. In another preferred embodiment, the ALLOWED movements are movements which are out of the range of the predetermined distance, while the RESTRICTED movements are within the range of the predetermined distance It should be pointed out that the above mentioned distance can be selected from the following:
(f) the distance between the tip of the first tool and the tip of the second tool;
(g) the distance between the body of the first tool and the tip of the second tool;
(h) the distance between the body of the first tool and the body of the second tool;
(i) the distance between the tip of the first tool and the body of the second tool; and any combination thereof.

According to another embodiment, the proximity rule is adapted to define a predetermined angle between at least three surgical tools; ALLOWED movements are movements which are within the range or out of the range of the predetermined angle, and RESTRICTED movements are movements which are out of the range or within the range of the predetermined angle.

According to some embodiments, the collision prevention rule is adapted to define a predetermined distance between the at least one surgical tool and an anatomical element within the surgical environment (e.g. tissue, organ, another surgical tool or any combination thereof); the ALLOWED movements are movements which are in a range that is larger than the predetermined distance, and the RESTRICTED movements are movements which is in a range that is smaller than the predetermined distance.

According to another embodiment, the anatomical element is selected from a group consisting of tissue, organ, another surgical tool or any combination thereof.

According to some embodiments, the surgical tool is an endoscope. The endoscope is adapted to provide real-time images of the surgical environment.

According to some embodiments, the right tool rule is adapted to determine the ALLOWED movement of the endoscope according to the movement of a surgical tool in a specified position in relation to the endoscope, preferably positioned to right of the same. According to this rule, the tool which is defined as the right tool is constantly tracked by the endoscope. According to some embodiments, the right tool is defined as the tool positioned to the right of the endoscope; according to other embodiments, any tool can be defined as the right tool. An allowed movement, according to the right tool rule, is a movement in which the endoscope field of view is moved to a location substantially the same as the location of the right tool, thereby tracking the right tool. A RESTRICTED movement, according to the right tool rule, is a movement in which the endoscope field of view is moved to a location substantially different from the location of the right tool.

According to some embodiments, the left tool rule is adapted to determine the ALLOWED movement of the endoscope according to the movement of a surgical tool in a specified position in relation to the endoscope, preferably positioned to left of the same. According to this rule, the tool which is defined as the left tool is constantly tracked by the endoscope. According to some embodiments, the left tool is defined as the tool positioned to the left of the endoscope; according to other embodiments, any tool can be defined as the left tool. An allowed movement, according to the left tool rule, is a movement in which the endoscope field of view is moved to a location substantially the same as the location of the left tool. A RESTRICTED movement, according to the left tool rule, is a movement in which the endoscope field of view is moved to a location substantially different from the location of the left tool.

According to some embodiments, the field of view rule is adapted to define a field of view and maintain that field of view. The field of view rule is defined such that if the endoscope is adapted to track a predetermined set of tools in a desired field of view, when one of those tools is no longer in the field of view, the rule instructs the endoscope to zoom out so as to reintroduce the tool into the field of view. Thus, according to this embodiment, the field of view rule comprises a communicable database comprising n 3D spatial positions; n is an integer greater than or equal to 2; the combination of all of the n 3D spatial positions provides a predetermined field of view; the field of view rule is adapted to determine the ALLOWED movement of the endoscope within the n 3D spatial positions so as to maintain a constant field of view, such that the ALLOWED movements are movements in which the endoscope is located substantially in at least one of the n 3D spatial positions, and the RESTRICTED movements are movements in which the location of the endoscope is substantially different from the n 3D spatial positions.

Thus, according to another embodiment of the field of view rule, the field of view rule comprises a communicable database comprising n 3D spatial positions; n is an integer greater than or equal to 2; the combination of all of the n 3D spatial positions provides a predetermined field of view. The field of view rule further comprises a communicable database of m tools and the 3D spacial locations of the same, where m is an integer greater than or equal to 1 and where a tool can be a surgical tool, an anatomical element and any combination thereof. The combination of all of the n 3D spatial positions provides a predetermined field of view. The field of view rule is adapted to determine ALLOWED movement of the endoscope such that the m 3D spatial positions of the tools comprise at least one of the n 3D spatial positions of the field of view, and RESTRICTED movements are movements in which the 3D spatial position of at least one tool is substantially different from the n 3D spatial positions of the field of view.

According to another embodiment, the preferred volume zone rule comprises a communicable database comprising n 3D spatial positions; n is an integer greater than or equal to 2; the n 3D spatial positions provides the preferred volume zone; the preferred volume zone rule is adapted to determine the ALLOWED movement of the endoscope within the n 3D spatial positions and RESTRICTED movement of the endoscope outside the n 3D spatial positions, such that the ALLOWED movements are movements in which the endoscope is located substantially in at least one of the n 3D spatial positions, and the RESTRICTED movements are movements in which the location of the endoscope is substantially different from the n 3D spatial positions. In other words, the preferred volume zone rule defines a volume of interest (a desired volume of interest), such that an ALLOWED movement, according to the preferred volume zone rule, is a movement in which the endoscope (or any surgical tool) is moved to a location within the defined preferred volume. A RESTRICTED movement, according to the preferred volume zone rule, is a movement in which the endoscope (or any surgical tool) is moved to a location outside the defined preferred volume.

According to another embodiment, the preferred tool rule comprises a communicable database, the database stores a preferred tool; the preferred tool rule is adapted to determine the ALLOWED movement of the endoscope according to the movement of the preferred tool. In other words, the preferred tool rule defines a preferred tool (i.e., a tool of interest) that the user of the system wishes to track. An allowed movement, according to the preferred tool rule, is a movement in which the endoscope is moved to a location substantially the same as the location of the preferred tool. A RESTRICTED movement is a movement in which the endoscope is moved to a location substantially different from the location of the preferred tool. Thus, according to the preferred tool rule the endoscope constantly tracks the preferred tool, such that the field of view, as seen from the endoscope, is constantly the preferred tool. It should be noted that the user may define in said preferred tool rule to constantly tack the tip of said preferred tool or alternatively, the user may define in said preferred tool rule to constantly track the body or any location on the preferred tool.

According to some embodiments, the no fly zone rule is adapted to define a RESTRICTED zone into which no tool (or alternatively no predefined tool) is permitted to enter. Thus, according to this embodiment, the no fly zone rule comprises a communicable database comprising n 3D spatial positions; n is an integer greater than or equal to 2; the n 3D spatial positions define a predetermined volume within the surgical environment; the no fly zone rule is adapted to determine a RESTRICTED movement if the movement is within the no fly zone and an ALLOWED movement if the movement is outside the no fly zone, such that RESTRICTED movements are movements in which the at least one surgical tool is located substantially in at least one of the n 3D spatial positions, and the ALLOWED movements are movements in which the location of the at least one surgical tool is substantially different from the n 3D spatial positions.

According to another embodiment, the most used tool function is adapted to define (either real-time, during the procedure or prior to the procedure) which tool is the most used tool (i.e., the tool which is moved the most during the procedure) and to instruct the maneuvering subsystem to constantly position the endoscope to track the movement of this tool. Thus, according to this embodiment, the most used tool rule comprises a communicable database counting the number of movements of each of the surgical tools; the most used tool rule is adapted to constantly position the endoscope to track the movement of the surgical tool with the largest number of movements. In another embodiment of the most used tool function, the communicable database measures the amount of movement of each of the surgical tools; the most used tool rule is adapted to constantly position the endoscope to track the movement of the surgical tool with the largest amount of movement.

According to another embodiment, the system is adapted to alert the physician of a RESTRICTED movement of at least one surgical tool. The alert can be audio signaling, voice signaling, light signaling, flashing signaling and any combination thereof.

According to another embodiment, an ALLOWED movement is one permitted by the controller and a RESTRICTED movement is one denied by the controller.

According to another embodiment, the operator input rule function is adapted to receive an input from the operator of the system regarding ALLOWED and RESTRICTED movements of the at least one surgical tool. In other words, the operator input rule function receives instructions from the physician as to what can be regarded as ALLOWED movements and what are RESTRICTED movements. According to another embodiment, the operator input rule is adapted to convert an ALLOWED movement to a RESTRICTED movement and a RESTRICTED movement to an ALLOWED movement.

According to some embodiments, the history-based rule is adapted to determine the ALLOWED and RESTRICTED movements according to historical movements of the at least one surgical tool in at least one previous surgery. Thus, according to this embodiment, the history-based rule comprises a communicable database storing each 3D spatial position of each of the surgical tools, such that each movement of each surgical tool is stored; the history-based rule is adapted to determine ALLOWED and RESTRICTED movements according to historical movements of the at least one surgical tool, such that the ALLOWED movements are movements in which the at least one surgical tool is located substantially in at least one of the 3D spatial positions, and the RESTRICTED movements are movements in which the location of the at least one surgical tool is substantially different from the n 3D spatial positions.

According to some embodiments, the tool-dependent allowed and RESTRICTED movements rule is adapted to determine ALLOWED and RESTRICTED movements according to predetermined characteristics of the surgical tool, where the predetermined characteristics of the surgical tool are selected from a group consisting of: physical dimensions, structure, weight, sharpness, and any combination thereof. Thus, according to this embodiment, the tool-dependent ALLOWED and RESTRICTED movements rule comprises a communicable database; the communicable database is adapted to store predetermined characteristics of at least one of the surgical tools; the tool-dependent ALLOWED and RESTRICTED movements rule is adapted to determine ALLOWED and RESTRICTED movements according to the predetermined characteristics of the surgical tool.

According to another embodiment, the predetermined characteristics of the surgical tool are selected from a group consisting of: physical dimensions, structure, weight, sharpness, and any combination thereof.

According to this embodiment, the user can define, e.g., the structure of the surgical tool he wishes the endoscope to track. Thus, according to the tool-dependent allowed and RESTRICTED movements rule the endoscope constantly tracks the surgical tool having said predetermined characteristics as defined by the user.

According to another embodiment of the present invention, the movement detection rule comprises a communicable database comprising the real-time 3D spatial positions of each surgical tool; said movement detection rule is adapted to detect movement of at least one surgical tool. When a change in the 3D spatial position of that surgical tool is received, ALLOWED movements are movements in which the endoscope is re-directed to focus on the moving surgical tool.

According to another embodiment of the present invention, the system further comprises a maneuvering subsystem communicable with the controller. The maneuvering subsystem is adapted to spatially reposition the at least one surgical tool during a surgery according to the predetermined set of rules.

According to some embodiments, the at least one location estimating means is at least one endoscope adapted to acquire real-time images of a surgical environment within the human body for the estimation of the location of at least one surgical tool.

According to another embodiment, the location estimating means comprise at least one selected from a group consisting of optical imaging means, radio frequency transmitting and receiving means, at least one mark on at least one surgical tool and any combination thereof.

According to another embodiment, the at least one location estimating means is an interface subsystem between a surgeon and at least one surgical tool, the interface subsystem comprising (a) at least one array comprising N regular light sources or N pattern light sources, where N is a positive integer; (b) at least one array comprising M cameras, where M is a positive integer; (c) optional optical markers and means for attaching the optical markers to at least one surgical tool; and (d) a computerized algorithm operable via the controller, the computerized algorithm adapted to record images received by each camera of each of the M cameras and to calculate therefrom the position of each of the tools, and further adapted to provide automatically the results of the calculation to the human operator of the interface.

It is well known that surgery is a highly dynamic procedure with a constantly changing environment which depends on many variables. A non-limiting list of these variables includes, for example: the type of the surgery, the working space (e.g., with foreign objects, dynamic uncorrelated movements, etc), the type of tools used during the surgery, changing background, relative movements, dynamic procedures, dynamic input from the operator and the history of the patient. Therefore, there is need for a system which is able to integrate all the variables by weighting their importance and deciding to which spatial position the endoscope should be relocated.

The present invention can be also utilized to improve the interface between the operators (e.g., the surgeon, the operating medical assistant, the surgeon's colleagues, etc.). Moreover, the present invention can be also utilized to control and/or direct an automated maneuvering subsystem to focus the endoscope on an instrument selected by the surgeon, or to any other region of interest. This may be performed in order to estimate the location of at least one surgical tool during a surgical procedure.

The present invention also discloses a surgical tracking system which is adapted to guide and relocate an endoscope to a predetermined region of interest in an automatic and/or a semi-automatic manner. This operation is assisted by an image processing algorithm(s) which is adapted to analyze the received data from the endoscope in real time, and to assess the surgical environment of the endoscope.

According to an embodiment, the system comprises a "smart" tracking subsystem, which receives instructions from a maneuvering function f(t) (t is the time) as to where to direct the endoscope and which instructs the maneuvering subsystem to relocate the endoscope to the required area.

The maneuvering function f(t) receives, as input, output from at least two instructing functions $g_i(t)$, analyses their output and provides instruction to the "smart" tracking system (which eventually re-directs the endoscope).

According to some embodiments, each instructing function $g_i(t)$ is also given a weighting function, $\alpha_i(t)$.

The instructing functions $g_i(t)$ of the present invention are functions which are configured to assess the environment of the endoscope and the surgery, and to output data which guides the tracking subsystem for controlling the spatial position of the maneuvering subsystem and the endoscope. The instructing functions $g_i(t)$ may be selected from a group consisting of:

a. a tool detection function $g_1(t)$;
b. a movement detection function $g_2(t)$;
c. an organ detection function $g_3(t)$;
d. a collision detection function $g_4(t)$;
e. an operator input function $g_5(t)$;
f. a prediction function $g_6(t)$;
g. a past statistical analysis function $g_7(t)$;
h. a most used tool function $g_8(t)$;
i. a right tool function $g_9(t)$;
j. a left tool function $g_{10}(t)$;
k. a field of view function $g_{11}(t)$;
l. a preferred volume zone function $g_{12}(t)$;
m. a no fly zone function $g_{13}(t)$;
n. a proximity function $g_{14}(t)$;
o. a tagged tool function $g_{15}(t)$;
p. a preferred tool function $g_{16}(t)$.

Thus, for example, the maneuvering function f(t) receives input from two instructing functions: the collision detection function $g_4(t)$ (the function providing information whether the distance between two elements is smaller than a predetermined distance) and from the most used tool function $g_8(t)$ (the function counts the number of times each tool is moved during a surgical procedure and provides information as to whether the most moved or most used tool is currently moving). The output given from the collision detection function $g_4(t)$ is that a surgical tool is dangerously close to an organ in the surgical environment. The output given from the most used tool function $g_8(t)$ is that the tool identified statistically as the most moved tool is currently moving.

The maneuvering function f(t) then assigns each of the instructing functions with weighting functions $\alpha_i(t)$. For example, the most used tool function $g_8(t)$ is assigned with a greater weight than the weight assigned to the collision detection function $g_4(t)$.

After the maneuvering function f(t) analyses the information received from the instructing functions $g_i(t)$ and the weighting functions $\alpha_i(t)$ of each, the same outputs instructions to the maneuvering subsystem to re-direct the endoscope (either to focus on the moving tool or on the tool approaching dangerously close to the organ).

It should be emphasized that all of the above (and the following disclosure) is enabled by constantly monitoring and locating/identifying the 3D spatial location of each element/tool in the surgical environment.

The identification is provided by conventional means known to any skilled in the art (e.g., image processing, optical means etc.).

According to some embodiments, the surgical tracking subsystem comprises:

a. at least one endoscope adapted to acquire real-time images of a surgical environment within the human body;
b. a maneuvering subsystem adapted to control the spatial position of the endoscope during the laparoscopic surgery; and,
c. a tracking subsystem in communication with the maneuvering subsystem, adapted to control the maneuvering subsystem so as to direct and modify the spatial position of the endoscope to a region of interest.

According to this embodiment, the tracking subsystem comprises a data processor. The data processor is adapted to perform real-time image processing of the surgical environment and to instruct the maneuvering subsystem to modify the spatial position of the endoscope according to input received from a maneuvering function f(t); the maneuvering function f(t) is adapted to (a) receive input from at least two instructing functions $g_i(t)$, where i is 1, ..., n and n≥2 and where t is time; i and n are integers; and (b) to output instructions to the maneuvering subsystem based on the input from the at least two instructing functions $g_i(t)$, so as to spatially position the endoscope to the region of interest.

According to one embodiment, the tool detection function $g_1(t)$ is adapted to detect tools in the surgical environment. According to this embodiment, the tool detection function is adapted to detect surgical tools in the surgical environment and to output instructions to the tracking subsystem to instruct the maneuvering subsystem to direct the endoscope to the detected surgical tools.

According to some embodiments, the functions $g_i(t)$ may rank the different detected areas in the surgical environment according to a ranking scale (e.g., from 1 to 10) in which prohibited areas (i.e., areas which are defined as area to which the surgical tools are forbidden to 'enter) receive the lowest score (e.g., 1) and preferred areas (i.e., areas which are defined as area in which the surgical tools should be maintained) receive the highest score (e.g., 10).

According to a preferred embodiment, one function $g_1(t)$ is adapted to detect tools in the surgical environment and inform the maneuvering function f(t) if they are in preferred areas or in prohibited areas.

According to some embodiments, the movement detection function $g_2(t)$ comprises a communicable database comprising the real-time 3D spatial positions of each of the surgical tools in the surgical environment; means to detect movement of the at least one surgical tool when a change in the 3D spatial positions is received, and means to output instructions to the tracking subsystem to instruct the maneuvering subsystem to direct the endoscope to the moved surgical tool.

According to some embodiments, the organ detection function $g_3(t)$ is adapted to detect physiological organs in the surgical environment and to classify the detected organs as prohibited areas or preferred areas. For example, if the operator instructs the system that the specific surgery is kidney surgery, the organ detection function $g_3(t)$ will classify the kidneys (or one kidney, if the surgery is specified to be on a single kidney) as a preferred area and other organs will be classified as prohibited areas. According to another embodiment, the organ detection function is adapted to detect organs in the surgical environment and to output instructions to the tracking subsystem to instruct the maneuvering subsystem to direct the endoscope to the detected organs. According to some embodiments, the right tool function is adapted to detect surgical tool positioned to right of the endoscope and to output instructions to the tracking subsystem to instruct the maneuvering system to constantly direct the endoscope on the right tool and to track the right tool.

According to another embodiment, the left tool function is adapted to detect surgical tool positioned to left of the endoscope and to output instructions to the tracking subsystem to instruct the maneuvering system to constantly direct the endoscope on the left tool and to track the left tool.

According to some embodiments, the collision detection function $g_4(t)$ is adapted to detect prohibited areas within the surgical environment so as to prevent collisions between the endoscope and the prohibited areas. For example, if the endoscope is located in a narrow area in which a precise movement of the same is preferred, the collision detection function $g_4(t)$ will detect and classify different areas (e.g., nerves, veins, walls of organs) as prohibited areas. Thus, according to this embodiment, the collision prevention function is adapted to define a predetermined distance between the at least one surgical tool and an anatomical element within the surgical environment; and to output instructions to the tracking subsystem to instruct the maneuvering subsystem to direct the endoscope to the surgical tool and the anatomical element within the surgical environment if the distance between the at least one surgical tool and an anatomical element is less than the predetermined distance. According to one embodiment of the present invention the anatomical element is selected from a group consisting of tissue, organ, another surgical tool and any combination thereof.

According to some embodiments, the operator input function $g_5(t)$ is adapted to receive an input from the operator. The input can be, for example: an input regarding prohibited areas in the surgical environment, an input regarding allowed areas in the surgical environment, or an input regarding the region of interest and any combination thereof. The operator input function $g_5(t)$ can receive instructions from the operator before or during the surgery, and respond accordingly. According to some embodiments, the operator input function may further comprise a selection algorithm for selection of areas selected from a group consisting of: prohibited areas, allowed areas, regions of interest, and any combination thereof. The selection may be performed via an input device (e.g., a touch screen).

According to some embodiments, the operator input function $g_5(t)$ comprises a communicable database; the communicable database is adapted to receive an input from the operator of the system; the input comprising n 3D spatial positions; n is an integer greater than or equal to 2; and to output instructions to the tracking subsystem to instruct the maneuvering subsystem to direct the endoscope to the at least one 3D spatial position received.

According to some embodiments, the prediction function $g_6(t)$ is adapted to provide data regarding a surgical environment at a time $t_f > t_0$, wherein to is the present time and $t_f$ is a future time. The prediction function $g_6(t)$ may communicate with a database which stores data regarding the environment of the surgery (e.g., the organs in the environment). This data may be used by the prediction function $g_6(t)$ for the prediction of expected or unexpected events or expected or unexpected objects during the operation. Thus, according to this embodiment, the prediction function $g_6(t)$ comprises a communicable database storing each 3D spatial position of each of surgical tool within the surgical environment, such that each movement of each surgical tool is stored; the prediction function is adapted to (a) to predict the future 3D spatial position of each of the surgical tools (or each object); and, (b) to output instructions to the tracking subsystem to instruct the maneuvering subsystem to direct the endoscope to the future 3D spatial position.

According to some embodiments, the past statistical analysis function $g_7(t)$ is adapted to provide data regarding the surgical environment or the laparoscopic surgery based on past statistical data stored in a database. The data regarding the surgical environment may be for example: data regarding prohibited areas, data regarding allowed areas, data regarding the region of interest and any combination thereof. Thus, according to this embodiment, the past statistical analysis function $g_6(t)$ comprises a communicable database storing each 3D spatial position of each of surgical tool within the surgical environment, such that each movement of each surgical tool is stored; the past statistical analysis function $g_6(t)$ is adapted to (a) perform statistical analysis on the 3D spatial positions of each of the surgical tools in the past; and, (b) to predict the future 3D spatial position of each of the surgical tools; and, (c) to output instructions to the tracking subsystem to instruct the maneuvering subsystem to direct the endoscope to the future 3D spatial position. Thus, according to the past statistical analysis function $g_7(t)$, the past movements of each tool are analyzed and, according to this analysis, a prediction of the tool's next move is provided.

According to another embodiment, the most used tool function $g_8(t)$ comprises a communicable database counting the amount of movement of each surgical tool located within the surgical environment; the most used tool function is adapted to output instructions to the tracking subsystem to instruct the maneuvering subsystem to direct the endoscope to constantly position the endoscope to track the movement of the most moved surgical tool. The amount of movement of a tool can be defined as the total number of movements of that tool or the total distance the tool has moved.

According to some embodiments, the right tool function $g_9(t)$ is adapted to detect at least one surgical tool in a specified position in relation to the endoscope, preferably positioned to right of the endoscope and to output instructions to the tracking subsystem to instruct the maneuvering subsystem to constantly direct the endoscope to the right tool and to track the same. According to preferred embodiments, the right tool is defined as the tool positioned to the right of the endoscope; according to other embodiments, any tool can be defined as the right tool.

According to another embodiment, the left tool function $g_{10}(t)$ is adapted to detect at least one surgical tool in a specified position in relation to the endoscope, preferably positioned to left of the endoscope and to output instructions to the tracking subsystem to instruct the maneuvering subsystem to constantly direct the endoscope to the left tool and to track the same. According to preferred embodiments, the left tool is defined as the tool positioned to the left of the endoscope; according to other embodiments, any tool can be defined as the left tool.

According to another embodiment, the field of view function $g_{11}(t)$ comprises a communicable database comprising n 3D spatial positions; n is an integer greater than or equal to 2; the combination of all of the n 3D spatial positions provides a predetermined field of view; the field of view function is adapted to output instructions to the tracking subsystem to instruct the maneuvering subsystem to direct the endoscope to at least one 3D spatial position substantially within the n 3D spatial positions so as to maintain a constant field of view.

According to another embodiment, the preferred volume zone function $g_{12}(t)$ comprises a communicable database comprising n 3D spatial positions; n is an integer greater than or equal to 2; the n 3D spatial positions provide the preferred volume zone; the preferred volume zone function $g_{12}(t)$ is adapted to output instructions to the tracking subsystem to instruct the maneuvering subsystem to direct the endoscope to at least one 3D spatial position substantially within the preferred volume zone.

According to another embodiment, the no fly zone function $g_{13}(t)$ comprises a communicable database comprising n 3D spatial positions; n is an integer greater than or equal to 2; the n 3D spatial positions define a predetermined volume within the surgical environment; the no fly zone function $g_{13}(t)$ is adapted to output instructions to the tracking subsystem to instruct the maneuvering subsystem to direct the endoscope to at least one 3D spatial position substantially different from all the n 3D spatial positions.

According to some embodiments, the proximity function $g_{14}(t)$ is adapted to define a predetermined distance between at least two surgical tools; and to output instructions to the tracking subsystem to instruct the maneuvering subsystem to direct the endoscope to the two surgical tools if the distance between the two surgical tools is less than or if it is greater than the predetermined distance.

According to another embodiment, the proximity function $g_{14}(t)$ is adapted to define a predetermined angle between at least three surgical tools; and to output instructions to the tracking subsystem to instruct the maneuvering subsystem to direct the endoscope to the three surgical tools if the angle between the two surgical tools is less than or if it is greater than the predetermined angle.

According to another embodiment, the preferred volume zone function comprises communicable database comprising n 3D spatial positions; n is an integer greater than or equals to 2; the n 3D spatial positions provides the preferred volume zone; the preferred volume zone function is adapted to output instructions to the tracking subsystem to instruct the maneuvering system to direct the endoscope to the preferred volume zone.

According to another embodiment, the field of view function comprises a communicable database comprising n 3D spatial positions; n is an integer greater than or equals to 2; the combination of all of the n 3D spatial positions provides a predetermined field of view; the field of view function is adapted to output instructions to the tracking subsystem to instruct the maneuvering system to direct the endoscope to at least one 3D spatial position substantially within the n 3D spatial positions so as to maintain a constant field of view.

According to another embodiment, the no fly zone function comprises a communicable database comprising n 3D spatial positions; n is an integer greater than or equals to 2; the n 3D spatial positions define a predetermined volume within the surgical environment; the no fly zone function is adapted to output instructions to the tracking subsystem to instruct the maneuvering system to direct the endoscope to at least one 3D spatial position substantially different from all the n 3D spatial positions.

According to another embodiment, the most used tool function comprises a communicable database counting the amount of movement of each surgical tool located within the surgical environment; the most used tool function is adapted to output instructions to the tracking subsystem to instruct the maneuvering system to direct the endoscope to constantly position the endoscope to track the movement of the most moved surgical tool.

According to some embodiments, the prediction function $g_6(t)$ is adapted to provide data regarding a surgical environment in a time $t_f > t$, wherein t is the present time and $t_f$ is the future time. The prediction function $g_6(t)$ may communicate with a database which stores data regarding the environment of the surgery (e.g., the organs in the environment). This data may be used by the prediction function $g_6(t)$ for the prediction of expected or unexpected events or object during the operation. Thus, according to this embodiment, the prediction function comprises a communicable database storing each 3D spatial position of each of surgical tool within the surgical environment, such that each movement of each surgical tool is stored; the prediction function is adapted to (a) to predict the future 3D spatial position of each of the surgical tools; and, (b) to output instructions to the tracking subsystem to instruct the maneuvering system to direct the endoscope to the future 3D spatial position.

According to some embodiments, the past statistical analysis function $g_7(t)$ is adapted to provide data regarding the surgical environment or the laparoscopic surgery based on past statistical data stored in a database. The data regarding the surgical environment may be for example: data regarding prohibited areas, data regarding allowed areas, data regarding the region of interest. Thus, according to this embodiment, the past statistical analysis function comprises a communicable database storing each 3D spatial position of each of surgical tool within the surgical environment, such that each movement of each surgical tool is stored; the past statistical analysis function is adapted to (a) statistical analyze the 3D spatial positions of each of the surgical tools in the past; and, (b) to predict the future 3D spatial position of each of the surgical tools; and, (c) to output instructions to the tracking subsystem to instruct the maneuvering system to direct the endoscope to the future 3D spatial position. Thus, according to the past statistical analysis function $g_7(t)$, the past movements of each tool are analyzed and according to this analysis a future prediction of the tool's next move is provided.

According to some embodiments, preferred tool function comprises a communicable database, the database stores a preferred tool; the preferred tool function is adapted to output instructions to the tracking subsystem to instruct the maneuvering system to constantly direct the endoscope to the preferred tool, such that said endoscope constantly tracks said preferred tool.

Thus, according to the preferred tool function the endoscope constantly tracks the preferred tool, such that the field of view, as seen from the endoscope, is constantly maintained on said preferred tool. It should be noted that the user may define in said preferred tool function to constantly tack the tip of said preferred tool or alternatively, the user may define in said preferred tool function to constantly track the body or any location on the preferred tool.

According to some embodiments, the tagged tool function $g_{15}(t)$ comprises means adapted to tag at least one surgical tool within the surgical environment and to output instructions to the tracking subsystem to instruct the maneuvering subsystem to constantly direct the endoscope to the tagged surgical tool. Thus, according to the tagged tool function the endoscope constantly tracks the preferred (i.e., tagged) tool, such that the field of view, as seen from the endoscope, is constantly maintained on said preferred (tagged) tool. It should be noted that the user may define in said tagged tool function to constantly tack the tip of said preferred (tagged) tool or alternatively, the user may define in said tagged tool function to constantly track the body or any location on the preferred (tagged) tool.

According to some embodiments, the means are adapted to constantly tag the at least one of surgical tool within the surgical environment.

According to some embodiments, the preferred tool function $g_{16}(t)$ comprises a communicable database. The database stores a preferred tool; and the preferred tool function is adapted to output instructions to the tracking subsystem to instruct the maneuvering subsystem to direct the endoscope to the preferred tool.

According to some embodiments, the system further comprises means adapted to re-tag the at least one of the surgical tools until a desired tool is selected.

According to some embodiments, the system further comprises means adapted to toggle the surgical tools. According to some embodiments, the toggling is performed manually or automatically.

According to different embodiments of the present invention, the weighting functions $\alpha_i(t)$ are time-varying functions (or constants), the value of which is determined by the operator or the output of the instructing functions $g_i(t)$. For example, if a specific function $g_i(t)$ detected an important event or object, its weighting functions $\alpha_i(t)$ may be adjusted in order to elevate the chances that the maneuvering function $f(t)$ will instruct the maneuvering subsystem to move the endoscope towards this important event or object.

According to different embodiments of the present invention, the tracking subsystem may implement various image processing algorithms which may also be algorithms that are well known in the art. The image processing algorithms may be for example: image stabilization algorithms, image improvement algorithms, image compilation algorithms, image enhancement algorithms, image detection algorithms, image classification algorithms, image correlations with the cardiac cycle or the respiratory cycle of the human body, smoke reduction algorithms, vapor reduction algorithms, steam reduction algorithms and any combination thereof. Smoke, vapor and steam reduction algorithms may be needed as it is known that, under certain conditions, smoke, vapor or steam may be emitted by or from the endoscope. The image processing algorithm may also be implemented and used to analyze 2D or 3D representations which may be rendered from the real-time images of the surgical environment.

According to different embodiments, the endoscope may comprise an image acquisition device selected from a group consisting of: a camera, a video camera, an electromagnetic sensor, a computer tomography imaging device, a fluoroscopic imaging device, an ultrasound imaging device, and any combination thereof.

According to some embodiments, the system may also comprise a display adapted to provide input or output to the operator regarding the operation of the system. The display may be used to output the acquired real-time images of a surgical environment with augmented reality elements. The display may also be used for the definition of the region of interest by the operator.

According to some embodiments, the endoscope may be controlled be an endoscope controller for performing operations such as: acquiring the real-time images and zooming-in to a predetermined area. For example, the endoscope controller may cause the endoscope to acquire the real-time images in correlation with the cardiac cycle or the respiratory cycle of a human body.

According to different embodiments, the data processor of the present invention may operate a pattern recognition algorithm for assisting the operation of the instructing functions $g_i(t)$. The pattern recognition algorithm may be used as part of the image processing algorithm.

It should be emphasized that all of the above (and the following disclosure) is enabled by constantly monitoring and locating/identifying the 3D spatial location of each element/tool in the surgical environment.

The identification is provided by conventional means known to any skilled in the art (e.g., image processing, optical means etc.).

The present invention further discloses a method for assisting an operator to perform a surgical procedure, comprising steps of:
- a. providing a surgical controlling system, comprising: (i) at least one surgical tool; (ii) at least one location estimating means; and (iii) a controller having a processing means communicable with a database;
- b. inserting the at least one surgical tool into a surgical environment of a human body;
- c. estimating the location of the at least one surgical tool within the surgical environment; and,
- d. controlling the spatial position of the at least one surgical tool within the surgical environment by means of the controller; wherein the step of controlling is performed by storing a predetermined set of rules in the database where the predetermined set of rules comprises ALLOWED and RESTRICTED movements of the at least one surgical tool, such that the spatial position of the at least one surgical tool is controlled by the controller according to the ALLOWED and RESTRICTED movements.

The present invention also discloses a method for assisting an operator to perform laparoscopic surgery on a human body. The method comprises steps of:
- a. providing a surgical tracking system, comprising: (i) at least one endoscope adapted to acquire real-time images of a surgical environment within the human body; (ii) a maneuvering subsystem in communication with the endoscope; and (iii) a tracking subsystem in communication with the maneuvering subsystem, the tracking subsystem comprising a data processor;
- b. performing real-time image processing of the surgical environment;
- c. controlling the maneuvering subsystem via the tracking subsystem, thereby directing and modifying the spatial position of the endoscope to a region of interest according to input received from a maneuvering function f(t);

the maneuvering function f(t) is adapted to (a) receive input from at least two instructing functions $g_i(t)$, where i is 1, . . . , n and n≥2; where t is time; i and n are integers; and (b) to output instructions to the maneuvering subsystem based on the input from the at least two instructing functions $g_i(t)$, so as to spatially position the endoscope to the region of interest.

It should be emphasized that all of the above (and the following disclosure) is enabled by constantly monitoring and locating/identifying the 3D spatial location of each element/tool in the surgical environment.

The identification is provided by conventional means known to any skilled in the art (e.g., image processing, optical means etc.).

The present invention further discloses a surgical controlling system, comprising:
- a. at least one endoscope adapted to provide real-time image of surgical environment of a human body;
- b. at least one processing means, adapted to real time define n element within the real-time image of surgical environment of a human body; each of the elements is characterized by predetermined characteristics;
- c. image processing means in communication with the endoscope, adapted to image process the real-time image and to provide real time updates of the predetermined characteristics;
- d. a communicable database, in communication with the processing means and the image processing means, adapted to store the predetermined characteristics and the updated characteristics;

the system is adapted to notify the operator if the updated characteristics are substantially different from the predetermined characteristics.

Thus, according to this embodiment, each element in the surgical environment is characterized. The characteristics are constantly monitored. If the characteristics change substantially, the system notifies the user.

For example, the element that is monitored could be an organ and the characteristic being monitored is its contours. Once the contours have significantly changed (which could imply that the organ has been e.g., carved) the system alerts the user.

It should be emphasized that all of the above is enabled by constantly monitoring and locating/identifying the 3D spatial location of each element/tool in the surgical environment.

The identification is provided by conventional means known to any skilled in the art (e.g., image processing, optical means etc.).

According to another embodiment, the predetermined characteristics are selected from a group consisting of: color of the element, 3D spatial location of the element, contours of the element, and any combination thereof.

According to another embodiment, the system additionally comprises at least one surgical tool adapted to be inserted into a surgical environment of a human body for assisting a surgical procedure.

According to another embodiment, the system additionally comprises at least one location estimating means adapted to estimate the location of the at least one surgical tool.

According to another embodiment, the system additionally comprises a controller having a processing means communicable with a database, the controller adapted to control the spatial position of the at least one surgical tool.

The present invention further provides a method for controlling surgery, comprising steps of:
a. obtaining a system comprising:
  i. at least one endoscope adapted to provide real-time image of a surgical environment in a human body;
  ii. at least one processing means, adapted to define in real time n elements within the real-time image of the surgical environment of a human body, n is an integer greater than 0; each of the elements characterized by predetermined characteristics;
  iii. image processing means in communication with the endoscope, adapted to process the real-time image and to provide real time updates of the predetermined characteristics;
  iv. a communicable database, in communication with the processing means and the image processing means, adapted to store the predetermined characteristics and the updated characteristics;
b. providing a real-time image of a surgical environment in a human body;
c. defining the n elements;
d. characterizing each of the elements by the predetermined characteristics;

e. providing a real-time update of the predetermined characteristics;
f. notifying the user if the updated characteristics are substantially different from the predetermined characteristics.

According to another embodiment, the predetermined characteristics are selected from a group consisting of: color of the element, 3D spatial location of the element, contours of the element and any combination thereof.

According to another embodiment, the method additionally comprises a step of providing at least one surgical tool adapted to be inserted into a surgical environment of a human body for assisting a surgical procedure.

According to another embodiment, the method additionally comprises a step of providing at least one location estimating means adapted to estimate the location of the at least one surgical tool.

According to another embodiment, the method additionally comprises a step of providing a controller having a processing means communicable with a database, the controller adapted to control the spatial position of the at least one surgical tool.

According to another embodiment, the system of the present invention additionally comprises an image processing unit. According to another embodiment, the image processing unit is adapted to reduce 'noise' from the received image by reducing the visibility in the image of the smoke caused by e.g., coagulation. According to another embodiment, the image processing unit is adapted to reduce 'noise' from the received image by reducing the visibility in the image of vapor or steam accumulated on the endoscope.

According to another embodiment, the right tool function is adapted to instruct the maneuvering subsystem to constantly position the endoscope to track the movement of the right tool (i.e., the tool positioned to the right of the endoscope).

According to another embodiment, the left tool function is adapted to instruct the maneuvering subsystem to constantly position the endoscope to track the movement of the left tool (i.e., the tool positioned to the left of the endoscope).

According to another embodiment, the field of view function is adapted to instruct the maneuvering subsystem to constantly position the endoscope so as to maintain a constant field of view.

According to another embodiment, the no fly zone function is adapted to define (either real-time, during the procedure or prior to the procedure) a no fly zone and to instruct the maneuvering subsystem to restrict entrance of the endoscope to the no fly zone.

According to another embodiment, the most used tool function is adapted to define (either real-time, during the procedure or prior to the procedure) which tool is the most used tool (i.e., the tool which is moved the most during the procedure) and to instruct the maneuvering subsystem to constantly position the endoscope to track the movement of the most-used tool.

The following figures provide examples of several of the above mentioned rules and functions.

Reference is made now to FIG. 1, which is a general schematic view of a specific embodiment of a surgical tracking system 100. In this figure are illustrated surgical instruments 17b and 17c and an endoscope 21 which may be maneuvered by means of maneuvering subsystem 19 according to the instructions received from a tracking subsystem operable by computer 15.

According to one embodiment of the present invention as defined in the above, the user may define the field of view function as constantly monitoring at least one of surgical instruments 17b and 17c.

According to this embodiment, the surgical tracking system 100 may also comprise one or more button operated wireless transmitters 12a, which transmit, upon activation, a single code wave 14 through aerial 13 to connected receiver 11 that produces a signal processed by computer 15, thereby directing and modifying the spatial position of endoscope 21 to the region of interest, as defined by the field of view function.

Alternatively, according to the proximity rule, if the distance between the surgical instruments 17b and 17c is smaller than a predetermined distance (as defined by the collision prevention rule), the system alerts the user that any movement of either one of the surgical instruments 17b and 17c that will reduce the distance is a RESTRICTED movement.

Figure 2:
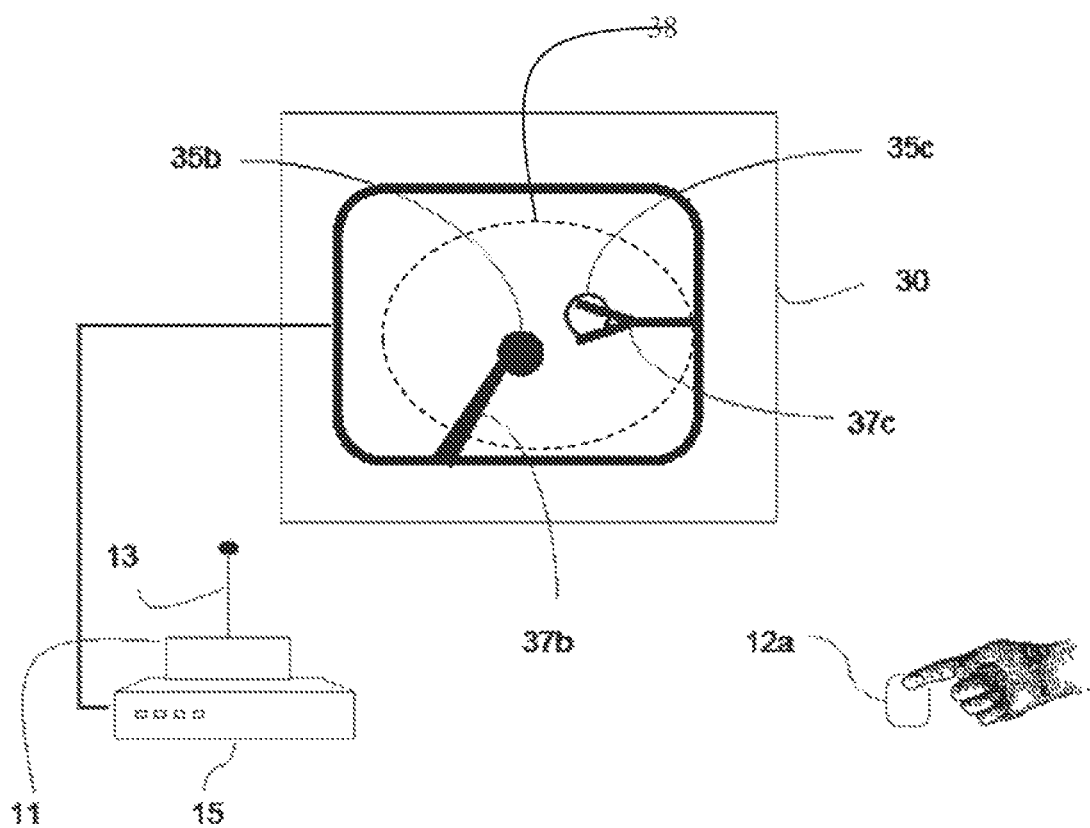

Reference is made now to FIG. 2, which schematically illustrates the operation of the present invention. According to this figure, the system of the present invention comprises a display 30 in which the overall procedure is presented to the operator. In this figure an endoscope is automatically spatially repositioned towards a region of interest 38.

The region of interest to which the endoscope is repositioned comprises tools 37b and 37c, which are automatically detected by the tracking subsystem (not shown) of computer 15. According to different embodiments, the repositioning of the endoscope may be automatic or semi-automatic. For example, according to FIG. 2, a light depression of the button on generic code-emitting wireless transmitter 12a causes transmission of a code that is received by receiver aerial 13 communicated through connected receiver 11 to computer 15. This operation causes the endoscope of the present invention to be spatially repositioned to the predefined region of interest (e.g., the location in which the working tools are located). According to this embodiment of the present invention, the operator may define the region of interest as the region in which a tip 35b of tool 37b is found.

According to another embodiment, the operator can define one of the surgical instruments 17b and 17c as a preferred tool. Thus, according to the preferred tool rule, the endoscope will constantly monitor and track the body of the selected tool. According to another embodiment, the user can define the preferred tool rule to constantly reposition the endoscope on the tip of the same (see tip 35b in FIG. 2).

According to the embodiment illustrated in FIG. 2, the activation of the system is provided by a button that signals to the system that it is to be activated.

According to another embodiment of the present invention, the button can be coupled to the desired tool to be monitored, such that the endoscope will monitor the tool to which the button is coupled (and from which signal 12a is emitted).

Referring again to FIG. 2, once a region of interest has been defined, the tracking subsystem is adapted to look for tip 35b within the region of interest by performing image processing. When tip 35b is not detected by the tracking subsystem, the system can move the endoscope in a forward direction along a predefined track. When tip 35b is detected by the tracking subsystem, the endoscope automatically focuses of the region of interest.

While performing the surgery, the surgeon often changes the position of his tools and even their insertion point. In order to realize a position and range system, many well-known technologies may be used. For example, the tools may be equipped with switches. If the switches emit wireless signals, then an array of antennas may be used to compare the power of the signal received at each antenna in order to determine the angle of the switch and its approximate range to the camera holder mechanism. If the switch emits ultrasound then ultrasound-sensitive microphones can be used to triangulate the position of the switch. The same is true for a light-emitting switch. In a preferred embodiment of the invention, a single wireless emission code is utilized and choice is achieved by a visible graphic representation on a conventional viewing screen.

In another preferred embodiment, each instrument is fitted with a unique code wireless transmitter, and selection is achieved by depressing its button.

According to different embodiments, the tracking subsystem of the present invention may be used in any conventional camera-assisted laparoscopic surgery system which comprises an endoscope. Upon depression of at least one button on a transmitter for activating the tracking subsystem, either a generic or a unique code is transmitted to a receiving device connected to a computer that instructs the maneuvering subsystem to reposition the endoscope to a region of interest.

For example, the system of the present invention may be used to allow an operator (e.g., a surgeon) to present the surgical instrument to surgical colleagues and staff. By identifying the surgical instrument via the tracking subsystem, the endoscope directs the view to the predefined region of interest.

According to some embodiments, the tracking subsystem may identify a surgical tool after characterization of the same prior to the surgery. The characteristics of the surgical tool may be stored in a database for further use in the image processing algorithm. Upon depression of at least one button, the tracking subsystem may instruct the maneuvering subsystem to move the endoscope so as to achieve the desired focus on a specific region of interest.

The device of the present invention has many technological advantages, among them:
Simplifying the communication interface between surgeon and mechanical assistants.
Seamless interaction with conventional computerized automated endoscope systems.
Simplicity of construction and reliability.
User-friendliness.

Additional features and advantages of the invention will become apparent from the following drawings and description.

To improve the control of the endoscope, the system of the present invention comprises a maneuvering subsystem. Many maneuvering systems are known in the art and many of them have several degrees of freedom:
(a) one degree of freedom enables the system to move the endoscope or laparoscope forward and backwards;
(b) another degree of freedom enables the system to move the endoscope or laparoscope in a zoom movement i.e. in and out of the patient's body through the penetration point;
(c) another degree of freedom enables the system to move the endoscope or laparoscope to the right and left;
(d) another degree of freedom enables the system to fine tune endoscope or laparoscope movements to the right and to the left;
(e) another degree of freedom enables the system to fine tune endoscope or laparoscope movements forward and backwards;
(f) another degree of freedom enables the system to rotate the camera with respect to the endoscope's long axis. This degree of freedom is necessary to keep the horizon of the image from changing when using an endoscope with "angled edge".

Such maneuvering systems are utilized by the present invention so as to reposition the endoscope to the desired location.

The present invention is utilized to improve upon the interface between surgeon and automated assistants by communicating the surgeon's current instrument of choice, supplying location data to the image processing computing software, thereby directing the endoscope to focus on that choice. The technology relies on marrying a conventional laparoscopic system with data obtained from e.g., small RF transmitters attached to a surgical tool or, alternatively, data obtained from light emitters (e.g., LED bulbs) attached to a surgical tool.

It will be apparent to one skilled in the art that there are several embodiments of the invention that differ in details of construction, without affecting the essential nature thereof, and therefore the invention is not limited by that which is illustrated in the figures and described in the specification, but only as indicated in the accompanying claims, with the proper scope determined only by the broadest interpretation of the claims.

Figure 3A:
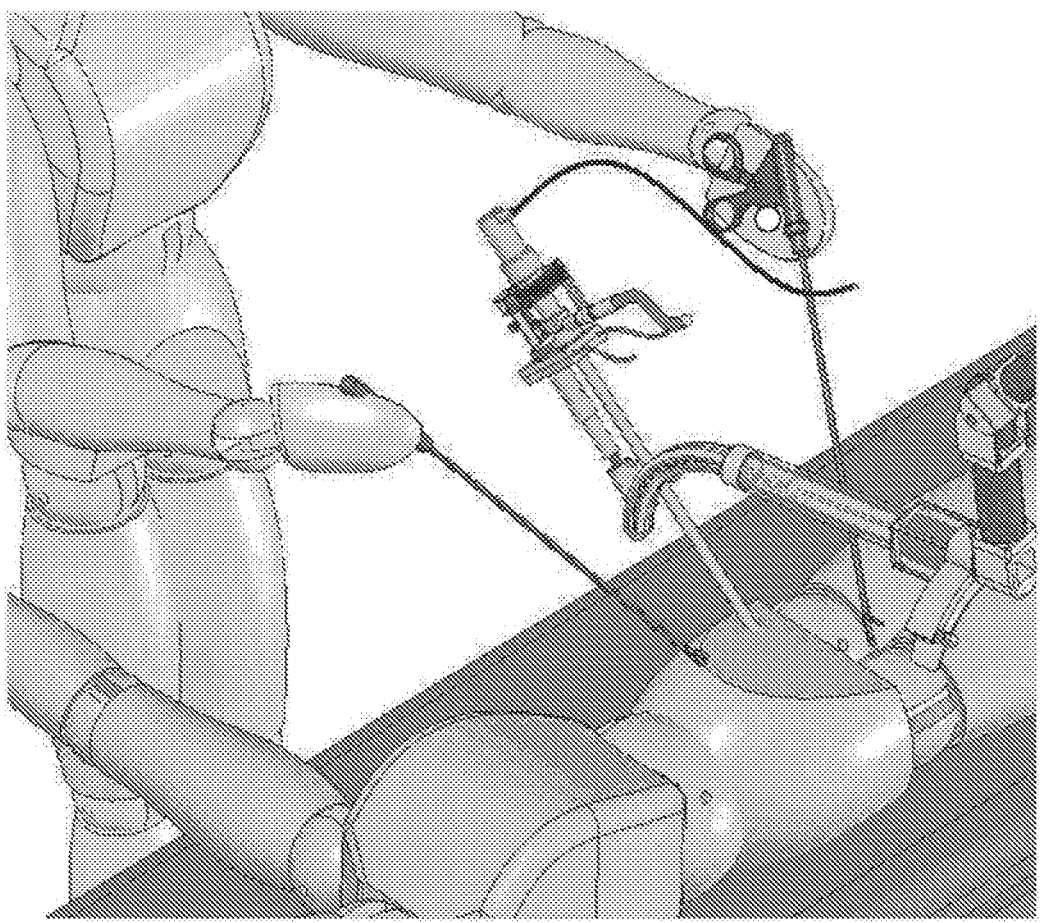
FIG. 3A shows an example of using the location system in abdominal laparoscopic surgery.

FIG. 3A shows an example of using the system of the present invention in abdominal laparoscopic surgery.

Figure 3B:
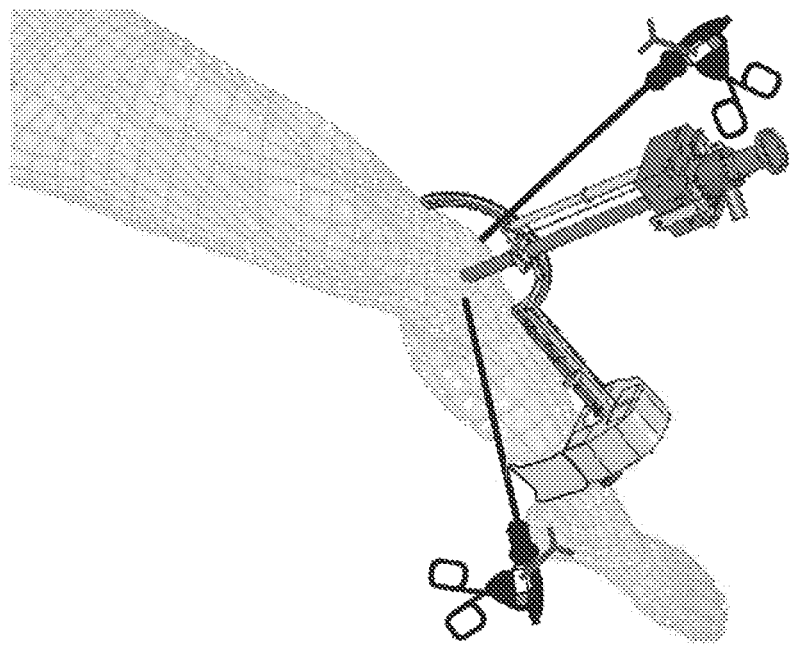
FIG. 3B shows an example of using the location system in knee endoscopic surgery; and, FIG. 3C shows an example of using the location system in shoulder endoscopic surgery.

FIG. 3B shows an example of using the system of the present invention in knee endoscopic surgery.

Figure 3C:
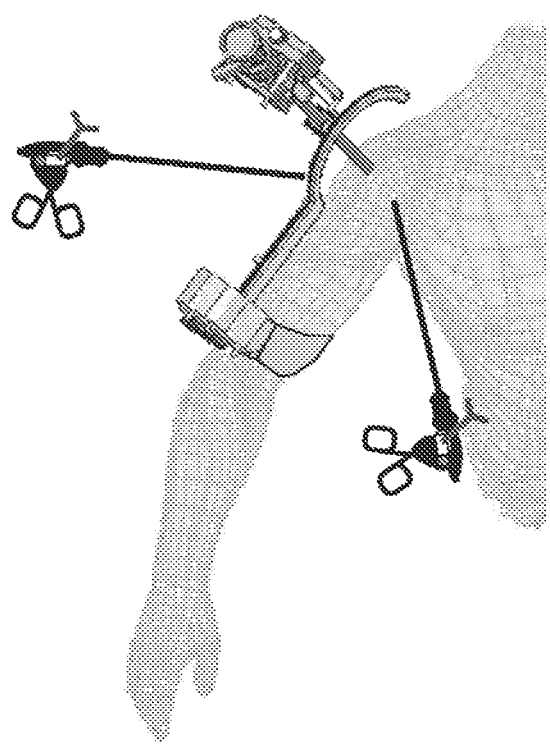

Lastly, FIG. 3C shows an example of using the system of the present invention in shoulder endoscopic surgery.

EXAMPLES

Examples are given in order to prove the embodiments claimed in the present invention. The example, which is a clinical test, describes the manner and process of the present invention and set forth the best mode contemplated by the inventors for carrying out the invention, but are not to be construed as limiting the invention.

In the examples below, similar numbers refer to similar parts in all of the figures.

Example 1—Tracking System with Collision Avoidance System

One embodiment of such a rule-based system will comprise the following set of commands:
Detection (denoted by Gd):
Gd1 Tool location detection function
Gd2 Organ (e.g. Liver) detection function
Gd3 Movement (vector) calculation and estimation function
Gd4 Collision probability detection function
Tool Instructions (denoted Gt):
Gt1 Move according to manual command
Gt2 Stop movement
The scenario—manual move command by the surgeon:
Locations Gd1(t) and Gd2(t) are calculated in real time at each time step (from an image or location marker).

Tool movement vector Gd3(t) is calculated from Gd1(t) as the difference between the current location and at least one previous location (probably also taking into account previous movement vectors).

The probability of collision—Gd4(t)—is calculated, for example, from the difference between location Gd1 and location Gd2 (the smaller the distance, the closer the proximity and the higher the probability of collision), from movement vector Gd3(t) indicating a collision, etc.

Figure 4A:
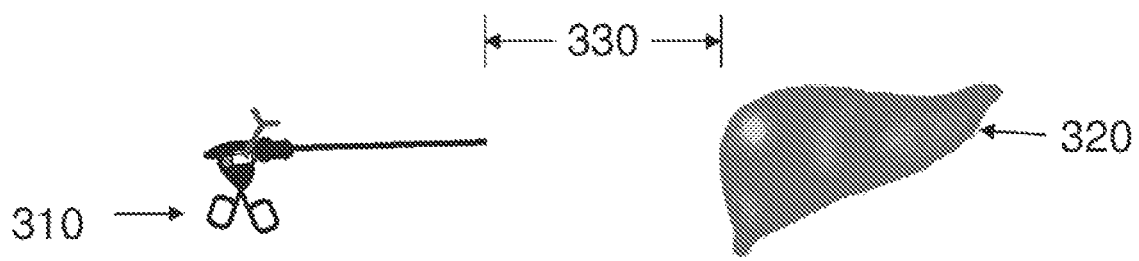
FIG. 4A-D schematically illustrates operation of an embodiment of a tracking system with collision avoidance system.
Figure 4B:
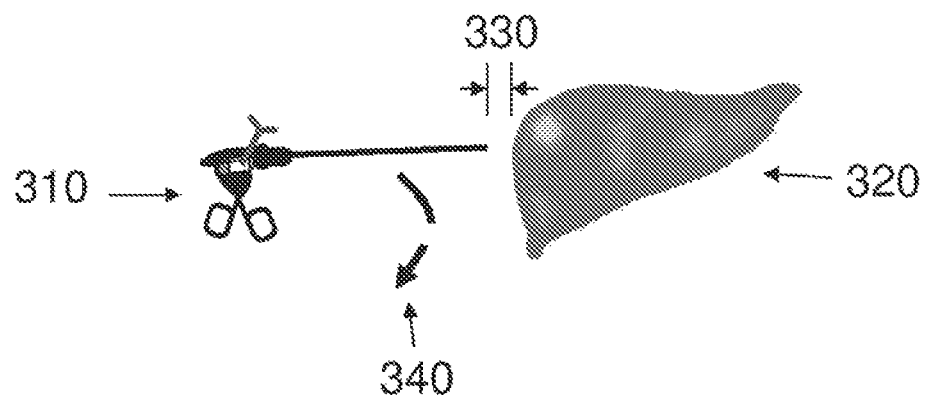
Figure 4C:
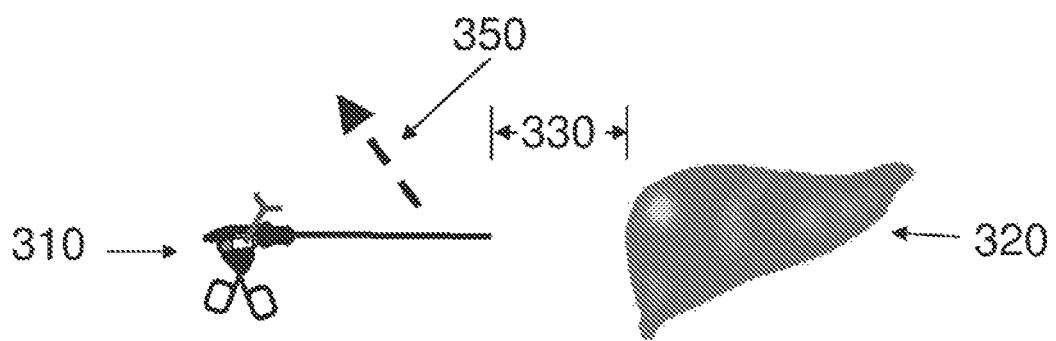
Figure 4D:
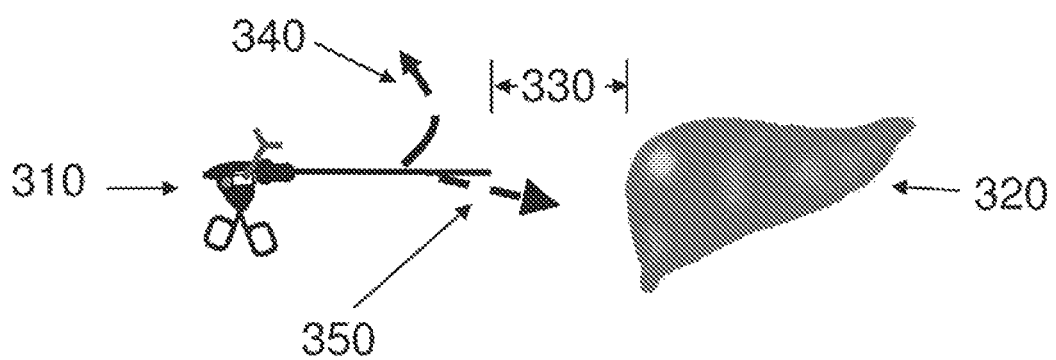

Tool Instructions Gt1 Weight function $\alpha_i(t)=1$ If Gt1 (t)<a predetermined threshold and 0 otherwise Tool Instructions Gt2 Weight function $\alpha_2(t)=1$ If Gt2 (t)>a predetermined threshold and 0 otherwise Tool Instructions=$\alpha_i(t)Gt1+\alpha_2(t)*Gt2(t)$;

In reference to FIG. 4A-D, which shows, in a non-limiting manner, an embodiment of a tracking system and collision avoidance system. The system tracks a tool 310 and the liver 320, in order to determine whether a collision between the tool 310 and the liver 320 is possible within the next time step. FIGS. 4A and 4B show how the behavior of the system depends on the distance 330 between the tool 310 and the liver 320, while FIGS. 4C and 4D show how movement of the tool 310 affects the behavior. In FIG. 4A, the distance 330 between the tool 310 and the liver 320 is large enough that a collision is not possible in that time step. Since no collision is possible, no movement of the tool is commanded. In FIG. 4B, the distance 330 between the tool 310 and the liver 320 is small enough that a collision is likely. In the embodiment illustrated, a movement 340 is commanded to move the tool 310 away from the liver 320. In other embodiments, the system does not command movement 340; in such embodiments, the tool 310 will remain close to the liver 320. In yet other embodiments, the system warns/signals the operator that the tool close to the liver, but does not command movement 340 away from the liver. Such a warning/signaling can be visual or aural, using any of the methods known in the art.

FIGS. 4C and 4D illustrate schematically the effect of the movement of tool 310 on the collision avoidance system. In FIGS. 4C and 4D, the tool 310 is close enough to the liver 320 that a collision between the two is possible. If the system tracked only the positions of the tool 310 and the liver 320, then motion of the tool 310 away from the liver 320 would be commanded. FIG. 4C illustrates the effect of a movement 350 that would increase the distance between tool 310 and liver 320. Since the movement 350 is away from liver 320, no collision is possible in this time step and no movement of the tool 310 is commanded.

In FIG. 4D, tool 310 is the same distance from liver 320 as in FIG. 4C. However, in FIG. 4D, the movement 350 of the tool 310 is toward the liver 320, making a collision between tool 310 and liver 320 possible. In some embodiments, a movement 340 is commanded to move the tool 310 away from the liver 320. In other embodiments, the system prevents movement 350, but does not command movement 340; in this embodiment the tool 310 will remain close to the liver 320. In yet other embodiments, the system warns the operator that move is RESTRICTED, but does not restrict movement 350 or command movement 340 away from the liver. Such a warning can be visual or aural, using any of the methods known in the art.

As a non-limiting example, in an operation on the liver, the collision detection function can warn the operator that a collision between a tool and the liver is likely but not prevent the collision. In an operation on the gall bladder, the collision detection function can prevent a collision between the tool and the liver, either by preventing the movement or by commanding a movement redirecting the tool away from the liver, Example 2—Tracking System with Soft Control—Fast Movement when Nothing is Nearby, Slow Movement when Something is Close One embodiment of such rule-based system comprises the following set of commands:
Detection (denoted by Gd):
Main Tool location detection function (denoted by GdM);
Gd-tool1-K—Tool location detection function;
Gd-organ2-L—Organ (e.g. Liver) detection function;
Gd3 Main Tool Movement (vector) calculation and estimation function;
Gd4 Proximity probability detection function;
Tool Instructions (denoted Gt):
Gt1 Movement vector (direction and speed) according to manual command
The scenario—manual move command by the surgeon:
Locations GdM(t), Gd-tool1-K(t) and Gd-organ2-L(t) are calculated in real time at each time step (from image or location marker).
Main Tool Movement Vector Gd3(t) is calculated per GdM (t) as the difference between the current location and at least one previous location (probably also taking into account previous movement vectors)
The proximity of the main tool to other tools—Gd4(t)—is calculated, for example, as the smallest of the differences between the main tool location and the other tools' locations.
Tool Instructions Gt1 Weight function $\alpha_1(t)$ is proportional to tool proximity function Gd4(t), the closer the tool the slower the movement so that, for example $\alpha_2(t)=Gd4/\text{maximum}(Gd4)$ or $\alpha_2(t)=\log(Gd4/\text{maximum}(Gd4))$ where maximum(Gd4) is the maximum distance which is likely to result in a collision given the distances, the speed of the tool and the movement vector.

Tool Instructions=$\alpha_1(t)*Gt1$.

Example 3—Tracking System with No-Fly Rule/Function

In reference to FIG. 5A-D, which shows, in a non-limiting manner, an embodiment of a tracking system with no-fly rule. The system tracks a tool 310 with respect to a no-fly zone (460), in order to determine whether the tool will enter the no-fly zone (460) within the next time step. In this example, the no-fly zone 460 surrounds the liver.

Figure 5A:
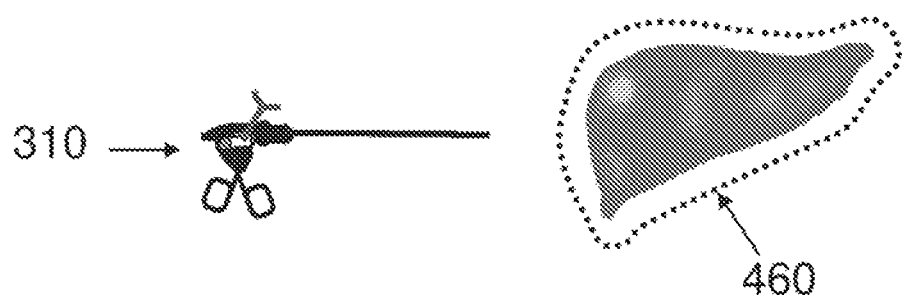
FIG. 5A-D schematically illustrates operation of an embodiment of a tracking system with no fly zone rule/function.
Figure 5B:
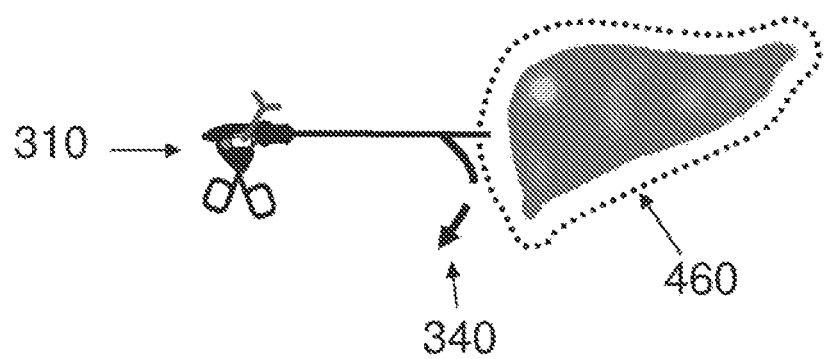
Figure 5C:
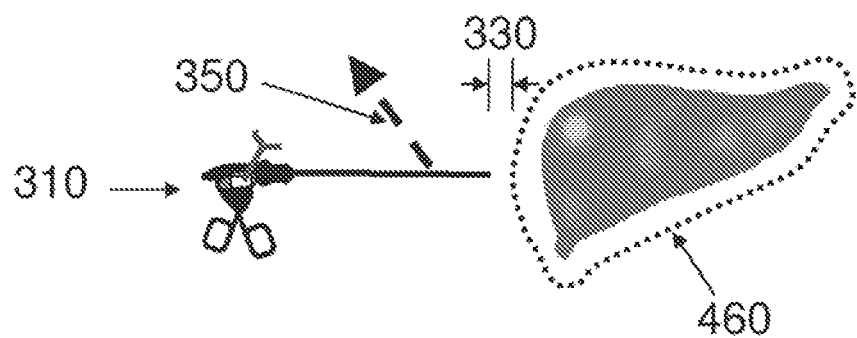
Figure 5D:
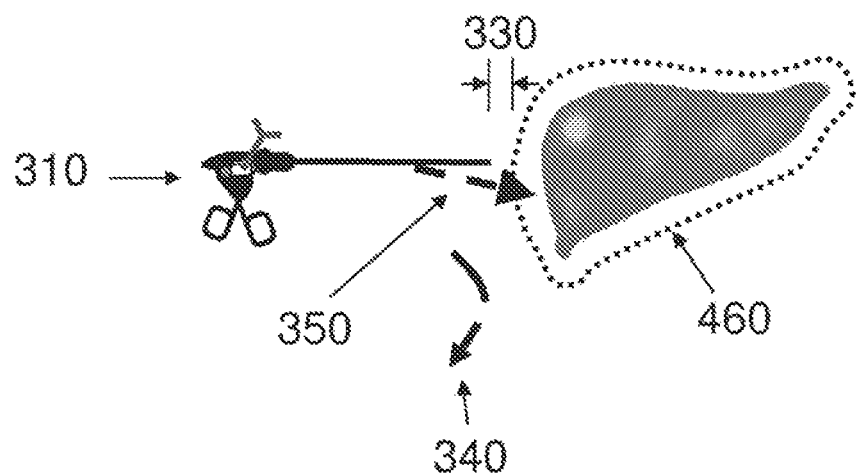

FIGS. 5A and 5B show how the behavior of the system depends on the location of the tool tip with respect to the no-fly zone, while FIGS. 5C and 5D show how movement of the tool affects the behavior.

In FIG. 5A, the tool 310 is outside the no-fly zone rule/function 460 and no movement of the tool is commanded. In FIG. 5B, the tool 310 is inside the no-fly zone 460.

The no-fly zone rule/function performs as follows:
In the embodiment illustrated, a movement 340 is commanded to move the tool 310 away from the no-fly zone 460. In other embodiments, the system prevents movement further into the no-fly zone (refers as movement 350, see FIG. 5D), but does not command movement 340; in such embodiments, the tool 310 will remain close to the no-fly zone 460.

In yet other embodiments, the system warns/signals the operator that the move is RESTRICTED, but does not restrict movement further into the no-fly zone or command movement 340 away from the no-fly zone 460. Such a warning/signaling can be visual or aural, using any of the methods known in the art.

FIGS. 5C and 5D illustrate schematically the effect of the tool's movement on operation of the no-fly zone rule/function. In FIGS. 5C and 5D, the tool 310 is close enough to the no-fly zone 460 (distance 330 is small enough) that it is possible for the tool to enter the no-fly zone during the next time step. FIG. 5C illustrates the effect of a movement 350 that would increase the distance between tool 310 and no-fly zone 460. Since the movement 350 is away from no-fly zone 460, no collision is possible in this time step and no movement of the tool 310 is commanded.

In FIG. 5D, tool 310 is the same distance from no-fly zone 460 as in FIG. 5C. However, in FIG. 5D, the movement 350 of the tool is toward no-fly zone 460, making it possible for tool 310 to enter no-fly zone 460. In the embodiment illustrated, a movement 340 is commanded to move the tool 310 away from the no-fly zone 460. In other embodiments, the system prevents movement 350, but does not command movement 340; in such embodiments, the tool 310 will remain close to the no-fly zone 460. In yet other embodiments, the system warns/signals the operator that the move is RESTRICTED, but does not restrict movement 350 or command movement 340 away from the no-fly zone rule/function 460. Such a warning/signaling can be visual or aural, using any of the methods known in the art.

Example 4—Tracking System with Preferred Volume Zone Rule/Function

In reference to FIG. 6A-D, which shows, in a non-limiting manner, an embodiment of a tracking system with a preferred volume zone function/rule.

The system tracks a tool 310 with respect to a preferred volume zone (570), in order to determine whether the tool will leave the preferred volume (570) within the next time step.

Figure 6A:
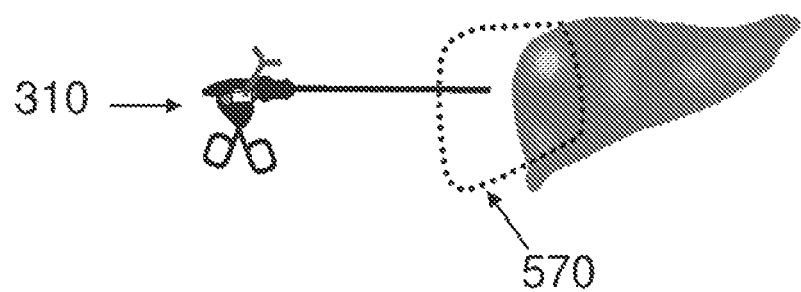
FIG. 6A-D schematically illustrates operation of an embodiment of a tracking system with preferred volume zone rule/function.
Figure 6B:
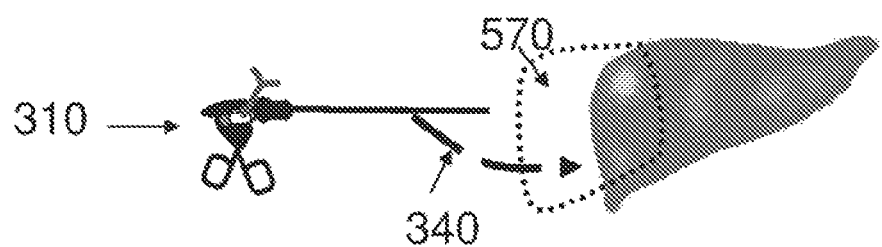

In this example, the preferred volume zone 570 extends over the right lobe of the liver. FIGS. 6A and 6B show how the behavior of the system depends on the location of the tool tip with respect to the preferred volume zone 570, while FIGS. 6C and 6D show how movement of the tool affects the behavior (i.e., the preferred volume zone rule/function).

In FIG. 6A, the tool 310 is inside the preferred volume zone 570 and no movement of the tool is commanded. In FIG. 6B, the tool 310 is outside the preferred volume zone 570.

In the embodiment illustrated, a movement 340 is commanded to move the tool 310 into the preferred volume zone 570. In other embodiments, the system does not command movement 340; in such embodiments, the tool 310 will remain close to but outside the preferred volume zone 570. In yet other embodiments, the system warns/signals the operator that the tool is outside the preferred volume zone 570, but does not move the tool. Such a warning/signaling can be visual or aural, using any of the methods known in the art.

Figure 6C:
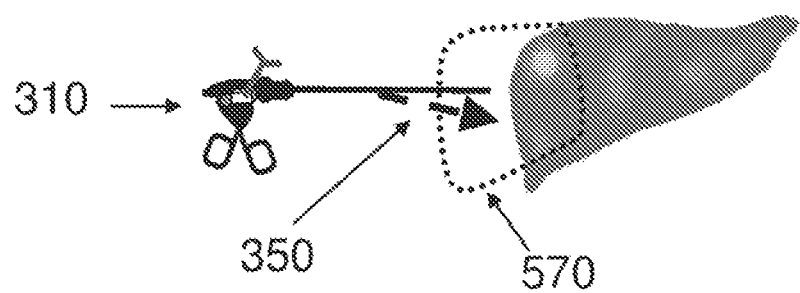
Figure 6D:
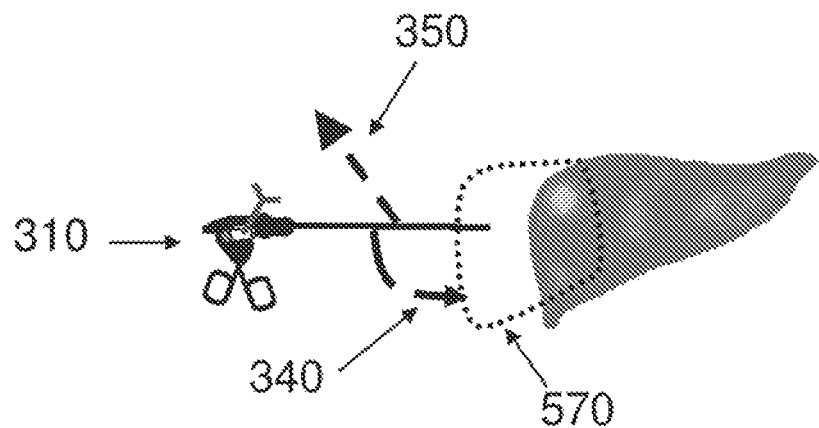

FIGS. 6C and 6D illustrate schematically the effect of the tool's movement on operation of the preferred volume rule/function. In FIGS. 6C and 6D, the tool 310 is close enough to the edge of preferred volume zone 570 that it is possible for the tool to leave the preferred volume zone during the next time step.

FIG. 6C illustrates the effect of a movement 350 that would take the tool 310 deeper into preferred volume zone 570. Since the movement 350 is into preferred volume 570, said movement is an allowed movement.

In FIG. 6D, the movement 350 of the tool is out of the preferred volume 570, making it possible for tool 310 to leave preferred volume 570.

According to one embodiment illustrated, a movement 340 is commanded to move the tool 310 into the preferred volume zone 570. In other embodiments, the system prevents movement 350, but does not command movement 340; in such embodiments, the tool 310 will remain within the preferred volume zone 570. In yet other embodiments, the system warns/signals the operator that the move is RESTRICTED, but does not restrict movement 350 or command movement 340 into the preferred volume zone 570. Such a warning/signaling can be visual or aural, using any of the methods known in the art.

Example 5—Organ/Tool Detection Function

Figure 7:
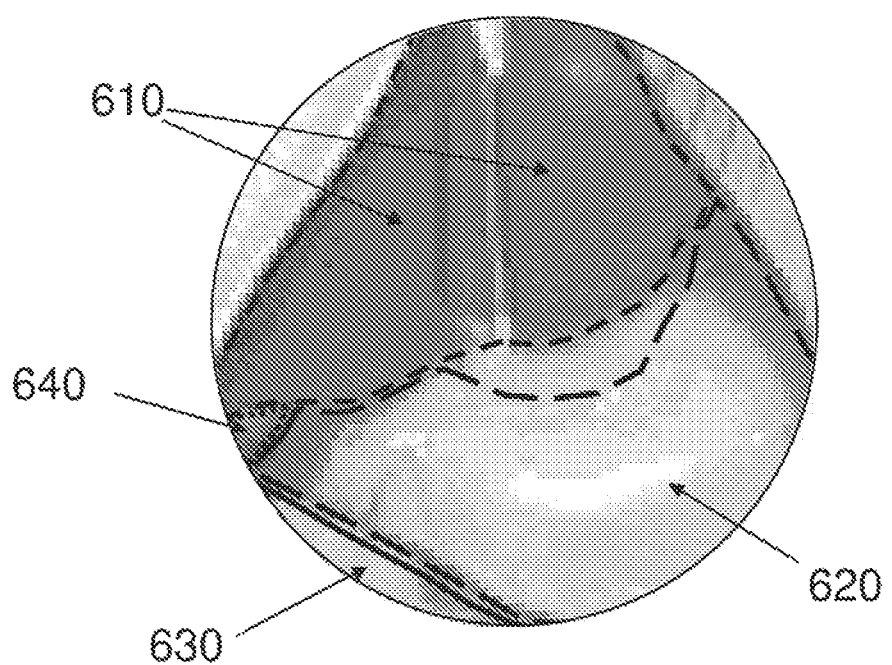
FIG. 7 schematically illustrates operation of an embodiment of the organ detection function/rule.

In reference to FIG. 7, which shows, in a non-limiting manner, an embodiment of an organ detection system (however, it should be noted that the same is provided for detection of tools, instead of organs).

For each organ, the 3D spatial positions of the organs stored in a database. In FIG. 7, the perimeter of each organ is marked, to indicate the edge of the volume of 3D spatial locations stored in the database.

In FIG. 7, the liver 610 is labeled with a short dashed line. The stomach 620 is labeled with a long-dashed line, the intestine 630 with a solid line and the gall bladder 640 is labeled with a dotted line.

In some embodiments, a label or tag visible to the operator is also presented. Any method of displaying identifying markers known in the art can be used. For non-limiting example, in an enhanced display, colored or patterned markers can indicate the locations of the organs, with the marker either indicating the perimeter of the organ or the area of the display in which it appears.

Example 6—Tool Detection Function

Figure 8:
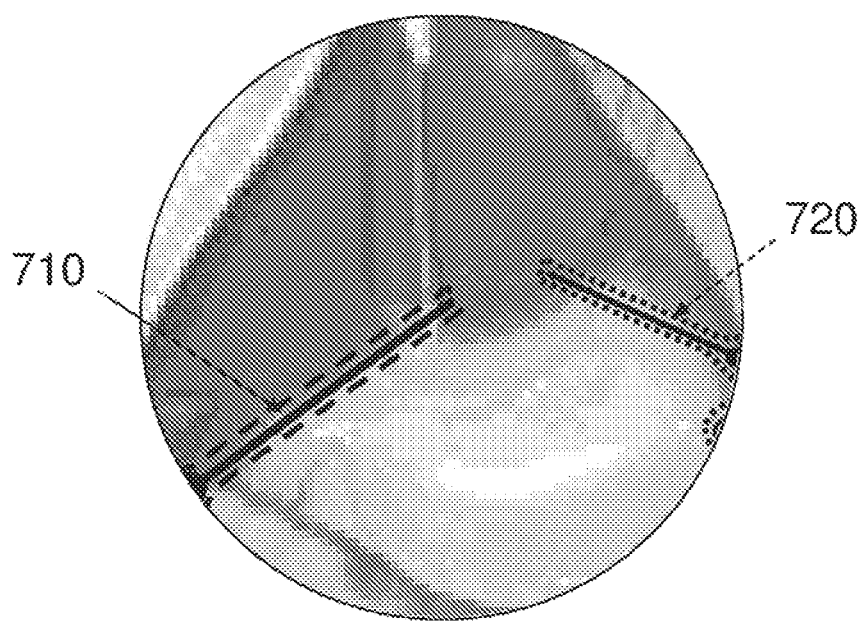
FIG. 8 schematically illustrates operation of an embodiment of the tool detection function/rule.

In reference to FIG. 8, which shows, in a non-limiting manner, an embodiment of a tool detection function. For each tool, the 3D spatial positions of the tools stored in a database. In FIG. 8, the perimeter of each tool is marked, to indicate the edge of the volume of 3D spatial locations stored in the database. In FIG. 8, the left tool 710 is labeled with a dashed line while the right tool 720 is labeled with a dotted line.

In some embodiments, a label or tag visible to the operator is also presented. Any method of displaying identifying markers known in the art can be used. For non-limiting example, in an enhanced display, colored or patterned markers can indicate the locations of the tools, with the marker either indicating the perimeter of the tool or the area of the display in which it appears.

Example 7—Movement Detection Function/Rule

Figure 9A:
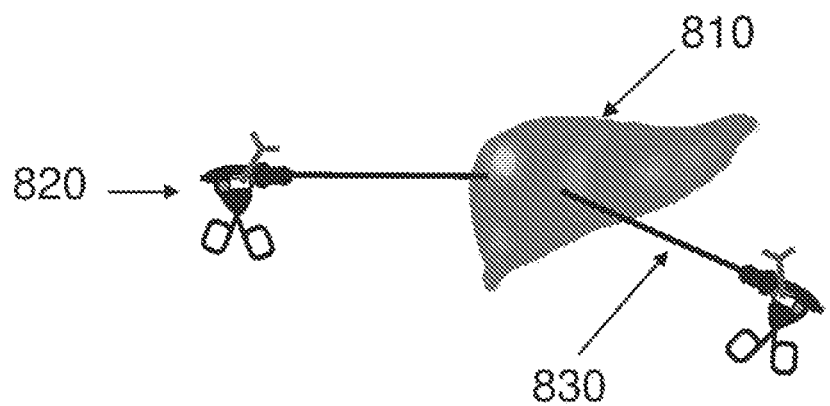
FIG. 9A-B schematically illustrates operation of an embodiment of the movement detection function/rule.
Figure 9B:
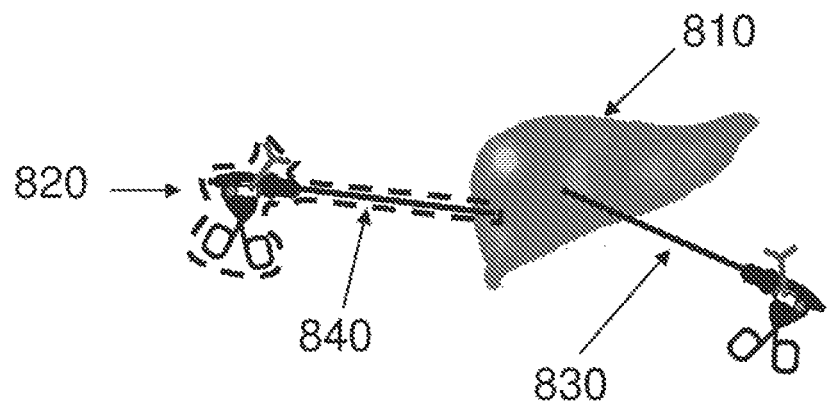

In reference to FIG. 9A-B, which shows, in a non-limiting manner, an embodiment of a movement detection function/rule. FIG. 9A schematically illustrates a liver 810, a left tool 820 and a right tool 830 at a time t. FIG. 9B schematically illustrates the liver 810, left tool 820 and right tool 830 at a later time t+Δt, where Δt is a small time interval. In this example, the left tool 820 has moved downward (towards the direction of liver 810) in the time interval Δt.

The system has detected movement of left tool 820 and labels it. This is illustrated schematically in FIG. 9B by a dashed line around left tool 820.

Example 8—Prediction Function

In reference to FIG. 10A-D, which shows, in a non-limiting manner, an embodiment of the above discussed prediction function.

Figure 10A:
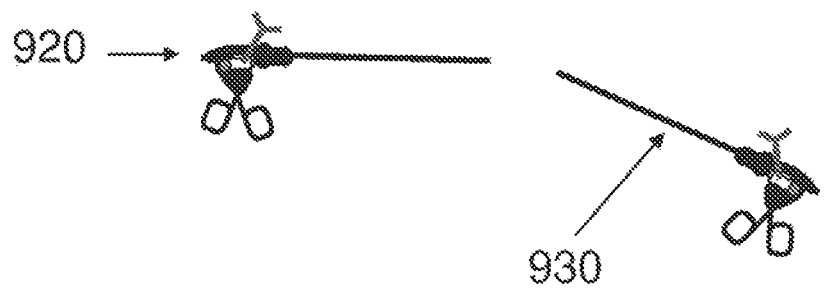
FIG. 10A-D schematically illustrates operation of an embodiment of the prediction function/rule.

FIG. 10A shows a left tool 920 and a right tool 930 at a time t.

Figure 10B:
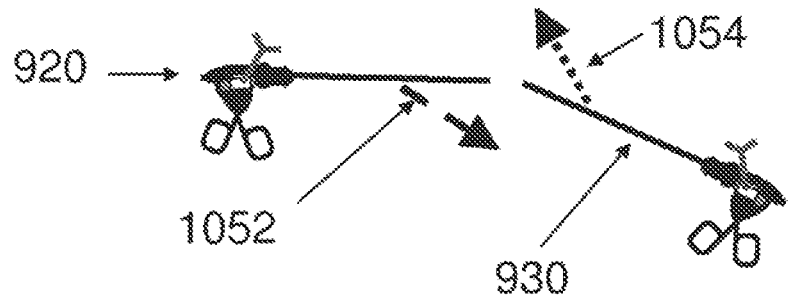
Figure 10C:
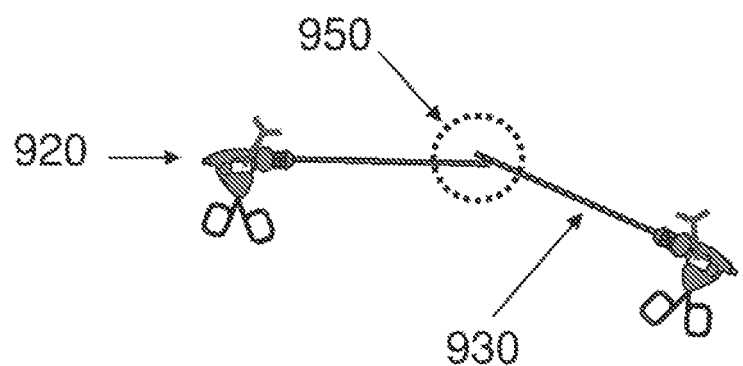

FIG. 10B shows the same tools at a later time t+Δt, where Δt is a small time interval. Left tool 920 is moving to the right and downward (1052, dashed arrow), while right tool 930 is moving to the left and upward (1054, dotted arrow). If the motion continues, then by the end of the next time interval, in other words, at some time between time t+Δt and time t+2Δt, the tools will collide, as shown by tool tips within the dotted circle 950 in FIG. 10C.

Figure 10D:
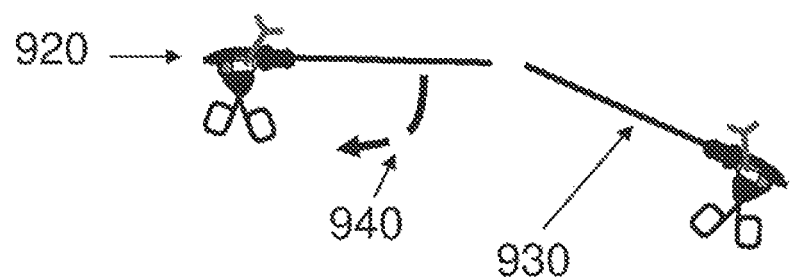

In this embodiment, the system automatically prevents predicted collisions and, in this example, as shown in FIG. 10D, the system applies a motion 940 to redirect left tool 920 so as to prevent the collision.

In other embodiments, the system warns/signals the operator that a collision is likely to occur, but does not alter the movement of any tool. Such a warning/signaling can be visual or aural, using any of the methods known in the art.

In other embodiments, the prediction function can be enabled to, for non-limiting example, alter the field of view to follow the predicted movement of a tool or of an organ, to warn of (or prevent) predicted motion into a no-fly zone, to warn of (or prevent) predicted motion out of a preferred zone.

Example 9—Right Tool Function/Rule

Figure 11:
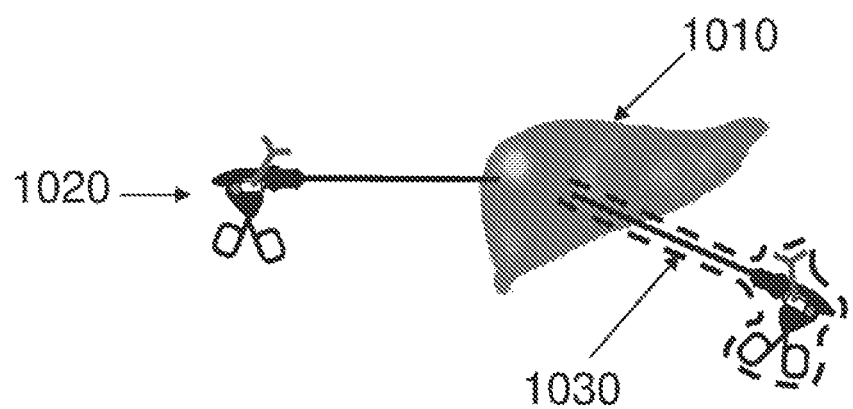
FIG. 11 schematically illustrates operation of an embodiment of the right tool function/rule.

In reference to FIG. 11, which shows, in a non-limiting manner, an embodiment of a right tool function. FIG. 11 schematically illustrates a liver 1010, a left tool 1020 and a right tool 1030. The right tool is labeled, illustrated schematically by the dashed line 1040, and its 3D spacial location is constantly and real-time stored in a database. Now, according to the right tool function/rule the endoscope constantly tracks the right tool.

It should be pointed out that the same rule/function applies for the left tool (the left tool function/rule).

Example 10—Field of View Function/Rule

Figure 12A:
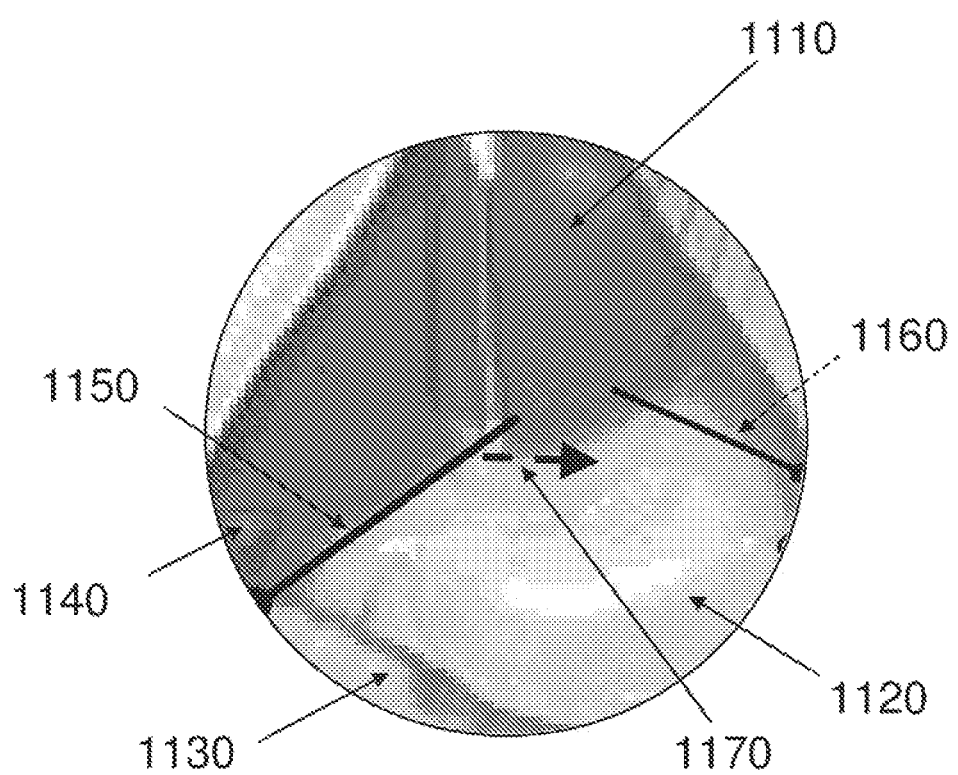
FIG. 12A-B schematically illustrates operation of an embodiment of the field of view function/rule.
Figure 12B:
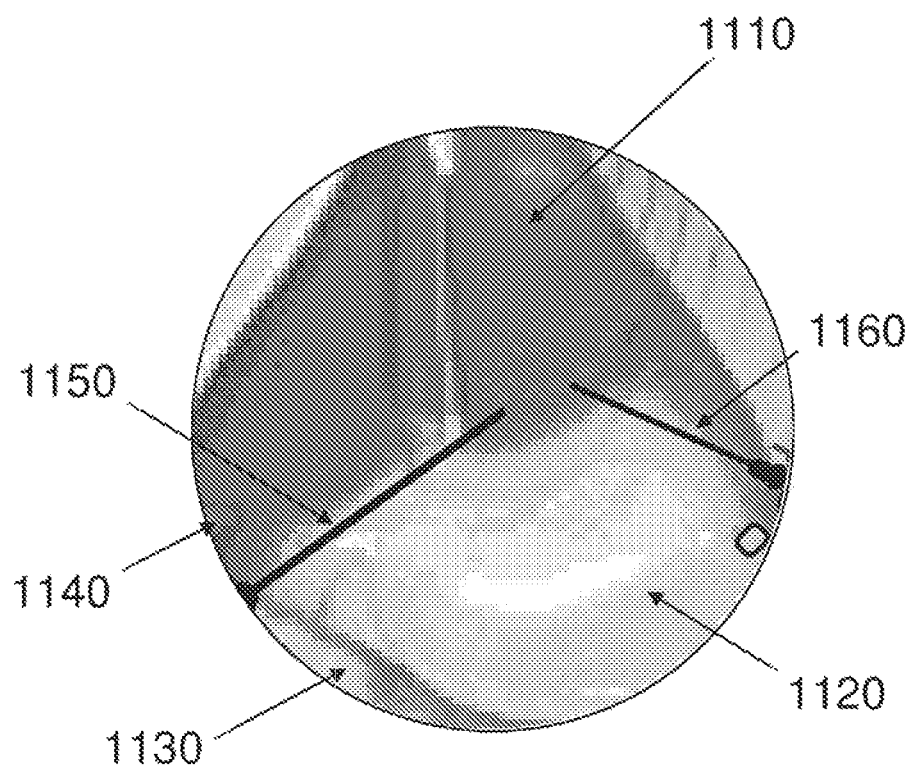

In reference to FIG. 12A-B, which shows, in a non-limiting manner, an embodiment of a field of view function/rule.

FIG. 12A schematically illustrates a field of view of the abdomen at a time t. In the field of view are the liver 1110, stomach 1120, intestines 1130 and gall bladder 1140.

The gall bladder is nearly completely visible at the left of the field of view. Two tools are also in the field of view, with their tips in proximity with the liver. These are left tool 1150 and right tool 1160. In this example, the field of view function/rule tracks left tool 1150. In this example, left tool 1150 is moving to the right, as indicated by arrow 1170.

FIG. 12B shows the field of view at time t+Δt. The field of view has moved to the right so that the tip of left tool 1150 is still nearly at the center of the field of view. It can be seen that much less of gall bladder 1140 is visible, as is less of the intestines, while more of right tool 1160 has entered the field of view. The liver 1110 and stomach 1120 have moved leftward in the image; more of the stomach is visible at the right edge of the field of view.

The field of view function/rule can be set to follow a selected tool, as in this example or to keep a selected organ in the center of the field of view. It can also be set to keep a particular set of tools in the field of view, zooming in or out as necessary to prevent any of the chosen tools from being outside the field of view.

Alternatively, the field of view function/rule defines n 3D spatial positions; n is an integer greater than or equal to 2; the combination of all of said n 3D spatial positions provides a predetermined field of view.

Each movement of the endoscope or the surgical tool within said n 3D spatial positions is an allowed movement and any movement of the endoscope or the surgical tool outside said n 3D spatial positions is a restricted movement.

Alternatively, said the field of view function/rule defines n 3D spatial positions; n is an integer greater than or equal to 2; the combination of all of said n 3D spatial positions provides a predetermined field of view.

According to the field of view function/rule, the endoscope is relocated if movement has been detected by said detection means, such that said field of view is maintained.

Example 11—Tagged Tool Function/Rule (or Alternatively the Preferred Tool Rule)

Figure 13:
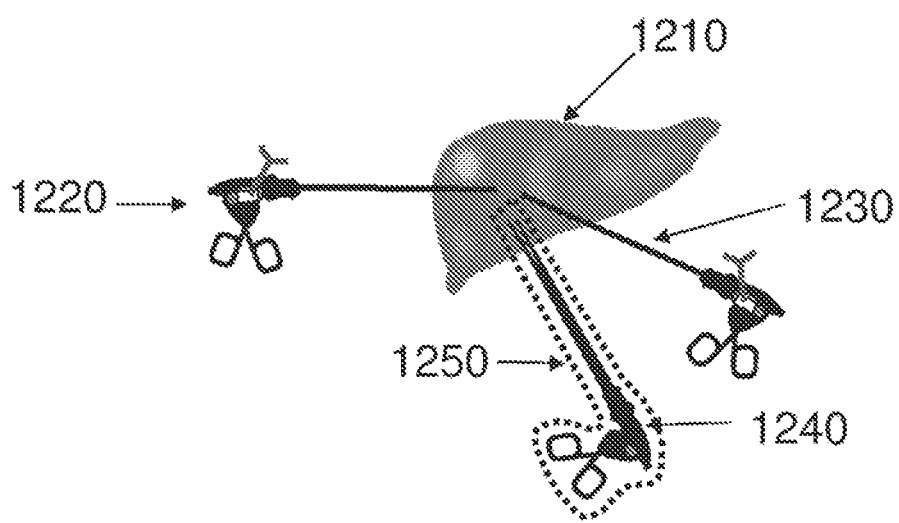
FIG. 13 schematically illustrates operation of an embodiment of the tagged tool function/rule.

In reference to FIG. 13, which shows, in a non-limiting manner, an embodiment of a tagged tool function/rule.

FIG. 12 shows three tools (1220, 1230 and 1240) in proximity to the organ of interest, in this example, the liver 1210.

The tool most of interest to the surgeon, at this point during the operation, is tool 1240. Tool 1240 has been tagged (dotted line 1250); the 3D spacial location of tool 1240 is constantly stored in a database and this spacial location has been labeled as one of interest.

The system can use this tagging for many purposes, including, but not limited to, keeping tool 1240 in the center of the field of view, predicting its future motion, keeping it from colliding with other tools or keeping other tools from colliding with it, instructing the endoscope to constantly monitor and track said tagged tool 1240 and so on.

It should be noted that, in the preferred tool rule, the system tags one of the tools and performs as in the tagged tool rule/function.

Example 12—Proximity Function/Rule

Figure 14A:
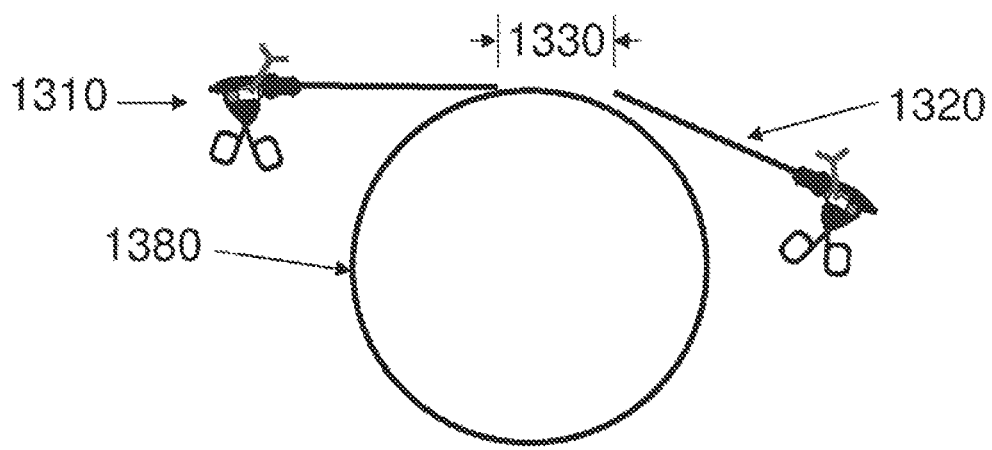
FIG. 14A-C schematically illustrates operation of an embodiment of the proximity function/rule.
Figure 14B:
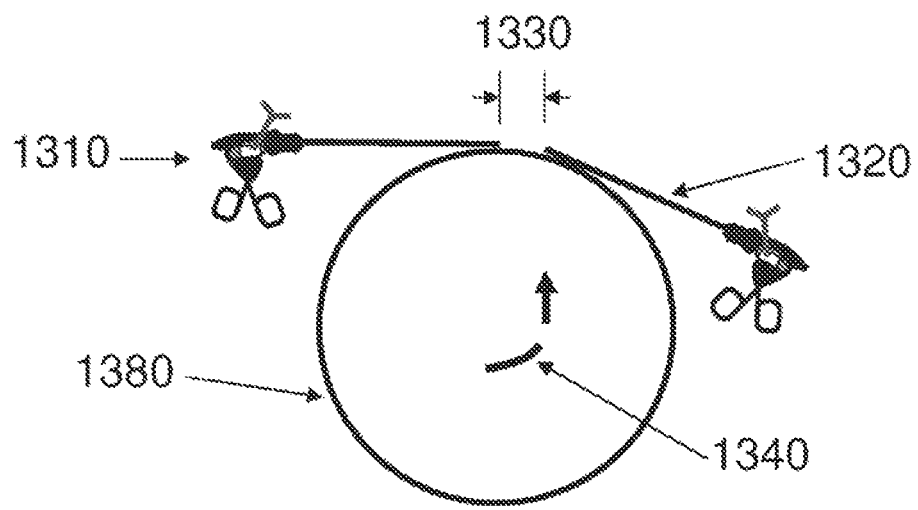
Figure 14C:
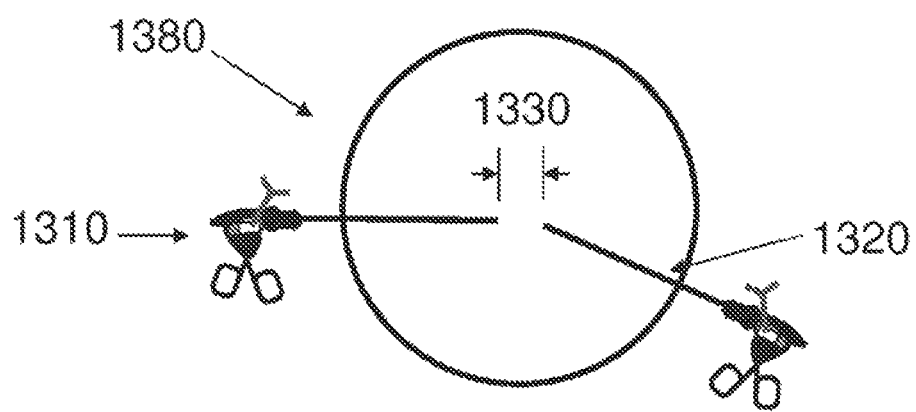

In reference to FIG. 14A-C, which shows, in a non-limiting manner, an embodiment of a proximity function/rule.

FIG. 14A schematically illustrates two tools (1310 and 1320) separated by a distance 1330 which is greater than a predefined proximity distance. Since tool 1310 is not within proximity of tool 1320, the field of view (1380) does not move.

FIG. 14B schematically illustrates two tools (1310 and 1320) separated by a distance 1330 which is less than a predefined proximity distance.

Since tool 1310 is within proximity of tool 1320, the field of view 1380 moves upward, illustrated schematically by arrow 1340, until the tips of tool 1310 and tool 1320 are in the center of field of view 1380 (FIG. 14C).

Alternatively the once the distance 1330 between the two tools 1320 and 1310 is smaller than a predetermined distance, the system alerts the user of said proximity (which might lead to a collision between the two tools). Alternatively, the system moves one of the tools away from the other one.

Example 13—Operator Input Function/Rule

Figure 15A:
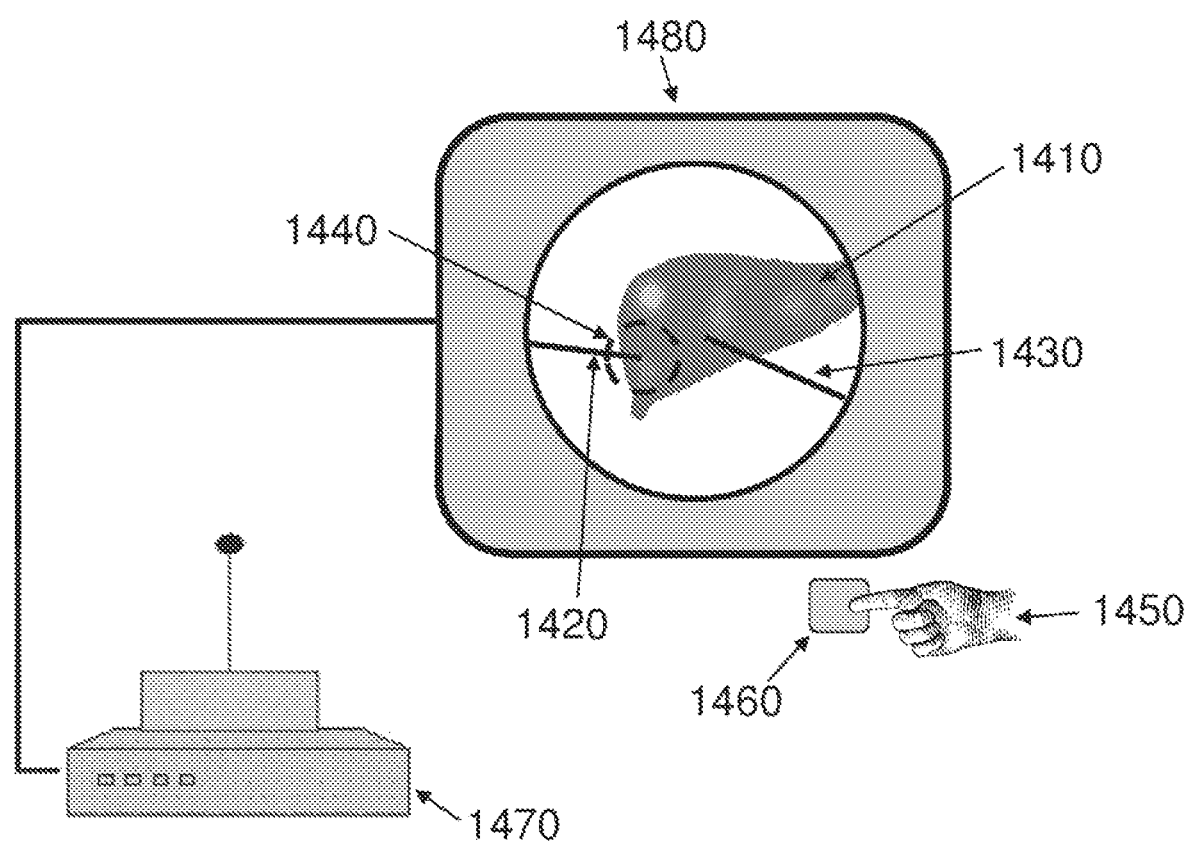
FIG. 15A-B schematically illustrates operation of an embodiment of the operator input function/rule.
Figure 15B:
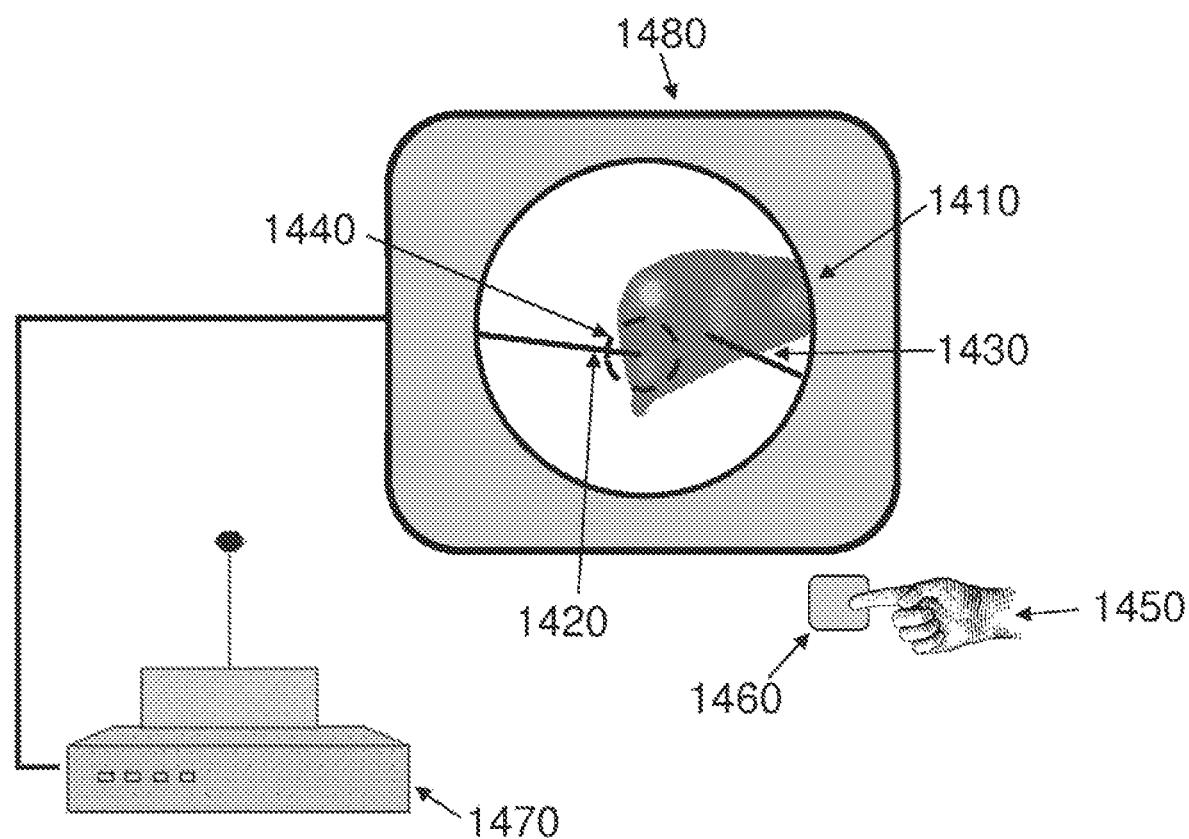

In reference to FIG. 15A-B, which shows, in a non-limiting manner, an embodiment of an operator input function/rule. According to this embodiment, input is received from the operator.

In the following example, the input received from the operator is which tool to track.

FIG. 15A schematically illustrates an endoscope with field of view 1480 showing a liver 1410 and two tools 1420 and 1430. A wireless transmitter 1460 is enabled to transmit coded instructions through receiver 1470. Operator 1450 first selects the tip of the left tool as the region of interest, causing the system to tag (1440) the tip of the left tool.

As illustrated in FIG. 15B, after selection of the tip of tool 1420 by operator 1450 by means of wireless transmitter 1460 and receiver 1470, the system then directs and modifies the spatial position of the endoscope so that the tagged tip 1440 of tool 1420 is in the center of the field of view 1480. In this non-limiting example, the liver 1410 and the tool 1430

Another example of the operator input function/rule is the following:

If a tool has been moved closely to an organ in the surgical environment, according to the proximity rule or the collision prevention rule, the system will, according to one embodiment, prevent the movement of the surgical tool.

According to one embodiment of the present invention, once the surgical tool has been stopped, any movement of said tool in the direction is interpreted as input from the operator to continue the movement of said surgical tool in said direction.

Thus, according to this embodiment, the operator input function/rule receives input from the operator (i.e., physician) to continue the move of said surgical tool (even though it is "against" the collision prevention rule). Said input is simply in the form of the continued movement of the surgical tool (after the alert of the system or after the movement prevention by the system).

Example 14—Constant Field of View Rule/Function

In reference to FIGS. 16A-D, which shows, in a non-limiting manner, an embodiment of a tracking system with a constant field of view rule/function.

In many endoscopic systems, the tip lens in the camera optics is not at a right angle to the sides of the endoscope. Conventionally, the tip lens angle is described relative to the right angle, so that a tip lens at right angles to the sides of the endoscope is described as having an angle of 0. Typically, angled endoscope tip lenses have an angle of 30° or 45°. This tip lens angle affects the image seen during zooming. FIG. 16A-D illustrates, in an out-of-scale manner, for a conventional system, the effect of zooming in the field of view in an endoscope with tip lens set straight in the end (FIGS. 16A and 16B) vs. the effect of zooming in the field of view in an endoscope with angled tip lens (FIGS. 16C and 16D).

Figure 16A:
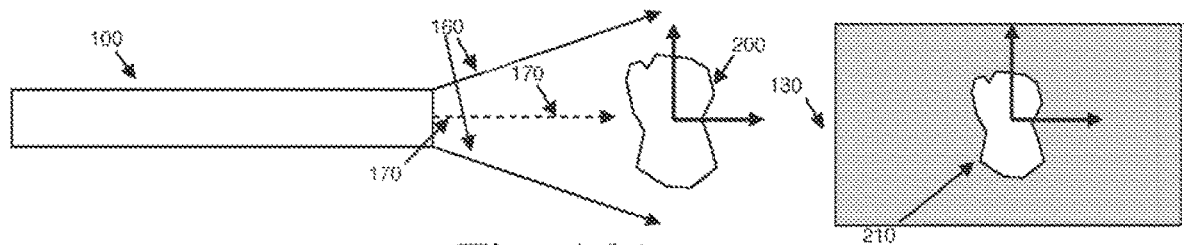
FIGS. 16A-D schematically illustrate an embodiment of a tracking system with a constant field of view rule/function FIG. 17 schematically illustrates an embodiment of a tracking system with a change of speed rule/function
Figure 16B:
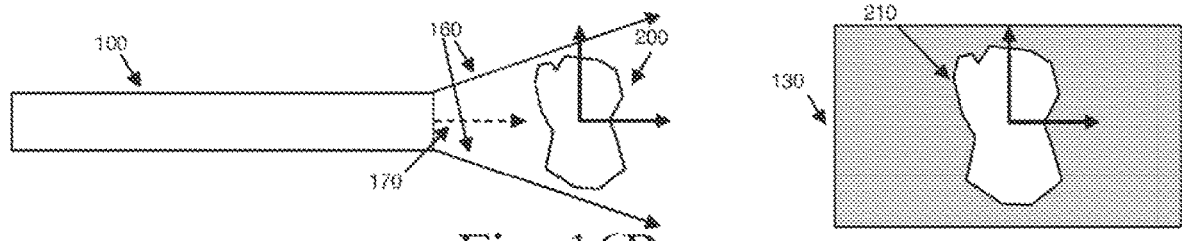
Figure 16C:
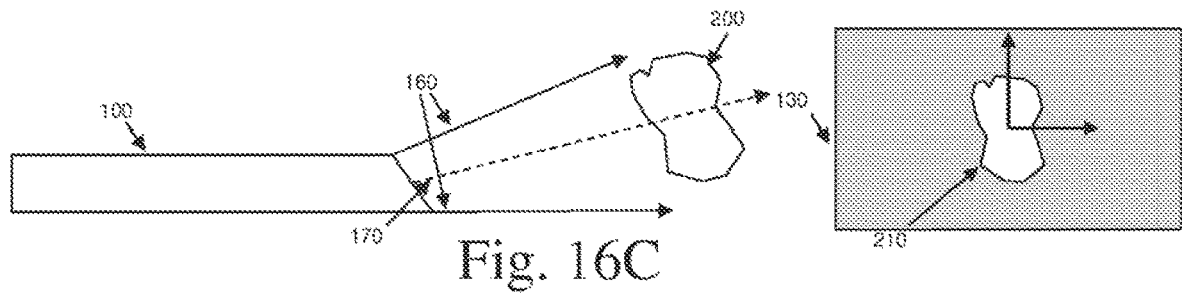
Figure 16D:
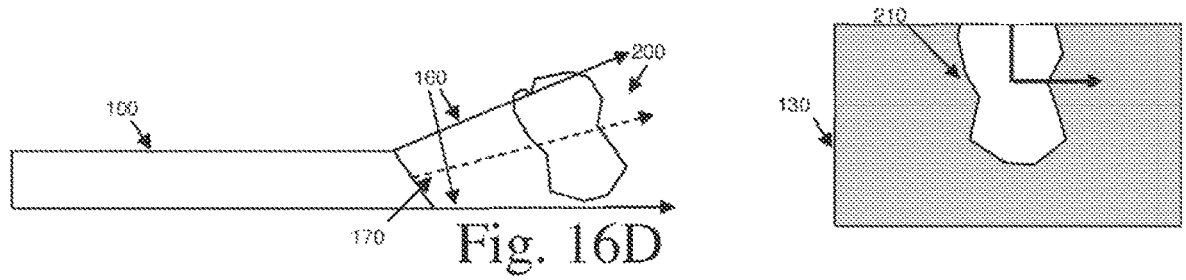

FIGS. 16A and 16C illustrate the endoscope (100), the object it is viewing (200) and the image seen by the endoscope camera (130) before the zoom. The solid arrows (160) show the limits of the field of view (FOV) and the dashed arrow (170), the center of the FOV; since the object is in the center of the FOV, an image of the object (210) is in the center of the camera image (130).

FIGS. 16B and 16D illustrate the endoscope (100), the object it is viewing (200) and the image seen by the endoscope camera (130) after the zoom. The solid arrows (160) show the limits of the FOV and the dashed arrow (170), the center of the field of view.

If the tip lens is set straight in the end of the endoscope (FIGS. 16A and 16B), an object (200) in the center FOV will be in the center of the FOV (and the camera image) (130) both before (FIG. 16A) and after (FIG. 16B) the zoom. However, if the tip lens is set at an angle in the end of the endoscope (FIGS. 16C and 16D), then an object that is in the center of the FOV (and the camera image) before the zoom (FIG. 16C) will not be in the center of the FOV (or the camera image) after the zoom (FIG. 16D) since the direction of motion of the endoscope is not the direction in which the center of the field of view (170) points.

In an embodiment of the system of the present invention, unlike in conventional systems, the controlling means maintains the center of the field of view (FOV) during zoom independent of the tip lens angle. An advantage of controlling the zoom of the endoscope via a data processing system is that the tip lens angle does not need to be input to the data processing system, obviating a possible source of error.

According to one embodiment of the present invention, the endoscope's movement will be adjusted in order to maintain a constant field of view.

Example 15—Misalignment Rule/Function

According to another embodiment of the present invention, the system can inform the user of any misalignment of the same system.

Misalignment of the system may cause parasitic movement of the endoscope tip, where the endoscope tip does not move exactly in the expected direction. According to one embodiment of the system, the system comprises sensors (e.g., gyroscopes, accelometers and any combination thereof) that calculate/estimates the position of the pivot point in real time in order to (a) inform the user of misalignment; or (b) calculate the misalignment so that the system can adjust its movement to prevent parasitic movement.

Example 16—Change of Speed Rule/Function

Figure 17:
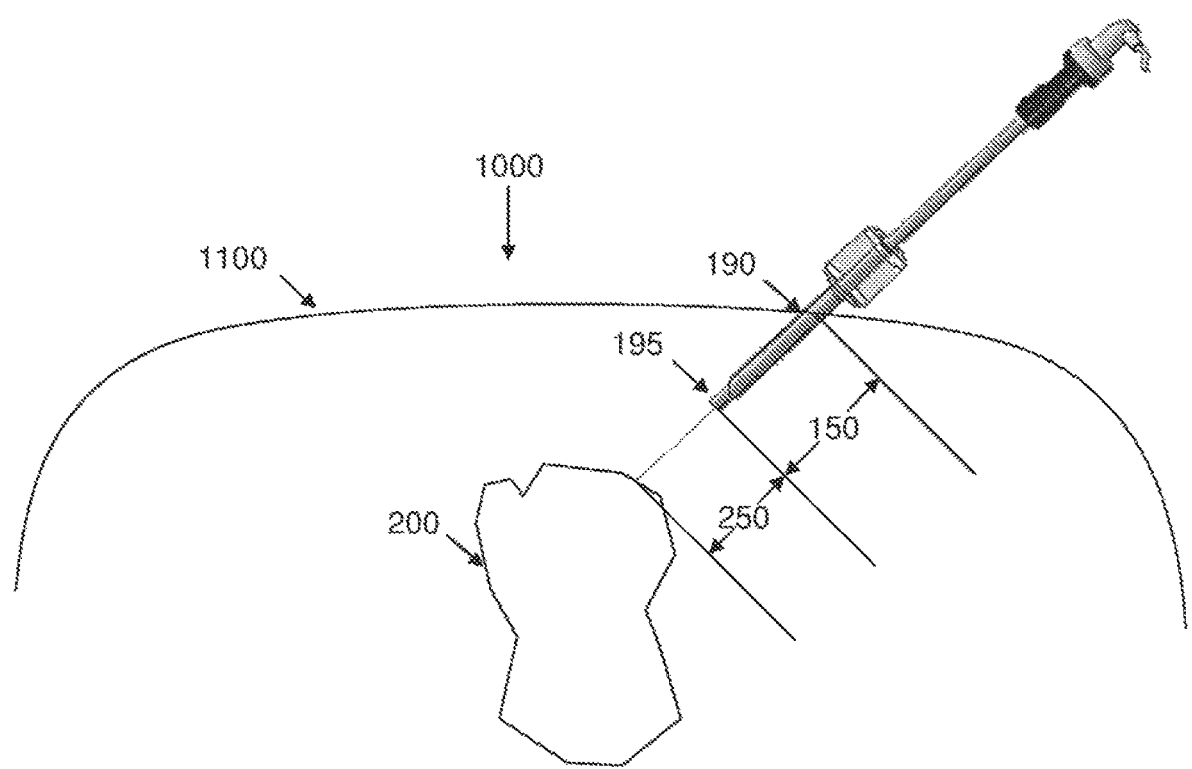

In reference to FIG. 17, which shows, in a non-limiting manner, an embodiment of a tracking system with a change of speed rule/function.

In conventional endoscopic control systems, motion of the endoscope occurs at a single speed. This speed is fairly fast so that the endoscope can be moved rapidly between locations that are well separated. However, this means that making fine adjustments is so difficult that fine adjustments are normally not made. In an embodiment of the present invention, the speed of the tip of the endoscope is automatically varied such that, the closer the endoscope tip is to an object, be it a tool, an obstacle, or the object of interest, the more slowly it moves. In this embodiment, as shown in FIG. 17, measurements are made of the distance X (150) from the tip (195) of the endoscope (100) to the pivot point of the endoscope (190), where said pivot point is at or near the surface of the skin (1100) of a patient (1000). Measurements are also made of the distance Y (250) from the tip of the endoscope (195) to the object (200) in the center of the FOV. From a predetermined velocity $V_p$, the actual velocity of the tip of the endoscope at a given time, $V_{act}$, is calculated from $$V_{act} \propto \frac{Y}{X} V_p$$

Therefore, the closer to the object at the center of the FOV, the more slowly the endoscope moves, making it possible to use automatic control of even fine adjustments, and reducing the probability that the endoscope will come in contact with tissue or instruments.

In embodiments of the system, the harder the control unit is pressed, the faster the endoscope tip moves. In these embodiments, the system provides a warning if the speed is above a predetermined maximum. Examples of the method of warning include, but are not limited to, a constant volume tone, a constant pitch tone, a varying volume tone, a varying pitch tone, a vocal signal, a constant color visual signal, a constant brightness visual signal, a varying color visual signal, a varying brightness visual signal, a signal visible on at least some part of the endoscope image, a signal visible on at least some portion of the patient, a signal visible in at least some portion of the surroundings of the patient, a vibration in the control unit, a temperature change in the control unit, and any combination of the above.

According to one embodiment of the present invention, the velocity of the endoscope's movement will be adjusted as a function of the distance of the endoscope's tip from the organ/tissue.

In the foregoing description, embodiments of the invention, including preferred embodiments, have been presented for the purpose of illustration and description. They are not intended to be exhaustive or to limit the invention to the precise form disclosed. Obvious modifications or variations are possible in light of the above teachings. The embodiments were chosen and described to provide the best illustration of the principals of the invention and its practical application, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

The invention claimed is:

1. A surgical controlling system, comprising:
at least one surgical tool configured to be insertable into a surgical environment of a human body for assisting a surgical procedure;
at least one location estimating means configured to real-time locate a 3D spatial position of said at least one surgical tool at any given time t;
at least one movement detection means communicable with a movement's database and with said location estimating means; said movement's database is configured to store said 3D spatial position of said at least one surgical tool at time tf and at time to; where tf>to; said movement detection means is configured to detect movement of said at least one surgical tool if the 3D spatial position of said at least one surgical tool at time tf is different than said 3D spatial position of said at least one surgical tool at time to; and,
a controller having a processing means communicable with a controller's database, said controller configured to control the spatial position of said at least one surgical tool; said controller's database is in communication with said movement detection means;
wherein a predetermined set of rules is storable in said controller's database, according to which ALLOWED and RESTRICTED movements of said at least one surgical tool are determinable; for each detected movement by said movement detection means, determination of said at least one detected movement as either an ALLOWED movement or as a RESTRICTED movement being according to said predetermined set of rules; further wherein predetermined set of rules is determined using image processing means
wherein said predetermined set of rules comprises at least one rule comprising an environmental rule, wherein said environmental rule comprises a communicable database; said communicable database configured to receive at least one real-time image of said surgical environment and is configured to perform real-time image processing of the same and to determine the 3D spatial position of hazards or obstacles in said surgical environment; said environmental rule is configured to determine said ALLOWED and RESTRICTED movements according to said hazards or obstacles in said surgical environment, wherein said RESTRICTED movements are movements in which said at least one surgical tool is located substantially in at least one of said 3D spatial positions, and said ALLOWED movements are movements in which the location of said at least one surgical tool is substantially different from said 3D spatial positions; further wherein said hazards or obstacles in said surgical environment are selected from a group consisting of tissue, a surgical tool, an organ, an endoscope and any combination thereof.

2. A surgical controlling system, comprising:
at least one surgical tool configured to be insertable into a surgical environment of a human body for assisting a surgical procedure;
at least one location estimating means configured to real-time locate a 3D spatial position of said at least one surgical tool at any given time t;
at least one movement detection means communicable with a movement's database and with said location estimating means; said movement's database is configured to store said 3D spatial position of said at least one surgical tool at time tf and at time to; where tf>to; said movement detection means is configured to detect movement of said at least one surgical tool if the 3D spatial position of said at least one surgical tool at time tf is different than said 3D spatial position of said at least one surgical tool at time to; and,
a controller having a processing means communicable with a controller's database, said controller configured to control the spatial position of said at least one surgical tool; said controller's database is in communication with said movement detection means;
wherein a predetermined set of rules is storable in said controller's database, according to which ALLOWED and RESTRICTED movements of said at least one surgical tool are determinable; for each detected movement by said movement detection means, determination of said at least one detected movement as either an ALLOWED movement or as a RESTRICTED movement being according to said predetermined set of rules; further wherein predetermined set of rules is determined using image processing means wherein said predetermined set of rules comprises at least one rule comprising an operator input rule, wherein said operator input rule comprises a communicable database; said communicable database is configured to receive an input from the operator of said surgical controlling system regarding said ALLOWED and RESTRICTED movements of said at least one surgical tool; wherein said operator input rule converts an ALLOWED movement to a RESTRICTED movement and a RESTRICTED movement to an ALLOWED movement; further wherein at least one of the following is being held true (a) said input comprises n 3D spatial positions; n is an integer greater than or equal to 2;

wherein at least one of which is defined as ALLOWED location and at least one of which is defined as RESTRICTED location, wherein said ALLOWED movements are movements in which said at least one surgical tool is located substantially in at least one of said n 3D spatial positions, and said RESTRICTED movements are movements in which the location of said at least one surgical tool is substantially different from said n 3D spatial positions; (b) said input comprises at least one rule according to which ALLOWED and RESTRICTED movements of said at least one surgical tool are determined, wherein the spatial position of said at least one surgical tool is controlled by said controller according to said ALLOWED and RESTRICTED movements; said predetermined set of rules comprises at least one rule selected from a group consisting of: most used tool, right tool rule, left tool rule, field of view rule, no fly zone rule, route rule, environmental rule, operator input rule, proximity rule; collision prevention rule, preferred volume zone rule, preferred tool rule, movement detection rule, history-based rule, tool-dependent allowed and RESTRICTED movements rule, and any combination thereof.

3. A surgical controlling system, comprising:
at least one surgical tool configured to be insertable into a surgical environment of a human body for assisting a surgical procedure;
at least one location estimating means configured to real-time locate a 3D spatial position of said at least one surgical tool at any given time t;
at least one movement detection means communicable with a movement's database and with said location estimating means; said movement's database is configured to store said 3D spatial position of said at least one surgical tool at time tf and at time to; where tf>to; said movement detection means is configured to detect movement of said at least one surgical tool if the 3D spatial position of said at least one surgical tool at time tf is different than said 3D spatial position of said at least one surgical tool at time to; and,
a controller having a processing means communicable with a controller's database, said controller configured to control the spatial position of said at least one surgical tool; said controller's database is in communication with said movement detection means;
wherein a predetermined set of rules is storable in said controller's database, according to which ALLOWED and RESTRICTED movements of said at least one surgical tool are determinable; for each detected movement by said movement detection means, determination of said at least one detected movement as either an ALLOWED movement or as a RESTRICTED movement being according to said predetermined set of rules; further wherein predetermined set of rules is determined using image processing means wherein said predetermined set of rules comprises at least one rule comprising a proximity rule, wherein said proximity rule is configured to define at least one selected from a group consisting of (a) a predetermined distance between at least two surgical tools; said ALLOWED movements are movements which are within the range or out of the range of said predetermined distance, and said RESTRICTED movements which are out of the range or within the range of said predetermined distance; (b) a predetermined angle between at least three surgical tools; said ALLOWED movements are movements which are within the range or out of the range of said predetermined angle, and said RESTRICTED movements which are out of the range or within the range of said predetermined angle; and combinations thereof.

4. A surgical controlling system, comprising:
at least one surgical tool configured to be insertable into a surgical environment of a human body for assisting a surgical procedure;
at least one location estimating means configured to real-time locate a 3D spatial position of said at least one surgical tool at any given time t;
at least one movement detection means communicable with a movement's database and with said location estimating means; said movement's database is configured to store said 3D spatial position of said at least one surgical tool at time tf and at time to; where tf>to; said movement detection means is configured to detect movement of said at least one surgical tool if the 3D spatial position of said at least one surgical tool at time tf is different than said 3D spatial position of said at least one surgical tool at time to; and,
a controller having a processing means communicable with a controller's database, said controller configured to control the spatial position of said at least one surgical tool; said controller's database is in communication with said movement detection means;
wherein a predetermined set of rules is storable in said controller's database, according to which ALLOWED and RESTRICTED movements of said at least one surgical tool are determinable; for each detected movement by said movement detection means, determination of said at least one detected movement as either an ALLOWED movement or as a RESTRICTED movement being according to said predetermined set of rules; further wherein predetermined set of rules is determined using image processing means wherein said predetermined set of rules comprises at least one rule comprising a collision prevention rule, wherein said collision prevention rule is configured to define a predetermined distance between said at least one surgical tool and an anatomical element within said surgical environment; said ALLOWED movements are movements which are in a range that is larger than said predetermined distance, and said RESTRICTED movements are movements which is in a range that is smaller than said predetermined distance; wherein said anatomical element is selected from a group consisting of tissue, organ, another surgical tool and any combination thereof.

\* \* \* \* \*